(12) United States Patent
Richter et al.

(10) Patent No.: US 10,208,308 B2
(45) Date of Patent: Feb. 19, 2019

(54) MATRIPTASE INHIBITORS AND USES THEREOF AGAINST ORTHOMYXOVIRIDAE INFECTIONS

(71) Applicant: Socpra Sciences Sante Et Humaines S.E.C., Sherbrooke (CA)

(72) Inventors: Martin Richter, Sherbrooke (CA); Richard Leduc, Sherbrooke (CA); Eloic Colombo, Sherbrooke (CA); Eric Marsault, Sherbrooke (CA)

(73) Assignee: Socpra Sciences Sante Et Humaines S.E.C., Sherbrooke, Quebec (CA)

( * ) Notice: Subject to any disclaimer, the term of this patent is extended or adjusted under 35 U.S.C. 154(b) by 0 days.

(21) Appl. No.: 15/647,878

(22) Filed: Jul. 12, 2017

(65) Prior Publication Data
US 2017/0314023 A1    Nov. 2, 2017

Related U.S. Application Data

(62) Division of application No. 14/943,716, filed on Nov. 17, 2015, now Pat. No. 9,752,149, which is a division of application No. 14/118,768, filed as application No. PCT/CA2012/050349 on May 28, 2012, now Pat. No. 9,365,853.

(60) Provisional application No. 61/492,556, filed on Jun. 2, 2011.

(51) Int. Cl.
| | |
|---|---|
| *A61K 31/428* | (2006.01) |
| *C12N 15/113* | (2010.01) |
| *A61K 45/06* | (2006.01) |
| *A61K 31/713* | (2006.01) |
| *C12N 9/64* | (2006.01) |
| *A61K 31/427* | (2006.01) |
| *C07K 16/40* | (2006.01) |
| *A61K 38/07* | (2006.01) |
| *C07K 5/11* | (2006.01) |
| *C07K 5/062* | (2006.01) |
| *C07K 5/093* | (2006.01) |
| *C07K 5/09* | (2006.01) |
| *C07K 5/072* | (2006.01) |
| *A61K 38/06* | (2006.01) |
| *A61K 9/00* | (2006.01) |
| *A61K 39/00* | (2006.01) |
| *A61K 38/00* | (2006.01) |

(52) U.S. Cl.
CPC ........ *C12N 15/1131* (2013.01); *A61K 31/427* (2013.01); *A61K 31/428* (2013.01); *A61K 31/713* (2013.01); *A61K 38/06* (2013.01); *A61K 38/07* (2013.01); *A61K 45/06* (2013.01); *C07K 5/06026* (2013.01); *C07K 5/06095* (2013.01); *C07K 5/06104* (2013.01); *C07K 5/0817* (2013.01); *C07K 5/0819* (2013.01); *C07K 5/1019* (2013.01); *C07K 16/40* (2013.01); *C12N 9/6424* (2013.01); *A61K 9/0075* (2013.01); *A61K 9/0078* (2013.01); *A61K 38/00* (2013.01); *A61K 2039/505* (2013.01); *C07K 2317/565* (2013.01); *C07K 2317/76* (2013.01); *C12N 2310/14* (2013.01)

(58) Field of Classification Search
CPC .... A61K 31/42; A61K 31/427; A61K 31/428; A61K 31/41; A61K 31/425
See application file for complete search history.

(56) References Cited

U.S. PATENT DOCUMENTS

| | | | |
|---|---|---|---|
| 5,723,439 A * | 3/1998 | Zhirnov | A61K 9/0075 424/499 |
| 6,677,377 B2 | 1/2004 | Lin et al. | |
| 7,019,019 B2 | 3/2006 | Duncan et al. | |
| 7,572,444 B2 | 8/2009 | Foltz et al. | |
| 7,772,251 B2 | 8/2010 | Sturzebecher et al. | |
| 9,365,853 B2 * | 6/2016 | Richter | A61K 45/06 |
| 9,752,149 B2 * | 9/2017 | Richter | A61K 45/06 |
| 2006/0177875 A1 | 8/2006 | Hunt et al. | |
| 2010/0075910 A1 | 3/2010 | Schteingart et al. | |
| 2010/0305090 A1 | 12/2010 | Steinmetzer et al. | |
| 2016/0097052 A1 | 4/2016 | Richter et al. | |

FOREIGN PATENT DOCUMENTS

| | | | | |
|---|---|---|---|---|
| WO | WO-9640748 A1 * | 12/1996 | | C07D 277/56 |
| WO | WO-199640748 A1 | 12/1996 | | |
| WO | WO-1999026925 A1 | 6/1999 | | |
| WO | WO-0044733 A1 * | 8/2000 | | C07D 277/64 |
| WO | WO-200044733 A1 | 8/2000 | | |
| WO | WO-200110894 A2 | 2/2001 | | |
| WO | WO-200220475 A2 | 3/2002 | | |
| WO | WO-2007104070 A1 | 9/2007 | | |

(Continued)

OTHER PUBLICATIONS

Furlong et al., Immunopharmacology vol. 48 pp. 199-212 (Year: 2000).*

(Continued)

*Primary Examiner* — Timothy P Thomas
*Assistant Examiner* — George W Kosturko
(74) *Attorney, Agent, or Firm* — McCarter & English, LLP

(57) ABSTRACT

The present invention provides matriptase inhibitors and compositions for treating and preventing orthomyxovirus infections such as flue infections. The present invention also provides novel compounds, compositions, methods of use, uses and kits thereof for inhibiting matriptase. Such compounds are useful for treating and prevention orthomyxovirus infections, such as flu infections, and for inhibiting tumor growth, progression and/or metastasis.

14 Claims, 17 Drawing Sheets
Specification includes a Sequence Listing.

(56) References Cited

FOREIGN PATENT DOCUMENTS

| WO | WO-2011035128 A1 | 3/2011 |
|---|---|---|
| WO | WO-2011050276 A1 | 4/2011 |

OTHER PUBLICATIONS

Costanzo et al., J. Med. Chem. vol. 48 pp. 1984-2008. (Year: 2005).*
Furlong et al., Immunopharmacology vol. 48 pp. 199-212. Published 2000. (Year: 2000).*
Asano, et al., Novel Retrovirus Protease Inhibitors, RPI-856 A, B, C and D, Produced by *Streptomyces* sp. AL-322, The Journal of Antibiotics, (1994) 47(5):557-565.
Baron, et al., Matriptase, HAT, and TMPRSS2 Activates the Hemagglutinin of H9N2 Influenza A Viruses, Journal of Virology, (2013) 87(3):1811-1820.
Beaulieu, et al., Matriptase Proteolytically Activates Influenza virus and Promotes Multicyle Replication in the Human Airwauy Epithelium, J. Virol. (2006), 87(8):4237-4251.
Bertram et al., TMPRSS2 and TMPRSS4 Facilitate Trypsin-Independent Spread of Influenza Virus n Caco-2 Cells. Journal of Virology. Oct. 2010;84(19):10016-10025.
Bottcher, et al., Proteolytic activation of influenza viruses by serine proteases TMPRSS2 and HAT from human airaway epithelium, J. Virol. (2006) 80:9896-9898.
Bullough et al., Structure of influenza haemagglutinin at the pH of membrane fusion, Nature (1994) 371:37-43.
Buzza, et al., Membrane-anchored serine protease matriptase regualtes epithelial barrier formation and permeability in the intestine, PNAS, (2010) 107(9):4200-4205.
Colombo, et al., Design and Synthesis of Potent, Selective Inhibitors of Matriptase, ACS Medicinal Chemistry Lett, (2012) 3:530-534.
Costanzo et al., In-depth study of tripeptide-based alpha-ketoheterocycles as inhibitors of thrombin. Effective utilization of the S1' subsite and its implications to structure-based drug design. J Med Chem. Mar. 24, 2005;48(6):1984-2008.
Cox, et al., Global epidemiology of influenza past and present, Annu Rev Med, (2000) 51:407-421.
De Clerck, E. Antiviral agents active against influenza A viruses, Nat Rev Drug Discov, (2006) 5:1015-1025.
Desilets, et al., Inhibition of human matripase by eglin c variants, FEBS Letters, (2006) 580:2227-2232.
Ferreira, et al., Weak bases affect late stages of Mavaro virus replication cycle in verterbrate cells, Journal of Medical Microbiology, (2000) 49:313-318.
Furlong et al., C3 activation is inhibited by analogs of compstatin but not by serine protease inhibitors or peptidyl alpha-ketoheterocycles. Immunopharmacology. Jul. 20, 2000;48(2):199-212.
Galkin et al., CVS-3983, a selective matriptase inhibitor, suppresses the growth of androgen independent prostate tumor xenografts. Prostate. Nov. 1, 2004;61(3):228-35.
Garten et al., Cleavage activation of the influenza virus hemagglutinin and its role in pathogenesis, (2008), Karger, Basel, Switzerland.

Hamilton, et al., Cleavage Activationo f the Human-Adapted Influenza Virus Subtypes by Matripase Reveals both Subtype and Strain Specificities, J. Virol. (2012) 86(19):10579-10586.
Hayden, et al., Emergence and transmission of influenza A viruses resistant to amantadine and rimantadine, Curr Top Microbiol Immunol, (1992) 176:119-130.
Kido, et al., Cellular Proteases Involved in the Pathogenicity of Enveloped Animal Viruses, Human Immunodeficiency Virus, Influenza Virus A and Sendai Virus, Advan. Enzyme Regul., (1996) 36:325-347.
Kido, et al., Cellular proteases involved in the pathogenicity of human immunodeficiency and influenza viruses, Adv Exp Med biol, (1996) 389:233-240.
Klenk, et al., Host cell proteases controlling virus pathogenicity, Trends Microbiol. (1994), 2:39-43.
Klenk, et al., Inhibition of proteolytic cleavage of the hamagglutinin of influenza virus by the calcium-specific ionophore A23187, EMBO J., (1984) 3;(12):2911-2915.
Presti et al., Quaranfil, Johnston Atoll, and Lake Chad viruses are novel members of the family Orthomyxoviridae. J Virol. Nov. 2009;83(22):11599-606.
Pubchem: AGN-PC-075PSQ: http://pubchem.ncbi.nlm.nih.gov// compound/22980724?from=summary, Dec. 5, 2007 (retrieved Jan. 2, 2015).
Pubchem: AGN-PC-0CPU7J: http://pubchem.ncbi.nlm.nih.gov// compound/22980757?from=summary#section=top, Dec. 5, 2007 (retrieved Jan. 2, 2015).
Sigma-Aldrich™, Aprotinin. bovine, recombinant, expressed in *Nicotiana* (tobacco). Product information. 3 pages (1983).
Skehel, et al., Receptor binding and membrane fusion in virus entry: the influenza hemagglutinin, Annu. Rev. Biochem., (2000) 69:531-569.
Sollner, T.H., Intracellular and viral membrane fusion: a uniting mechanism, Curr Opin Cell Biol, (2004) 16:429-435.
Steinhauser, D.A., Role of hemagglutinin cleavage for the pathogenicity of influenza virus, Virology, (1999) 258:1-20.
Steinhauser, et al., Studies using double mutanst of the conformational transitions in influenza hemagglutinin required for its membrane fusion activity, Proc Natl Acad Sci, (1996) 93:12873-12878.
Stieneke-Grober, et al., Influenza virus hemagglutinin with multibasic cleavage site is activated by furin, a subtilisin-like endoprotease, Embo J. (1992), 11:2407-2414.
The Center for Food Security & Public Health, Iowa State University et al., Infectious Salmon Anemia, Hemorrhagic Kidney Syndrome. 7 pages. (Mar. 2010).
Wikipedia, Thogotovirus. Retrieved online at: https://en.wikipedia.org/wiki/Thogotovirus. 11 pages. Jan. 21, 2016.
Yamasaki et al., Inhibition of membrane-type serine protease 1/matriptase by natural and synthetic protease inhibitors. J Nutr Sci Vitaminol. (Tokyo). Feb. 2003;49(1):27-32.
Zambon, M.C., The pathogenesis of influenza in humans, Rev. Med Viorl, (2001), 11:227-241.
International Preliminary Report on Patentability issued in PCT/CA2012/050349 dated Dec. 2, 2013.
Office Action dated Nov. 27, 2013 issue in Eruopean Application No. 12793674.8.

* cited by examiner

A
(start)
atggggagcgatcgggcccgcaagggcggaggggcccgaaggacttcggcgcgggactcaagtacaactcccggcacgagaaagtgaatg
gcttggaggaaggcgtggagttcctgccagtcaacaacgtcaagaaggtggaaaagcatggcccggggcgctgggtggtgctggcagccgtgct
gatcggcctcctcttggtcttgctggggatcggcttcctggtgtggcatttgcagtaccgggacgtgcgtgtccagaaggtcttcaatggctacatgag
gatcacaaatgagaattttgtggatgcctacgagaactccaactccactgagtttgtaagcctggccagcaaggtgaaggacgcgctgaagctgctgt
acagcggagtccattcctgggcccctaccacaaggagtcggctgtgacggccttcagcgagggcagcgtcatcgcctactactggtctgagttcag
catcccgcagcacctggtggaggaggccgagcgcgtcatggccgaggagcgcgtagtcatgctgcccccgcgggcgcgctccttgaagtcctttg
tggtcacctcagtggtggctttccccacggactccaaaacagtacagaggaccccaggacaacagctgcagctttggcctgcacgcccgcggtgtgg
agctgatgcgcttcaccacgcccggcttccctgacagccctacccgctcatgcccgctgccagtgggccctgcggggggacgccgactcagtg
ctgagcctcaccttccgcagctttgaccttgcgtcctgcgacgagcgcggcagcgacctggtgacggtgtacaacaccctgagccccatggagccc
cacgccctggtgcagttgtgtggcacctaccctccctcctacaacctgaccttccactcctcccagaacgtcctgctcatcacactgataaccaacact
gagcggcggcatcccggctttgaggccaccttcttccagctgcctaggatgagcagctgtggaggccgcttacgtaaagcccaggggacattcaac
agccctactacccaggccactacccacccaacattgactgcacatggaacattgaggtgcccaacaaccagcatgtgaaggtgcgcttcaaattctt
ctacctgctggagcccggcgtgcctgcgggcacctgccccaaggactacgtggagatcaatggggagaaatactgcggagagaggtcccagttcg
tcgtcaccagcaacagcaacaagatcacagttcgcttccactcagatcagtcctacaccgacaccggcttcttagctgaatacctctcctacgactcca
gtgacccatgcccggggcagttcacgtgccgcacggggcggtgtatccggaaggagctgcgctgtgatggctgggccgactgcaccgaccacag
cgatgagctcaactgcagttgcgacgccggccaccagttcacgtgcaagaacaagttctgcaagccccctcttctgggtctgcgacagtgtgaacgac
tgcggagacaacagcgacgagcaggggtgcagttgtccggccagaccttcaggtgttccaatgggaagtgcctctcgaaaagccagcagtgcaa
tgggaaggacgactgtgggggacgggtccgacgaggcctcctgccccaaggtgaacgtcgtcacttgtaccaaacacacctaccgctgcctcaatg
ggctctgcttgagcaaggggcaaccctgagtgtgacgggaaggaggactgtagcgacggctcagatgagaaggactgcgactgtgggctgcggtc
attcacgagacaggctcgtgttgttgggggcacggatgcgatgagggcgagtggccctggcaggtaagcctgcatgctctgggccagggccaca
tctgcggtgcttccctcatctctcccaactggctggtctctgccgcacactgctacatcgatgacagaggattcaggtactcagaccccacgcagtgga
cggccttcctgggcttgcacgaccagagccagcgcagcgcccctggggtgcaggagcgcaggctcaagcgcatcatctcccacccctcttcaatg
acttcaccttcgactatgacatcgcgctgctggagctggagaaaccggcagagtacagctccatggtgcggcccatctgcctgccggacgcctcca
tgtcttccctgccggcaaggccatctgggtcacgggctggggacacacaccagtatggaggcactggcgcgctgatcctgcaaaagggtgagatcc
gcgtcatcaaccagaccacctgcgagaacctcctgccgcagcagatcacgccgcgcatgatgtgcgtgggcttcctcagcggcggcgtggactcct
gccagggtgattccgggggaccccctgtccagcgtggaggcggatgggcggatcttccaggccggtgtggtgagctggggagacggctgcgctca
gaggaacaagccaggcgtgtacacaaggctccctctgtttcgggactggatcaaagagaacactggggtatag (stop)

```
          10         20         30         40         50         60
   MGSDRARKGG GGPKDFGAGL KYNSRHEKVN GLEEGVEFLP VNNVKKVEKH GPGRWVVLAA 70         80         90        100        110        120
   VLIGLLLVLL GIGFLVWHLQ YRDVRVQKVF NGYMRITNEN FVDAYENSNS TEFVSLASKV 130        140        150        160        170        180
   KDALKLLYSG VPFLGPYHKE SAVTAFSEGS VIAYYWSEFS IPQHLVEEAE RVMAEERVVM 190        200        210        220        230        240
   LPPRARSLKS FVVTSVVAFP TDSKTVQRTQ DNSCSFGLHA RGVELMRFTT PGFPDSPYPA 250        260        270        280        290        300
   HARCQWALRG DADSVLSLTF RSFDLASCDE RGSDLVTVYN TLSPMEPHAL VQLCGTYPPS 310        320        330        340        350        360
   YNLTFHSSQN VLLITLITNT ERRHPGFEAT FFQLPRMSSC GGRLRKAQGT FNSPYYPGHY 370        380        390        400        410        420
   PPNIDCTWNI EVPNNQHVKV RFKFFYLLEP GVPAGTCPKD YVEINGEKYC GERSQFVVTS 430        440        450        460        470        480
   NSNKITVRFH SDQSYTDTGF LAEYLSYDSS DPCPGQFTCR TGRCIRKELR CDGWADCTDH 490        500        510        520        530        540
   SDELNCSCDA GHQFTCKNKF CKPLFWVCDS VNDCGDNSDE QGCSCPAQTF RCSNGKCLSK 550        560        570        580        590        600
   SQQCNGKDDC GDGSDEASCP KVNVVTCTKH TYRCLNGLCL SKGNPECGDK EDCSDGSDEK 610        620        630        640        650        660
   DCDCGLRSFT RQARVVGGTD ADEGEWPWQV SLHALGQGHI CGASLISPNW LVSAAHCYID 670        680        690        700        710        720
   DRGFRYSDPT QWTAFLGLHD QSQRSAPGVQ ERRLKRIISH PFFNDFTFDY DIALLELEKP 730        740        750        760        770        780
   AEYSSMVRPI CLPDASHVFP AGKAIWVTGW GHTQYGGTGA LILQKGEIRV INQTTCENLL 790        800        810        820        830        840
   PQQITPRMMC VGFLSGGVDS CQGDSGGPLS SVEADGRIFQ AGVVSWGDGC AQRNKPGVYT

850
   RLPLFRDWIK ENTGV
```

Figure 1B

A
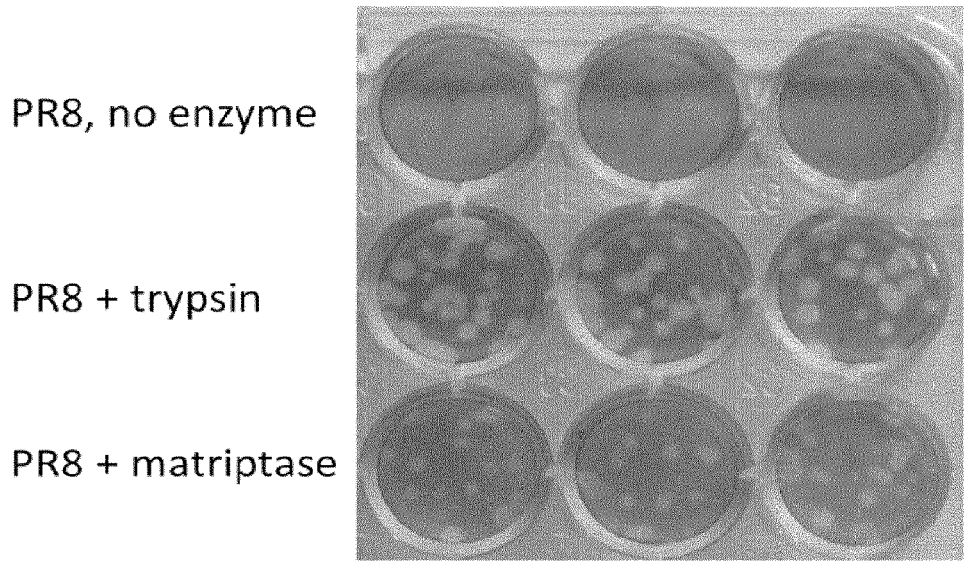
PR8, no enzyme
PR8 + trypsin
PR8 + matriptase
B
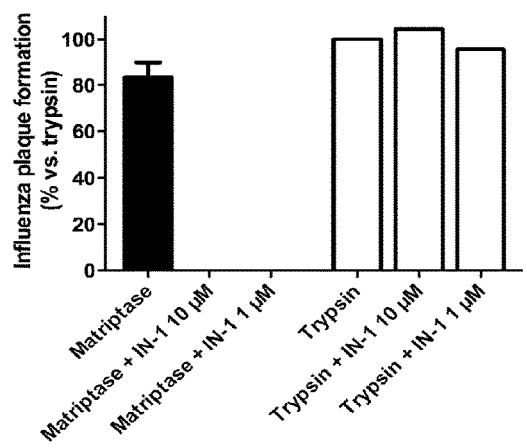
C
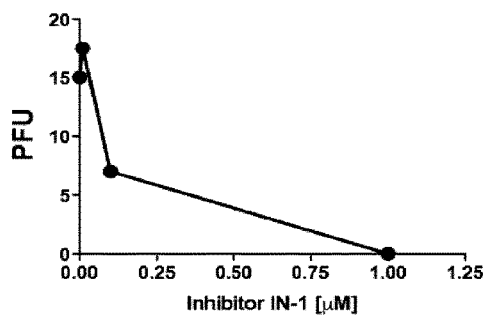
Figure 7

A
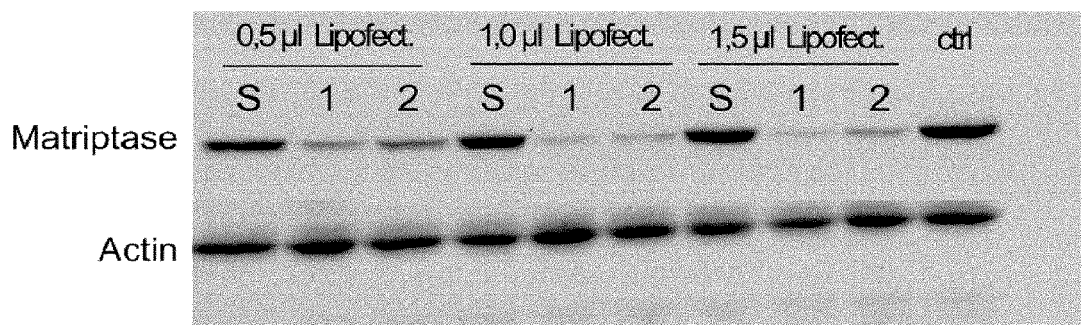
B
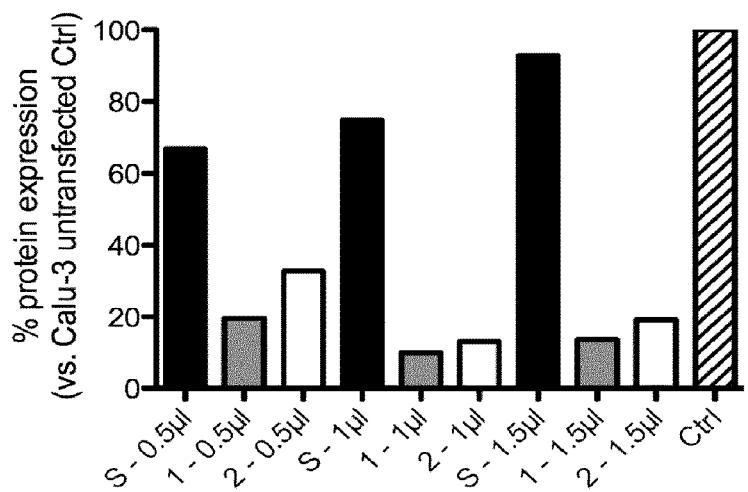
Figure 8

SEQUENCE LISTING

<160> NUMBER OF SEQ ID NOS: 8

<210> SEQ ID NO 1
<211> LENGTH: 2568
<212> TYPE: DNA
<213> ORGANISM: Homo sapiens
<220> FEATURE:
<221> NAME/KEY: CDS
<222> LOCATION: (1)..(2568)

<400> SEQUENCE: 1

```
atg ggg agc gat cgg gcc cgc aag ggc gga ggg ggc ccg aag gac ttc      48
Met Gly Ser Asp Arg Ala Arg Lys Gly Gly Gly Gly Pro Lys Asp Phe
1               5                   10                  15 ggc gcg gga ctc aag tac aac tcc cgg cac gag aaa gtg aat ggc ttg      96
Gly Ala Gly Leu Lys Tyr Asn Ser Arg His Glu Lys Val Asn Gly Leu
            20                  25                  30 gag gaa ggc gtg gag ttc ctg cca gtc aac aac gtc aag aag gtg gaa     144
Glu Glu Gly Val Glu Phe Leu Pro Val Asn Asn Val Lys Lys Val Glu
        35                  40                  45 aag cat ggc ccg ggg cgc tgg gtg gtg ctg gca gcc gtg ctg atc ggc     192
Lys His Gly Pro Gly Arg Trp Val Val Leu Ala Ala Val Leu Ile Gly
    50                  55                  60 ctc ctc ttg gtc ttg ctg ggg atc ggc ttc ctg gtg tgg cat ttg cag     240
Leu Leu Leu Val Leu Leu Gly Ile Gly Phe Leu Val Trp His Leu Gln
65                  70                  75                  80 tac cgg gac gtg cgt gtc cag aag gtc ttc aat ggc tac atg agg atc     288
Tyr Arg Asp Val Arg Val Gln Lys Val Phe Asn Gly Tyr Met Arg Ile
                85                  90                  95 aca aat gag aat ttt gtg gat gcc tac gag aac tcc aac tcc act gag     336
Thr Asn Glu Asn Phe Val Asp Ala Tyr Glu Asn Ser Asn Ser Thr Glu
            100                 105                 110 ttt gta agc ctg gcc agc aag gtg aag gac gcg ctg aag ctg ctg tac     384
Phe Val Ser Leu Ala Ser Lys Val Lys Asp Ala Leu Lys Leu Leu Tyr
        115                 120                 125 agc gga gtc cca ttc ctg ggc ccc tac cac aag gag tcg gct gtg acg     432
Ser Gly Val Pro Phe Leu Gly Pro Tyr His Lys Glu Ser Ala Val Thr
    130                 135                 140 gcc ttc agc gag ggc agc gtc atc gcc tac tac tgg tct gag ttc agc     480
Ala Phe Ser Glu Gly Ser Val Ile Ala Tyr Tyr Trp Ser Glu Phe Ser
145                 150                 155                 160 atc ccg cag cac ctg gtg gag gag gcc gag cgc gtc atg gcc gag gag     528
Ile Pro Gln His Leu Val Glu Glu Ala Glu Arg Val Met Ala Glu Glu
                165                 170                 175 cgc gta gtc atg ctg ccc ccg cgg gcg cgc tcc ttg aag tcc ttt gtg     576
Arg Val Val Met Leu Pro Pro Arg Ala Arg Ser Leu Lys Ser Phe Val
            180                 185                 190 gtc acc tca gtg gtg gct ttc ccc acg gac tcc aaa aca gta cag agg     624
Val Thr Ser Val Val Ala Phe Pro Thr Asp Ser Lys Thr Val Gln Arg
```

-continued

```
              195                 200                 205
acc cag gac aac agc tgc agc ttt ggc ctg cac gcc cgc ggt gtg gag    672
Thr Gln Asp Asn Ser Cys Ser Phe Gly Leu His Ala Arg Gly Val Glu
    210                 215                 220 ctg atg cgc ttc acc acg ccc ggc ttc cct gac agc ccc tac ccc gct    720
Leu Met Arg Phe Thr Thr Pro Gly Phe Pro Asp Ser Pro Tyr Pro Ala
225                 230                 235                 240 cat gcc cgc tgc cag tgg gcc ctg cgg ggg gac gcc gac tca gtg ctg    768
His Ala Arg Cys Gln Trp Ala Leu Arg Gly Asp Ala Asp Ser Val Leu
            245                 250                 255 agc ctc acc ttc cgc agc ttt gac ctt gcg tcc tgc gac gag cgc ggc    816
Ser Leu Thr Phe Arg Ser Phe Asp Leu Ala Ser Cys Asp Glu Arg Gly
        260                 265                 270 agc gac ctg gtg acg gtg tac aac acc ctg agc ccc atg gag ccc cac    864
Ser Asp Leu Val Thr Val Tyr Asn Thr Leu Ser Pro Met Glu Pro His
    275                 280                 285 gcc ctg gtg cag ttg tgt ggc acc tac cct ccc tcc tac aac ctg acc    912
Ala Leu Val Gln Leu Cys Gly Thr Tyr Pro Pro Ser Tyr Asn Leu Thr
290                 295                 300 ttc cac tcc tcc cag aac gtc ctg ctc atc aca ctg ata acc aac act    960
Phe His Ser Ser Gln Asn Val Leu Leu Ile Thr Leu Ile Thr Asn Thr
305                 310                 315                 320 gag cgg cgg cat ccc ggc ttt gag gcc acc ttc ttc cag ctg cct agg   1008
Glu Arg Arg His Pro Gly Phe Glu Ala Thr Phe Phe Gln Leu Pro Arg
            325                 330                 335 atg agc agc tgt gga ggc cgc tta cgt aaa gcc cag ggg aca ttc aac   1056
Met Ser Ser Cys Gly Gly Arg Leu Arg Lys Ala Gln Gly Thr Phe Asn
        340                 345                 350 agc ccc tac tac cca ggc cac tac cca ccc aac att gac tgc aca tgg   1104
Ser Pro Tyr Tyr Pro Gly His Tyr Pro Pro Asn Ile Asp Cys Thr Trp
    355                 360                 365 aac att gag gtg ccc aac aac cag cat gtg aag gtg cgc ttc aaa ttc   1152
Asn Ile Glu Val Pro Asn Asn Gln His Val Lys Val Arg Phe Lys Phe
370                 375                 380 ttc tac ctg ctg gag ccc ggc gtg cct gcg ggc acc tgc ccc aag gac   1200
Phe Tyr Leu Leu Glu Pro Gly Val Pro Ala Gly Thr Cys Pro Lys Asp
385                 390                 395                 400 tac gtg gag atc aat ggg gag aaa tac tgc gga gag agg tcc cag ttc   1248
Tyr Val Glu Ile Asn Gly Glu Lys Tyr Cys Gly Glu Arg Ser Gln Phe
            405                 410                 415 gtc gtc acc agc aac agc aac aag atc aca gtt cgc ttc cac tca gat   1296
Val Val Thr Ser Asn Ser Asn Lys Ile Thr Val Arg Phe His Ser Asp
        420                 425                 430 cag tcc tac acc gac acc ggc ttc tta gct gaa tac ctc tcc tac gac   1344
Gln Ser Tyr Thr Asp Thr Gly Phe Leu Ala Glu Tyr Leu Ser Tyr Asp
    435                 440                 445 tcc agt gac cca tgc ccg ggg cag ttc acg tgc cgc acg ggg cgg tgt   1392
Ser Ser Asp Pro Cys Pro Gly Gln Phe Thr Cys Arg Thr Gly Arg Cys
450                 455                 460 atc cgg aag gag ctg cgc tgt gat ggc tgg gcc gac tgc acc gac cac   1440
Ile Arg Lys Glu Leu Arg Cys Asp Gly Trp Ala Asp Cys Thr Asp His
465                 470                 475                 480 agc gat gag ctc aac tgc agc tgc gac gcc ggc cac cag ttc acg tgc   1488
Ser Asp Glu Leu Asn Cys Ser Cys Asp Ala Gly His Gln Phe Thr Cys
            485                 490                 495 aag aac aag ttc tgc aag ccc ctc ttc tgg gtc tgc gac agt gtg aac   1536
Lys Asn Lys Phe Cys Lys Pro Leu Phe Trp Val Cys Asp Ser Val Asn
        500                 505                 510 gac tgc gga gac aac agc gac gag cag ggg tgc agt tgt ccg gcc cag   1584
Asp Cys Gly Asp Asn Ser Asp Glu Gln Gly Cys Ser Cys Pro Ala Gln
```

-continued

| | | | | | | | | | | | | | |
|---|---|---|---|---|---|---|---|---|---|---|---|---|---|
| Asp | Cys | Gly | Asp | Asn | Ser | Asp | Glu | Gln | Gly | Cys | Ser | Cys | Pro | Ala | Gln |
| | | 515 | | | | 520 | | | | 525 | | | | |

```
acc ttc agg tgt tcc aat ggg aag tgc ctc tcg aaa agc cag cag tgc      1632
Thr Phe Arg Cys Ser Asn Gly Lys Cys Leu Ser Lys Ser Gln Gln Cys
530                 535                 540 aat ggg aag gac gac tgt ggg gac ggg tcc gac gag gcc tcc tgc ccc      1680
Asn Gly Lys Asp Asp Cys Gly Asp Gly Ser Asp Glu Ala Ser Cys Pro
545                 550                 555                 560 aag gtg aac gtc gtc act tgt acc aaa cac acc tac cgc tgc ctc aat      1728
Lys Val Asn Val Val Thr Cys Thr Lys His Thr Tyr Arg Cys Leu Asn
                565                 570                 575 ggg ctc tgc ttg agc aag ggc aac cct gag tgt gac ggg aag gag gac      1776
Gly Leu Cys Leu Ser Lys Gly Asn Pro Glu Cys Asp Gly Lys Glu Asp
            580                 585                 590 tgt agc gac ggc tca gat gag aag gac tgc gac tgt ggg ctg cgg tca      1824
Cys Ser Asp Gly Ser Asp Glu Lys Asp Cys Asp Cys Gly Leu Arg Ser
            595                 600                 605 ttc acg aga cag gct cgt gtt gtt ggg ggc acg gat gcg gat gag ggc      1872
Phe Thr Arg Gln Ala Arg Val Val Gly Gly Thr Asp Ala Asp Glu Gly
610                 615                 620 gag tgg ccc tgg cag gta agc ctg cat gct ctg ggc cag ggc cac atc      1920
Glu Trp Pro Trp Gln Val Ser Leu His Ala Leu Gly Gln Gly His Ile
625                 630                 635                 640 tgc ggt gct tcc ctc atc tct ccc aac tgg ctg gtc tct gcc gca cac      1968
Cys Gly Ala Ser Leu Ile Ser Pro Asn Trp Leu Val Ser Ala Ala His
                645                 650                 655 tgc tac atc gat gac aga gga ttc agg tac tca gac ccc acg cag tgg      2016
Cys Tyr Ile Asp Asp Arg Gly Phe Arg Tyr Ser Asp Pro Thr Gln Trp
                660                 665                 670 acg gcc ttc ctg ggc ttg cac gac cag agc cag cgc agc gcc cct ggg      2064
Thr Ala Phe Leu Gly Leu His Asp Gln Ser Gln Arg Ser Ala Pro Gly
            675                 680                 685 gtg cag gag cgc agg ctc aag cgc atc atc tcc cac ccc ttc ttc aat      2112
Val Gln Glu Arg Arg Leu Lys Arg Ile Ile Ser His Pro Phe Phe Asn
690                 695                 700 gac ttc acc ttc gac tat gac atc gcg ctg ctg gag ctg gag aaa ccg      2160
Asp Phe Thr Phe Asp Tyr Asp Ile Ala Leu Leu Glu Leu Glu Lys Pro
705                 710                 715                 720 gca gag tac agc tcc atg gtg cgg ccc atc tgc ctg ccg gac gcc tcc      2208
Ala Glu Tyr Ser Ser Met Val Arg Pro Ile Cys Leu Pro Asp Ala Ser
                725                 730                 735 cat gtc ttc cct gcc ggc aag gcc atc tgg gtc acg ggc tgg gga cac      2256
His Val Phe Pro Ala Gly Lys Ala Ile Trp Val Thr Gly Trp Gly His
            740                 745                 750 acc cag tat gga ggc act ggc gcg ctg atc ctg caa aag ggt gag atc      2304
Thr Gln Tyr Gly Gly Thr Gly Ala Leu Ile Leu Gln Lys Gly Glu Ile
            755                 760                 765 cgc gtc atc aac cag acc acc tgc gag aac ctc ctg ccg cag cag atc      2352
Arg Val Ile Asn Gln Thr Thr Cys Glu Asn Leu Leu Pro Gln Gln Ile
            770                 775                 780 acg ccg cgc atg atg tgc gtg ggc ttc ctc agc ggc ggc gtg gac tcc      2400
Thr Pro Arg Met Met Cys Val Gly Phe Leu Ser Gly Gly Val Asp Ser
785                 790                 795                 800 tgc cag ggt gat tcc ggg gga ccc ctg tcc agc gtg gag gcg gat ggg      2448
Cys Gln Gly Asp Ser Gly Gly Pro Leu Ser Ser Val Glu Ala Asp Gly
                805                 810                 815 cgg atc ttc cag gcc ggt gtg gtg agc tgg gga gac ggc tgc gct cag      2496
Arg Ile Phe Gln Ala Gly Val Val Ser Trp Gly Asp Gly Cys Ala Gln
            820                 825                 830
```

-continued

```
agg aac aag cca ggc gtg tac aca agg ctc cct ctg ttt cgg gac tgg    2544
Arg Asn Lys Pro Gly Val Tyr Thr Arg Leu Pro Leu Phe Arg Asp Trp
        835                 840                 845 atc aaa gag aac act ggg gta tag                                    2568
Ile Lys Glu Asn Thr Gly Val
850                 855
```

<210> SEQ ID NO 2
<211> LENGTH: 855
<212> TYPE: PRT
<213> ORGANISM: Homo sapiens

<400> SEQUENCE: 2

```
Met Gly Ser Asp Arg Ala Arg Lys Gly Gly Gly Pro Lys Asp Phe
1               5                   10                  15

Gly Ala Gly Leu Lys Tyr Asn Ser Arg His Glu Lys Val Asn Gly Leu
                20                  25                  30

Glu Glu Gly Val Glu Phe Leu Pro Val Asn Asn Val Lys Lys Val Glu
            35                  40                  45

Lys His Gly Pro Gly Arg Trp Val Val Leu Ala Ala Val Leu Ile Gly
        50                  55                  60

Leu Leu Leu Val Leu Leu Gly Ile Gly Phe Leu Val Trp His Leu Gln
65                  70                  75                  80

Tyr Arg Asp Val Arg Val Gln Lys Val Phe Asn Gly Tyr Met Arg Ile
                85                  90                  95

Thr Asn Glu Asn Phe Val Asp Ala Tyr Glu Asn Ser Asn Ser Thr Glu
            100                 105                 110

Phe Val Ser Leu Ala Ser Lys Val Lys Asp Ala Leu Lys Leu Leu Tyr
        115                 120                 125

Ser Gly Val Pro Phe Leu Gly Pro Tyr His Lys Glu Ser Ala Val Thr
130                 135                 140

Ala Phe Ser Glu Gly Ser Val Ile Ala Tyr Tyr Trp Ser Glu Phe Ser
145                 150                 155                 160

Ile Pro Gln His Leu Val Glu Glu Ala Glu Arg Val Met Ala Glu Glu
                165                 170                 175

Arg Val Val Met Leu Pro Pro Arg Ala Arg Ser Leu Lys Ser Phe Val
            180                 185                 190

Val Thr Ser Val Val Ala Phe Pro Thr Asp Ser Lys Thr Val Gln Arg
        195                 200                 205

Thr Gln Asp Asn Ser Cys Ser Phe Gly Leu His Ala Arg Gly Val Glu
210                 215                 220

Leu Met Arg Phe Thr Thr Pro Gly Phe Pro Asp Ser Pro Tyr Pro Ala
225                 230                 235                 240

His Ala Arg Cys Gln Trp Ala Leu Arg Gly Asp Ala Asp Ser Val Leu
                245                 250                 255

Ser Leu Thr Phe Arg Ser Phe Asp Leu Ala Ser Cys Asp Glu Arg Gly
            260                 265                 270

Ser Asp Leu Val Thr Val Tyr Asn Thr Leu Ser Pro Met Glu Pro His
        275                 280                 285

Ala Leu Val Gln Leu Cys Gly Thr Tyr Pro Pro Ser Tyr Asn Leu Thr
290                 295                 300

Phe His Ser Ser Gln Asn Val Leu Leu Ile Thr Leu Ile Thr Asn Thr
305                 310                 315                 320

Glu Arg Arg His Pro Gly Phe Glu Ala Thr Phe Phe Gln Leu Pro Arg
                325                 330                 335
```

```
Met Ser Ser Cys Gly Gly Arg Leu Arg Lys Ala Gln Gly Thr Phe Asn
            340                 345                 350

Ser Pro Tyr Tyr Pro Gly His Tyr Pro Pro Asn Ile Asp Cys Thr Trp
        355                 360                 365

Asn Ile Glu Val Pro Asn Asn Gln His Val Lys Val Arg Phe Lys Phe
    370                 375                 380

Phe Tyr Leu Leu Glu Pro Gly Val Pro Ala Gly Thr Cys Pro Lys Asp
385                 390                 395                 400

Tyr Val Glu Ile Asn Gly Glu Lys Tyr Cys Gly Glu Arg Ser Gln Phe
                405                 410                 415

Val Val Thr Ser Asn Ser Asn Lys Ile Thr Val Arg Phe His Ser Asp
            420                 425                 430

Gln Ser Tyr Thr Asp Thr Gly Phe Leu Ala Glu Tyr Leu Ser Tyr Asp
        435                 440                 445

Ser Ser Asp Pro Cys Pro Gly Gln Phe Thr Cys Arg Thr Gly Arg Cys
    450                 455                 460

Ile Arg Lys Glu Leu Arg Cys Asp Gly Trp Ala Asp Cys Thr Asp His
465                 470                 475                 480

Ser Asp Glu Leu Asn Cys Ser Cys Asp Ala Gly His Gln Phe Thr Cys
                485                 490                 495

Lys Asn Lys Phe Cys Lys Pro Leu Phe Trp Val Cys Asp Ser Val Asn
            500                 505                 510

Asp Cys Gly Asp Asn Ser Asp Glu Gln Gly Cys Ser Cys Pro Ala Gln
        515                 520                 525

Thr Phe Arg Cys Ser Asn Gly Lys Cys Leu Ser Lys Ser Gln Gln Cys
    530                 535                 540

Asn Gly Lys Asp Asp Cys Gly Asp Gly Ser Asp Glu Ala Ser Cys Pro
545                 550                 555                 560

Lys Val Asn Val Val Thr Cys Thr Lys His Thr Tyr Arg Cys Leu Asn
                565                 570                 575

Gly Leu Cys Leu Ser Lys Gly Asn Pro Glu Cys Asp Gly Lys Glu Asp
            580                 585                 590

Cys Ser Asp Gly Ser Asp Glu Lys Asp Cys Asp Cys Gly Leu Arg Ser
        595                 600                 605

Phe Thr Arg Gln Ala Arg Val Val Gly Gly Thr Asp Ala Asp Glu Gly
    610                 615                 620

Glu Trp Pro Trp Gln Val Ser Leu His Ala Leu Gly Gln Gly His Ile
625                 630                 635                 640

Cys Gly Ala Ser Leu Ile Ser Pro Asn Trp Leu Val Ser Ala Ala His
                645                 650                 655

Cys Tyr Ile Asp Asp Arg Gly Phe Arg Tyr Ser Asp Pro Thr Gln Trp
            660                 665                 670

Thr Ala Phe Leu Gly Leu His Asp Gln Ser Gln Arg Ser Ala Pro Gly
        675                 680                 685

Val Gln Glu Arg Arg Leu Lys Arg Ile Ile Ser His Pro Phe Phe Asn
    690                 695                 700

Asp Phe Thr Phe Asp Tyr Asp Ile Ala Leu Leu Glu Leu Glu Lys Pro
705                 710                 715                 720

Ala Glu Tyr Ser Ser Met Val Arg Pro Ile Cys Leu Pro Asp Ala Ser
                725                 730                 735

His Val Phe Pro Ala Gly Lys Ala Ile Trp Val Thr Gly Trp Gly His
            740                 745                 750

Thr Gln Tyr Gly Gly Thr Gly Ala Leu Ile Leu Gln Lys Gly Glu Ile
```

```
              755                 760                 765
Arg Val Ile Asn Gln Thr Thr Cys Glu Asn Leu Leu Pro Gln Gln Ile
    770                 775                 780

Thr Pro Arg Met Met Cys Val Gly Phe Leu Ser Gly Val Asp Ser
785                 790                 795                 800

Cys Gln Gly Asp Ser Gly Gly Pro Leu Ser Ser Val Glu Ala Asp Gly
                805                 810                 815

Arg Ile Phe Gln Ala Gly Val Val Ser Trp Gly Asp Gly Cys Ala Gln
                820                 825                 830

Arg Asn Lys Pro Gly Val Tyr Thr Arg Leu Pro Leu Phe Arg Asp Trp
                835                 840                 845

Ile Lys Glu Asn Thr Gly Val
    850                 855

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
ctaggatgag cagctgtgga                                          20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
aagaatttga agcgcacctt                                          20

<210> SEQ ID NO 5
<211> LENGTH: 255
<212> TYPE: DNA
<213> ORGANISM: Homo sapiens

<400> SEQUENCE: 5
acgtcctgct catcacactg ataaccaaca ctgagcggcg gcatcccggc tttgaggcca    60
ccttcttcca gctgcctagg atgagcagct gtggaggccg cttacgtaaa gcccagggga   120
cattcaacag cccctactac ccaggccact acccacccaa cattgactgc acatggaaca   180
ttgaggtgcc caacaaccag catgtgaagg tgcgcttcaa attcttctac ctgctggagc   240
ccggcgtgcc tgcgg                                                   255

<210> SEQ ID NO 6
<211> LENGTH: 9
<212> TYPE: PRT
<213> ORGANISM: Artificial sequence
<220> FEATURE:
<223> OTHER INFORMATION: Artificial sequence
<220> FEATURE:
<221> NAME/KEY: MISC_FEATURE
<222> LOCATION: (1)..(1)
<223> OTHER INFORMATION: ortho-Aminobenzoic acid (Abz)
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: MISC_FEATURE
```

```
<222> LOCATION: (9)..(9)
<223> OTHER INFORMATION: 3-NO2

<400> SEQUENCE: 6

Xaa Xaa Xaa Arg Gly Leu Phe Gly Tyr
1               5

<210> SEQ ID NO 7
<211> LENGTH: 9
<212> TYPE: PRT
<213> ORGANISM: Artificial sequence
<220> FEATURE:
<223> OTHER INFORMATION: Artificial sequence
<220> FEATURE:
<221> NAME/KEY: MISC_FEATURE
<222> LOCATION: (1)..(1)
<223> OTHER INFORMATION: ortho-Aminobenzoic acid (Abz)
<220> FEATURE:
<221> NAME/KEY: MISC_FEATURE
<222> LOCATION: (9)..(9)
<223> OTHER INFORMATION: 3-NO2

<400> SEQUENCE: 7

Ile Gln Ser Arg Gly Leu Phe Gly Tyr
1               5

<210> SEQ ID NO 8
<211> LENGTH: 9
<212> TYPE: PRT
<213> ORGANISM: Artificial sequence
<220> FEATURE:
<223> OTHER INFORMATION: Artificial sequence
<220> FEATURE:
<221> NAME/KEY: MISC_FEATURE
<222> LOCATION: (1)..(1)
<223> OTHER INFORMATION: ortho-Aminobenzoic acid (Abz)
<220> FEATURE:
<221> NAME/KEY: MISC_FEATURE
<222> LOCATION: (9)..(9)
<223> OTHER INFORMATION: 3-NO2

<400> SEQUENCE: 8

Lys Gln Thr Arg Gly Leu Phe Gly Tyr
1               5
```

MATRIPTASE INHIBITORS AND USES THEREOF AGAINST ORTHOMYXOVIRIDAE INFECTIONS

CROSS REFERENCE TO RELATED APPLICATIONS

This application is a Divisional of U.S. patent application Ser. No. 14/943,716, filed Nov. 17, 2015. U.S. patent application Ser. No. 14/943,716 is a Divisional of U.S. patent application Ser. No. 14/118,768, filed Nov. 19, 2013. U.S. patent application Ser. No. 14/118,768 is the U.S. National Stage Application of International Application PCT/CA2012/050349, filed May 28, 2012, which claims the benefit of U.S. Provisional Application No. 61/492,556, filed Jun. 2, 2011. The entire teachings of the above applications are incorporated herein by reference.

FIELD OF THE INVENTION

The present invention relates to the prevention and/or treatment of orthomyxoviridae infections (e.g., influenza infection).

REFERENCE TO SEQUENCE LISTING

Pursuant to 37 C.F.R. 1.821(c), a sequence listing is submitted herewith as an ASCII compliant text file named 14692_25-Seq Listing_ST25.txt, created on May 23, 2012 and having a size of 22 kilobytes. The content of the aforementioned file is hereby incorporated by reference in its entirety.

BACKGROUND OF THE INVENTION

Influenza—Introduction

Influenza is a highly contagious respiratory disease caused by the influenza virus. Influenza respiratory infections, and particularly influenza A because of its continuous antigenic evolution, have the potential to lead to deadly pandemics (e.g., 1918, 1957 and 1968). In recent history, events such as those of Hong Kong in 1997, SARS in 2003, as well as the transmission of H5N1 avian influenza directly to humans, underscore the scope and severity of the consequences associated to such infections. In fact, according to the WHO there are 3 to 5 million severe cases of influenza each year and 250 000 to 500 000 deaths from the virus.

The influenza virus, which belongs to the orthomyxoviridae family, is enveloped and contains 8 single-stranded RNA segments coding for 10 to 12 proteins. While there are three types of influenza viruses (A, B and C), only types A and B cause significant illnesses in humans, type A viruses being the most problematic. Type A influenza viruses are responsible for most of the seasonal epidemics and are further subtyped according to surface glycoproteins: hemagglutinin (HA) and neuraminidase (NA). The influenza virus evades the host immune system by undergoing a continuous antigenic evolution through the processes called antigenic « drift » and « shift ». Antigenic drift is the evolution of viral strains through frequent mutations among antibody binding sites of surface antigens leading to the emergence of new variants not adequately recognized by the host immune system. Antigenic drift is the reason why, every season, it is necessary to identify and predict the most probable strains that will circulate in order to produce the most appropriate vaccines for annual vaccinations. Antigenic shift results from the reassortment of the genetic material of co-circulating strains, leading to the replacement of surface glycoproteins HA, and less frequently NA, which in turn leads to the emergence of severe epidemics and even pandemics (1). Such a scenario is possible for the H5N1 avian virus which has a 50-60% death rate and the H5 component of which has never circulated in the human population. Because new viruses generated through antigenic shift also undergo antigenic drift, this means that in the case of the H5N1 virus, this could lead to efficient transmission from human to human and thus to a pandemic.

Unlike surface antigens, the internal proteins of the virus do not sustain the same mutational pressures and remain more conserved between strains. During the host adaptive cellular immune response, CD8 T cells eliminate infected epithelial cells through a process that involves perforin, granzymes, and cytokines such as TNF-$\alpha$ and IFN$\gamma$. Although it does not provide sterilizing immunity, as does the humoral response, the cellular response significantly reduces lung viral titers. In addition, as opposed to the humoral response which is ineffective against viruses bearing mutated surface antigens, the cellular response recognizes internal epitopes which tend to be conserved between viral strains. It has been shown both experimentally and clinically that the influenza virus easily evades the host humoral response to its surface antigens thanks to its particular mutational characteristics.

Two classes of anti-influenza drugs are currently available: inhibitors of the viral M2 channel (e.g., amantadine and rimantadine) and inhibitors of the viral neuraminidase (e.g., zanamivir and oseltamivir) (2). Inhibitors of the viral M2 channel interact directly with the viral M2 ionic channel which participates in the acidification and the decapsulation of the virus in cellular endosomes, and the viral neuraminidase allow the detachment of nascent virions. Targeting viral proteins has proven to be an effective strategy. However, because of the mutational characteristics of the influenza virus and the widespread use of antiviral drugs, resistance has become an important problem (2, 3). As a result, inhibitors of the M2 ion channel are no longer recommended for the prophylactic treatment of influenza. Furthermore, according to the Center for Disease Control, almost all currently circulating strains of H3N2 influenza A are resistant to amantadine and almost all circulating H1N1 influenza A seasonal strains are resistant to oseltamivir (Tamiflu™). Fortunately, most H1N1 influenza A strains stemming from the 2009 pandemic are susceptible to the drug, although several resistant strains of this virus have been isolated. Therefore, targeting host cellular mechanisms that are crucial for influenza viral entry, protein synthesis, maturation, and replication, provides an exciting alternative strategy potentially obviating the resistance problem.

Hemagglutinin (HA) protein plays an essential role in binding to and entering into host cells during the virus infection process. Hemagglutinin (HA) binds to monosaccharide sialic acids that are present on the surface of its target host cells. The cell membrane then engulfs the virus through endocytosis and forms endosomes. The binding affinity of a type of influenza virus to sialic acids on epithelial cells of the respiratory system, typically in the nose, pharynx, trachea, bronchi, bronchioles, alveoli and lungs of mammals and intestines of birds, can affect the capability of the virus to infect the species and the capability to spread among different individuals.

Influenza HA is synthesized as a single protein precursor termed HA0 and since the virus does not encode any protease, host cell proteases are required for the cleavage of HA0 into subunits HA1 and HA2. This cleavage is required for the protein to change conformation in the acidic conditions in the endosome (9, 10). This change in the protein's conformation exposes the hydrophobic fusion peptide located in the HA2 subunit (11, 12). This allows the virus to fuse with the host cell. The hemagglutinin proteins of pathogenic avian influenza viruses are characterized by multibasic cleavage sites containing furin-like recognition sequences RXXR (13, 14). Since some subtilisin-like proteases such as furin or other proprotein convertases are ubiquitous, the HA glycoprotein of avian viruses utilizes multiple tissues and sites for its activation and allows infection and replication of these viruses in many cell types (pantropicity) (14). One of the severe manifestations of avian flu virus is a life-threatening encephalitis. On the other hand, the HA glycoprotein of non-avian viruses does not have the polybasic furin-recognition site. These viruses have monobasic cleavage sites recognized by other proteases (e.g., TTSPs) of the host (14).

The present description refers to a number of documents, the content of which is herein incorporated by reference in their entirety.

SUMMARY OF THE INVENTION

In the studies described herein, the inventors have shown that the type II transmembrane protease matriptase (also known as ST14 or TMPRSS14) is capable of cleaving and activating influenza HA. Matriptase mRNA was identified in several human respiratory system epithelial cells as well as in a RNA extract from healthy human lungs. Furthermore, the inventors have demonstrated that the matriptase protein is expressed in human epithelial cell lines of the respiratory system. Adding matriptase to Mandin-Darby Canine Kidney (MDCK) cells, (which do not allow multicycle influenza replication without an exogenous protease such as trypsin), promotes viral plaque formation, thereby indicating that matriptase is able to activate HA and promotes multicycle influenza replication in these cells. In addition, using RNA interference technology it was shown that siRNAs targeting matriptase significantly blocks influenza replication in a human epithelial cell line that can promote influenza replication without exogenous enzyme addition. Furthermore, the inventors have generated a class of selective potent matriptase inhibitors possessing a "serine trap" (e.g., a ketobenzothiazole moiety) which block matriptase activity thereby inhibiting HA activation and influenza replication in human airway epithelial cells.

In accordance with a first aspect of the present invention, there is provided a compound of formula (1):

(1)

or a pharmaceutically acceptable salt, hydrate, solvate, or stereoisomer thereof, wherein $R_{12}$ is H, $NH_2$ or $NHR_7$; wherein $R_7$ is an alkyl, aryl, (C=O)-alkyl, (C=O)-aryl, $SO_2$-alkyl, $SO_2$-aryl, C(=NH)—$NH_2$, C(=NH)—NHalkyl, C(=NH)—NHaryl, or one or more amino acids residues;

$R_{13}$ is H, $NH_2$ or $NHR_7$; wherein $R_7$ is an alkyl, aryl, (C=O)-alkyl, (C=O)-aryl, $SO_2$-alkyl or $SO_2$-aryl, C(=NH)—$NH_2$, C(=NH)—NHalkyl, C(=NH)—NHaryl or one or more amino acids residues;

$R_1$ is H, $NH_2$ or $NHR_7$; wherein $R_7$ is an alkyl, aryl, (C=O)-alkyl, (C=O)-aryl, $SO_2$-alkyl or $SO_2$-aryl, C(=NH)—$NH_2$, C(=NH)—NHalkyl, C(=NH)—NHaryl or one or more amino acids residues;

$R_2$ and $R_5$ are independently —$CH_2$—$R_8$ or wherein $R_8$ is $(CH_2)n$-NH(C=NH)NH—$R_{14}$ or $(CH_2)n$-NH—$R_{14}$, wherein, n is 1 to 4;

m is 0 to 3;

$R_{10}$ is —C(=NH)—$NH_2$, $NH_2$ or NH alkyl; and $R_{14}$ is H, alkyl, $NH_2$, $NO_2$ or COalkyl;

$R_3$ and $R_4$ are independently an alkyl, an aryl, a substituted alkyl, a substituted aryl, an heteroaryl, a substituted heteroaryl, a side chain of an amino acid or a substituted side chain of an amino acid;

$R_6$ is $CF_3$, $CO_2H$, $CONH_2$, CONH-alkyl, CONH-aryl or CO-(amino acid residue)$_p$, wherein p is 1 to 3;

wherein W, X, Y and Z are independently N or CH;

V and U are independently O, NH, $NCH_3$ or S; and $R_{11}$ is H, $CO_2H$, CONH-alkyl, CONH-aryl, aryl, heteroaryl, halide or CO-(amino acid residue)$_q$, wherein q is 1 or 2.

In a specific embodiment, $R_7$ is

In another specific embodiment,
R₇ is

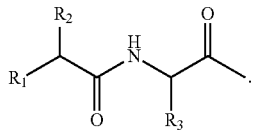

In another specific embodiment,
(i) R₁ is —H or —NH₂;
(ii) R₂ is

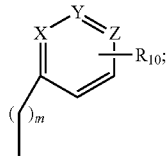

(iii) m is 1;
(iv) W is CH;
(v) X is CH;
(vi) Y is CH;
(vii) R₁₀ is —C(=NH)NH₂; or
(viii) any combination of (i) to (vii).
In another specific embodiment,
(i) R₁ is —NH₂;
(ii) R₂ is —CH₂—R₈;
(iii) R₃ is a substituted alkyl;
(iv) R₄ is an alkyl;
(v) R₅ is —CH₂—R₈;
(V) R₆ is

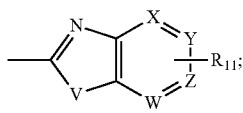

(vi) R₈ is —(CH₂)₃NH(C=NH)NH₂;
(vii) W is CH;
(viii) X is CH;
(ix) Y is CH;
(x) Z is CH;
(xi) V is S;
(xii) R₁₁ is H; or
(xiii) any combination of (i) to (xii).
In another specific embodiment, R₃ is a substituted alkyl, which is substituted with an alkyl, aryl, (CO)NH₂, (CO)OH, NH₂, NHCO-alkyl, NHCO-aryl, NHSO₂-alkyl, NHSO₂-aryl or heteroaryl. In another specific embodiment, R₃ is a substituted C₁ to C₆ alkyl. In another specific embodiment, R₃ is a substituted C₁ to C₃ alkyl. In another specific embodiment, R₃ is —(CH₂)₂C(=O)NH₂. In another specific embodiment, R₄ is a C₁ to C₆ alkyl. In another specific embodiment, R₄ is a C₁ to C₃ alkyl. In another specific embodiment, R₄ is —CH₃. In another specific embodiment, R₂ and R₅ have the (S) configuration.
In another specific embodiment, the compound is of formula (1.1):

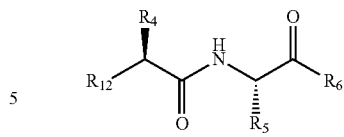

wherein
R₁₂ is H, NH₂ or NHR₇, wherein R₇ is an alkyl, aryl, (C=O)-alkyl, (C=O)-aryl, SO₂-alkyl, SO₂-aryl, and

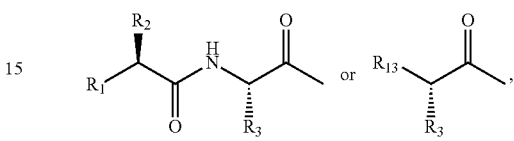

wherein R₁, R₂, R₃, R₄, R₅, R₆, R₈, R₁₀, R₁₁ and R₁₃ are as defined in any one of claims 1 to 13.
In another specific embodiment, R₇ is

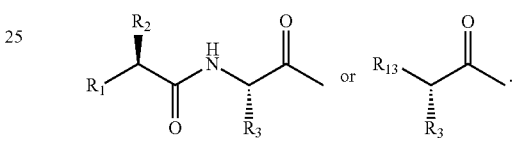

In another specific embodiment, R₇ is

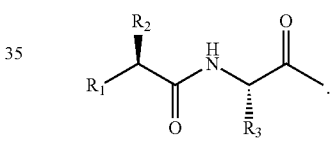

In another specific embodiment, R₁₂ is NH₂,

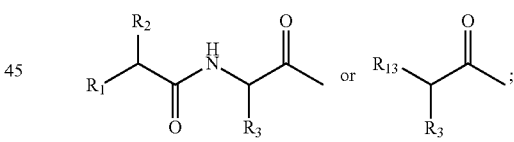

R₁₃ is NH₂;
R₁ is NH₂;
R₂ is the side chain of arginine;
R₅ is the side chain of arginine or lysine;
R₃ is the side chain of glutamine;
R₄ is the side chain of alanine;
R₆ is

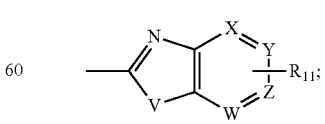

wherein W, X, Y and Z are CH; and V is S; and
R₁₁ is H.
In another specific embodiment, the compound is of formula (3):

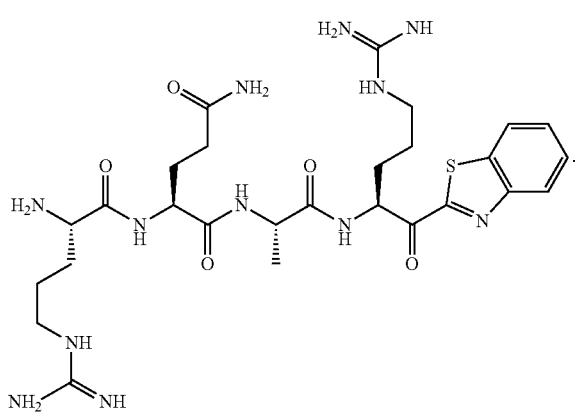

(3)

In accordance with another aspect of the present invention, there is provided a composition comprising the compound of the present invention, and
- (a) a further therapeutic agent for treating or preventing an orthomyxovirus infection and/or associated symptoms;
- (b) a pharmaceutically acceptable excipient; or
- (c) a combination of (a) and (b).

In a specific embodiment, said orthomyxovirus infection is an influenza infection.

In another specific embodiment, said further therapeutic agent is a viral M2 ion channel inhibitor or a neuraminidase inhibitor.

In another specific embodiment, said further therapeutic agent is Tamiflu™ (oseltamivir), Relenza™ (zanamivir), laninamivir, peramivir, amantadine, rimantadine, ribavirin vitamin C, Cold Fx™, echinacea, ginseng or any combination thereof.

In another specific embodiment, the composition is formulated for direct administration into lungs.

In another specific embodiment, the composition is for administration by an inhaler or nebulizer.

In accordance with another aspect of the present invention, there is provided a method of preventing or treating an orthomyxovirus infection in a subject, said method comprising administering to said subject a therapeutically effective amount of a matriptase inhibitor, or a composition comprising said inhibitor, to said subject.

In a specific embodiment of the method, said matriptase inhibitor is a compound is a composition as defined herein.

In another specific embodiment, said composition is a composition as defined herein.

In another specific embodiment, said matriptase inhibitor is one or more of the compounds depicted in Tables 2 to 6.

In another specific embodiment, said matriptase inhibitor is an antibody specifically recognizing the catalytic domain of matriptase. In another specific embodiment, said antibody specifically recognizing the catalytic domain of matriptase comprises the sequence of the light and/or heavy chain CDR1, CDR2 and CDR3 defined in Table 1. In another specific embodiment, said antibody specifically recognizing the catalytic domain of matriptase comprises the sequence of the light and/or heavy chain defined in Table 1. In another specific embodiment, said matriptase inhibitor is an RNA interference agent that decreases the expression of matriptase. In another specific embodiment, wherein said RNA interference agent is an siRNA.

In another specific embodiment, the orthomyxovirus infection is an influenza infection. In another specific embodiment, the influenza infection is an influenza type A infection.

In accordance with another aspect of the present invention, there is provided a method of inhibiting matriptase activity in a cell, comprising contacting the cell with an effective amount of: (i) a compound as defined herein; or (ii) a composition as defined herein; whereby said matriptase activity is inhibited. In a specific embodiment, said cell is an epithelial cell of the respiratory system.

In accordance with another aspect of the present invention, there is provided a use of a matriptase inhibitor, or a composition comprising said inhibitor, for treating or preventing an orthomyxovirus infection in a subject.

In accordance with another aspect of the present invention, there is provided a use of a matriptase inhibitor, or a composition comprising said inhibitor, for the manufacture of a medicament for treating or preventing an orthomyxovirus infection in a subject.

In a specific embodiment, said matriptase inhibitor is a compound as defined herein. In another specific embodiment, said composition or medicament is a composition as defined herein. In another specific embodiment, said matriptase inhibitor is one or more of the compounds depicted in Tables 2 to 6. In another specific embodiment, said matriptase inhibitor is an antibody specifically recognizing the catalytic domain of matriptase. In another specific embodiment, said antibody specifically recognizing the catalytic domain of matriptase comprises the sequence of the light and/or heavy chain CDR1, CDR2 and CDR3 defined in Table 1. In another specific embodiment, said antibody specifically recognizing the catalytic domain of matriptase comprises the sequence of the light and/or heavy chain defined in Table 1. In another specific embodiment, said matriptase inhibitor is an RNA interference agent that decreases the expression of matriptase. In another specific embodiment, said RNA interference agent is an siRNA. In another specific embodiment, the orthomyxovirus infection is an influenza infection. In another specific embodiment, the influenza infection is an influenza type A infection.

In accordance with another aspect of the present invention, there is provided a use of (i) a compound as defined herein; or (ii) a composition as defined herein, for inhibiting matriptase activity in a cell.

In accordance with another aspect of the present invention, there is provided a use of (i) a compound as defined herein; or (ii) a composition as defined herein, for the manufacture of a medicament for inhibiting matriptase activity in a cell. In a specific embodiment, said cell is an epithelial cell of the respiratory system.

In accordance with another aspect of the present invention, there is provided a matriptase inhibitor, or a composition comprising said inhibitor, for treating or preventing an orthomyxovirus infection in a cell.

In accordance with another aspect of the present invention, there is provided a matriptase inhibitor, or a composition comprising said inhibitor, for the manufacture of a medicament for treating or preventing an orthomyxovirus infection in a cell. In a specific embodiment, said matriptase inhibitor is a compound as defined herein. In another specific embodiment, said composition or medicament is a composition as defined herein. In another specific embodiment, said matriptase inhibitor is one or more of the compounds depicted in Tables 2 to 6. In another specific embodiment, said matriptase inhibitor is an antibody specifically recognizing the catalytic domain of matriptase. In another specific embodiment, said antibody specifically recognizing the catalytic domain of matriptase comprises the sequence of the light and/or heavy chain CDR1, CDR2 and CDR3 defined in Table 1. In another specific embodiment, said antibody specifically recognizing the catalytic domain of matriptase comprises the sequence of the light and/or heavy chain defined in Table 1. In another specific embodiment, said matriptase inhibitor is an RNA interference agent that decreases the expression of matriptase. In another specific embodiment, said RNA interference agent is an siRNA. In another specific embodiment, the orthomyxovirus infection is an influenza infection. In another specific embodiment, the influenza infection is an influenza type A infection.

In accordance with another aspect of the present invention, there is provided a compound as defined herein, or the composition as defined herein, for inhibiting matriptase activity in a cell.

In accordance with another aspect of the present invention, there is provided a compound as defined herein, or a composition as defined herein, for the manufacture of a medicament for inhibiting matriptase activity in a cell. In a specific embodiment, said cell is an epithelial cell of the respiratory system.

In accordance with another aspect of the present invention, there is provided a kit comprising a matriptase inhibitor, or a composition comprising said inhibitor, and instructions to use same for treating or preventing an orthomyxovirus infection in a subject. In another specific embodiment, said matriptase inhibitor or composition is the matriptase inhibitor or composition as defined herein. In another specific embodiment, the orthomyxovirus infection is an influenza infection. In another specific embodiment, the influenza infection is an influenza type A infection.

In accordance with another aspect of the present invention, there is provided a method for inhibiting tumor growth, progression and/or metastasis in a subject in need thereof, the method comprising administering an effective amount of a compound as defined herein, or a composition a compound as defined herein, to said subject.

In accordance with another aspect of the present invention, there is provided a use of a compound as defined herein, or a composition as defined herein, for inhibiting tumor growth, progression and/or metastasis in a subject.

In accordance with another aspect of the present invention, there is provided a use of the compound of any one of claims 1 to 18, or the composition of any one of claims 19 to 24, for the manufacture of a medicament for inhibiting tumor growth, progression and/or metastasis in a subject In accordance with another aspect of the present invention, there is provided a compound as defined herein, or a composition as defined herein, for inhibiting tumor growth, progression and/or metastasis in a subject.

In accordance with another aspect of the present invention, there is provided a compound as defined herein, or a composition as defined herein, for the manufacture of a medicament for inhibiting tumor growth, progression and/or metastasis in a subject.

In accordance with another aspect of the present invention, there is provided a composition comprising the compound of the present invention, and (a) a further therapeutic agent for treating or preventing flu infections and/or associated symptoms; (b) a pharmaceutically acceptable excipient; or (c) a combination of (a) and (b).

In a specific embodiment of the composition of the present invention, said further therapeutic agent is a viral M2 ion channel inhibitor or a neuraminidase inhibitor. In another specific embodiment of the composition of the present invention, said further therapeutic agent is Tamiflu™ (oseltamivir), Relenza™ (zanamivir), laninamivir, peramivir, amantadine, rimantadine, ribavirin, vitamin C, Cold Fx™, echinacea, ginseng or any combination thereof.

In another specific embodiment of the composition of the present invention, the composition is formulated for direct administration into lungs. In another specific embodiment of the composition of the present invention, the composition is formulated for administration by an inhaler or nebulizer.

In accordance with a further aspect of the present invention, there is provided a method of preventing or treating an orthomyxovirus infection in a subject, said method comprising administering to said subject a therapeutically effective amount of: (i) the compound of the present invention; (ii) the composition of the present invention; or (iii) an siRNA that decreases the expression of matriptase, whereby said flu infection is prevented or treated.

In a specific embodiment of the method of the present invention, the orthomyxovirus infection is an influenza infection. In another specific embodiment of the method of the present invention, the influenza infection is an influenza type A infection.

In accordance with a further aspect of the present invention, there is provided a method of inhibiting matriptase activity in a cell, comprising contacting the cell with an effective amount of: (i) the compound of the present invention; (ii) the composition of the present invention; or (iii) a short interfering RNA molecule (siRNA) that decreases the expression of matriptase, whereby said matriptase activity is inhibited.

In a specific embodiment of the method of the present invention, said cell is an epithelial cell of the respiratory system.

In accordance with a further aspect of the present invention, there is provided a use of: (i) the compound of the present invention; (ii) the composition of the present invention; or (iii) a short interfering RNA molecule (siRNA) that decreases the expression of matriptase, for (a) treating or preventing an orthomyxovirus infection; or (b) inhibiting matriptase activity in a cell.

In accordance with a further aspect of the present invention, there is provided a use of: (i) the compound of the present invention; (ii) the composition of the present invention; or (iii) a short interfering RNA molecule (siRNA) that decreases the expression of matriptase, in the preparation of a medicament for (a) treating or preventing an orthomyxovirus infection; or (b) inhibiting matriptase activity in a cell.

In a specific embodiment of the use of the present invention, the orthomyxovirus infection is an influenza infection. In another specific embodiment of the use of the present invention, the influenza infection is an influenza type A infection.

In another specific embodiment of the use of the present invention, said cell is an epithelial cell of the respiratory system.

In accordance with a further aspect of the present invention, there is provided a compound of the present invention or a composition of the present invention or a short interfering RNA molecule (siRNA) that decreases the expression of matriptase, for (a) treating or preventing an orthomyxovirus infection; or (b) inhibiting matriptase activity in a cell.

In a specific embodiment of the compound, composition or siRNA of the present invention, the orthomyxovirus infection is an influenza infection. In another specific embodiment of the compound, composition or siRNA of the present invention, the influenza infection is an influenza type A infection. In another specific embodiment of the compound, composition or siRNA of the present invention, said cell is an epithelial cell of the respiratory system.

In accordance with a further aspect of the present invention, there is provided a kit comprising: (i) the compound of the present invention; (ii) the composition of the present invention; or (iii) a short interfering RNA molecule (siRNA) that decreases the expression of matriptase, and instructions to use same for (a) treating or preventing an orthomyxovirus infection; or (b) inhibiting matriptase activity in a cell.

In a specific embodiment of the kit of the present invention, the orthomyxovirus infection is an influenza infection. In another specific embodiment of the kit of the present invention, the influenza infection is an influenza type A infection. In another specific embodiment of the kit of the present invention, said cell is an epithelial cell of the respiratory system.

In a specific embodiment of the method, the use, the compound for use, composition for use or siRNA for use, or kit of the present invention, the influenza infection is cause by a type A virus. In a specific embodiment of the method, the use, the compound for use, composition for use or siRNA for use, or kit of the present invention, the influenza infection is cause by a type B virus. In a specific embodiment of the method, the use, the compound for use, composition for use or siRNA for use, or kit of the present invention, the influenza infection is cause by a type C virus.

In another aspect, the present invention relates to a composition having formula (1), (1.1) or (1.2) for the prevention or treatment of influenza infection. In an embodiment, the composition further comprises a pharmaceutically acceptable excipient. In an embodiment, the composition inhibits hemagglutinin activation. In an embodiment, the composition inhibits sustained viral replication and propagation. In an embodiment the composition reduces viral load/titre in an infected subject's blood, cells or in a nasopharingeal swab of that subject. In an embodiment, the cells are epithelial cells of the respiratory system (e.g., nasal, of the pharynx, tracheal, bronchial, bronchiolar, alveolar and lung epithelial cell).

In a further aspect, the present invention concerns a method of treating or preventing an orthomyxovirus infection in a subject in need thereof comprising administering an effective amount of i) a compound or composition of the present invention comprising a matriptase inhibitor of the present invention or ii) a short interfering RNA molecule (siRNA) that decreases the expression of matriptase. In an embodiment, the inhibitor is that of formula (1). In a further embodiment, the inhibitor is that of formula (1.1). In a further embodiment, the inhibitor is that of formula (1.2).

Accordingly, the composition of the present invention may comprise additional products for preventing or treating any symptoms of an orthomyxovirus infection (e.g., influenza) (e.g., antitussif, expectorant, anti-inflammatory analgesic, decongestant) or may be used in combination with any additional flu medicine. Non-limiting examples of additional flu medicine include viral M2 ion channel inhibitors and neuraminidase inhibitors. Known therapeutic agents for the prevention and treatment of flu infections includes Tamiflu™ (oseltamivir), Relenza™ (zanamivir), laninamivir, peramivir, amantadine, rimantadine, ribavirin, vitamin C, Cold Fx™, echinacea, ginseng, etc. In another particular embodiment, the composition of the present invention comprises as sole medicinal ingredient for the prevention or treatment of flu infection a composition comprising the compound of formula (1), (1.1), (1.2), (2), (2.1) or (3).

The present invention also provides a method of inhibiting matriptase activity in a cell comprising contacting the cell with an effective amount of (i) a compound of the present invention; (ii) a composition comprising a compound of the present invention or (iii) a short interfering RNA molecule (siRNA) that decreases the expression of matriptase, whereby matriptase activity is inhibited. In an embodiment, the inhibitor is that of formula (1). In another embodiment, the inhibitor is that of formula (1.1). In another embodiment, the inhibitor is that of formula (1.2). In another embodiment, the inhibitor is that of formula (2). In another embodiment, the inhibitor is that of formula (2.1). In another embodiment, the inhibitor is that of formula (3).

In another aspect, the present invention is concerned with a method of inhibiting influenza infection in a cell comprising contacting the cell with an effective amount of (i) a compound of the present invention; (ii) a composition comprising a compound of the present invention; or (iii) a short interfering RNA molecule (siRNA) that decreases the expression of matriptase, whereby influenza infection is inhibited. In an embodiment, the inhibitor is that of formula (1). In another embodiment, the inhibitor is that of formula (1.1). In another embodiment, the inhibitor is that of formula (1.2). In another embodiment, the inhibitor is that of formula (2). In another embodiment, the inhibitor is that of formula (2.1). In another embodiment, the inhibitor is that of formula (3).

The present invention also relates to the use of (i) a compound of the present invention; (ii) a composition comprising a compound of the present invention; or (iii) a short interfering RNA molecule (siRNA) that decreases the expression of matriptase, for (a) treating or preventing an orthomyxovirus infection; or (b) inhibiting matriptase activity in a cell.

The present invention also relates to the use of (i) a compound of the present invention; (ii) a composition comprising a compound of the present invention; or (iii) a short interfering RNA molecule (siRNA) that decreases the expression of matriptase for the manufacture of a medicament for the prevention or treatment of flu infections.

In another aspect, the present invention relates to the use of the compound or compositions of the present invention for research assays (e.g., biochemical, enzymatic assays, in vitro or in vivo models).

The compositions of the present invention comprising an inhibitor or RNAi or antibody of the present invention may be formulated in various ways according to the route of administration. The compositions or RNAis of the present invention may be administered in any suitable way including for example orally, nasally or topically. Administration is carried out in a customary manner, preferably directly to the lung of the subject (e.g., via a nebulizer or an inhaler).

Other and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIGS. 1A and 1B show the matriptase nucleotide sequence (SEQ ID NO:1); and protein sequence (SEQ ID NO:2), respectively.

FIG. 7 shows that matriptase promotes multicycle influenza replication in MDCK cells infected with 25 PFU of A/Puerto Rico/8/34 influenza virus (PR8). Panel A: Recombinant matriptase (43 nM) was added to MDCK cells and cells were infected with 25 PFU of A/Puerto Rico/8/34 influenza virus (PR8). Viral plaques are observed in the presence of matriptase (or trypsin the standard protease used in this assay) thereby indicating viral activation by the enzyme. Compared to trypsin, matriptase was approx. 80% as effective in viral plaque initiation. Panel B: Compilation of results and efficacy of IN-1 (Compound 1) at inhibiting matriptase in this assay (no effect on trypsin indicating selectivity). Panel C: Concentration-response curve of inhibition of PR8 plaque formation in the presence of IN-1 in MDCK cells supplemented with Matriptase (43 nM). Viral plaques are observed in the presence of matriptase (or trypsin) thereby indicating viral activation by the enzyme.

FIG. 8 shows that siRNAs targeting matriptase mRNA significantly block matriptase protein expression. Calu-3 cells were transfected with two different siRNAs (50 nmol) targeted toward matriptase mRNA using various concentrations of Lipofectamine RNAiMAX™ (0.5 to 1.5 µl). Scrambled siRNAs were used as controls. Panel A: Western blot of total protein extracts from Calu-3 cells. Matriptase was identified using a rabbit anti-human ST14 (matriptase) antibody. S: transfected scrambled siRNA control; 1: transfected siRNA 1 targeted to matriptase; 2: transfected siRNA 2 targeted to matriptase; Ctrl untransfected cells. Densitometric analysis of siRNA knock-down of matriptase protein expression in Calu-3 cells. Panel B: Densitometric analysis of blots performed in (A) revealed that matriptase-targeted siRNAs significantly inhibited matriptase protein expression in Calu-3 cells 48 h after transfection.

FIG. 11A reports the dissociation curves for ketobenzothiazole inhibitor IN-1 and FIG. 11B reports the dissociation curves for irreversible inhibitor Glu-Gly-Arg chloromethyl ketone (EGR-CMK). Matriptase and increasing concentrations of (A) RQAR-ketobenzothiazole (IN-1, compound 1 in Table 7) or (B) EGR-CMK were pre-incubated for 20 minutes at room temperature and diluted 2000 times in a reaction buffer containing 400 µM Boc-QAR-AMC. Final concentration of matriptase was 0.25 nM and was varied as indicated for inhibitors. Proteolytic activity in the reaction buffer was measured as described below.

FIG. 13A shows the inhibition of the enzymatic activity of various proteases (1 nM) by compound IN-1 (1 µM). Data is presented as relative activity compared to the control reaction (vehicle=1) (white columns). FIGS. 13B and 13C show the $IC_{50}$ determination of IN-1 for matriptase (B) and hepsin (C), respectively. Relative activities (Vi/Vo) were plotted as a function of the log transformation of inhibitor concentration (log I). Data were fitted by non-linear regression analysis using GraphPad™ Prism 5 software. $IC_{50}$ corresponds to the concentration of inhibitor that results in a response half way between the maximal response and the maximal inhibitory response.

DESCRIPTION OF ILLUSTRATIVE EMBODIMENTS

Figure 2:
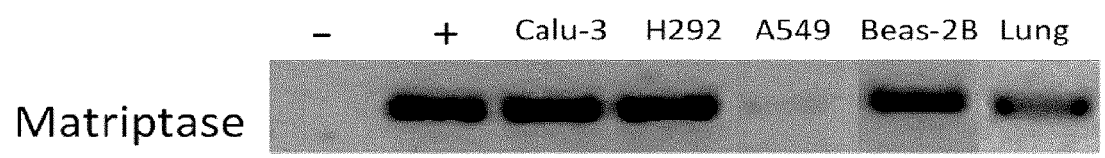
FIG. 2 shows matriptase mRNA expression in human respiratory system epithelial cell lines (Calu-3, H292, A549, Beas-2B) and in an RNA extract from normal human lung (Lung; Ambion).

The results presented herein show for the first time that matriptase, a type II transmembrane serine protease, is expressed in epithelial cells of the respiratory system both at the mRNA and protein levels. Moreover, the inventors have discovered that matriptase is capable of promoting multi-cycle influenza replication both in a system where an exogenous protease is required for influenza hemagglutinin activation and in a system where the cells possess all of the required enzymes to activate the influenza virus. Further, results confirmed that matriptase is involved in influenza replication in airway epithelial cells through inhibition assays using new inhibitors as well as in a siRNA knock-down system targeting matriptase. Finally, the results presented herein show that matriptase inhibitors are effective at blocking influenza replication in vitro and that these show selectivity for matriptase.

The matriptase inhibitors described target the host cell (a host protein) and not the virus directly. It is hypothesized that this may reduce viral adaptation since the viral proteins are not targeted directly, thus obviating continuous viral mutations. Second, since both influenza A and B types require proteolytic cleavage of hemagglutinin for their activation, it is hypothesized that the matriptase inhibitors described herein has a broad spectrum of activity. As the current anti-influenza antivirals (M2 ion channel blockers and neuraminidase inhibitors) exhibit more and more resistance, inhibition of matriptase may be used as first line therapy. Inhibition of matriptase may also be used in combination with other antivirals (e.g., M2 ion channel blockers and neuraminidase inhibitors) in attempts to minimize the generation of escape mutants that lead to antiviral resistance.

The present invention relates to a compound of formula (1):

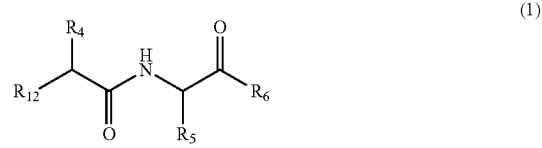

or a pharmaceutically acceptable salt, hydrate, solvate, or stereoisomer thereof, wherein $R_{12}$ is H, $NH_2$ or $NHR_7$; wherein $R_7$ is an alkyl, aryl, (C=O)-alkyl, (C=O)-aryl, $SO_2$-alkyl, $SO_2$-aryl, C(=NH)—$NH_2$, C(=NH)—NHalkyl, C(=NH)—NHaryl,

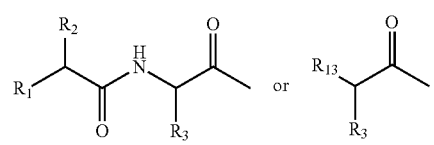

or one or more amino acid residues, in an embodiment 1 to 4 (1, 2, 3 or 4);

$R_{13}$ is H, $NH_2$ or $NHR_7$; wherein $R_7$ is an alkyl, aryl, (C=O)-alkyl, (C=O)-aryl, $SO_2$-alkyl, $SO_2$-aryl, C(=NH)—$NH_2$, C(=NH)—NHalkyl, C(=NH)—NHaryl, or one or more amino acid residues, in an embodiment 1 to 3 (1, 2 or 3);

$R_1$ is H, $NH_2$ or $NHR_7$; wherein $R_7$ is an alkyl, aryl, (C=O)-alkyl, (C=O)-aryl, $SO_2$-alkyl, $SO_2$-aryl C(=NH)—$NH_2$, C(=NH)—NHalkyl, C(=NH)—NHaryl, or one or more amino acid residues, in an embodiment 1 to 3 (1, 2 or 3);

$R_2$ and $R_5$ are independently —$CH_2$—$R_8$ or

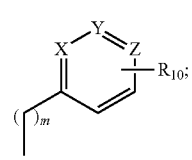

wherein $R_8$ is $(CH_2)n\text{-}NH(C=NH)n\text{-}NH.R_{14}$ or $(CH_2)n\text{-}NH\text{-}R_{14}$, wherein n is 1 to 6, in an embodiment 1 to 4 (1, 2, 3 or 4), in an embodiment 1 to 3 (1, 2 or 3); m is 0 to 6, in an embodiment 0 to 3 (0, 1, 2 or 3); and $R_{10}$ is $-C(=NH)-NH_2$, $NH_2$ or NH alkyl; and $R_{14}$ is H, alkyl, $NH_2$, $NO_2$, COalkyl;

$R_3$ and $R_4$ are independently an alkyl, an aryl, a substituted alkyl or a substituted aryl, a heteroaryl, a substituted heteroaryl, a side chain of an amino acid or a substituted side chain of an amino acid. In an embodiment $R_4$ is the side chain of alanine, valine, isoleucine, leucine, glutamine, alanine, aspartic acid, asparagine, glutamic acid, serine, homoserine, alpha-amino adipic acid, phenylalanine, tyrosine, tryptophan, histidine, pyridylalanine, thienylalanine, thiazolylalanine, furylalanine or naphthylalanine, the side chain being substituted or not; and $R_6$ is a serine trap, in an embodiments $R_6$ is

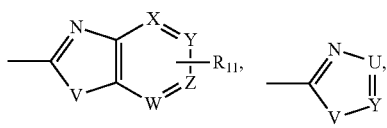

$CF_3$, $CO_2H$, $CONH_2$, CONH-alkyl, CONH-aryl or CO-(amino acid residue)$_p$, wherein p is 1 or more, in a specific embodiment 1 to 6, in a more specific embodiment 1 to 3;

wherein W, X, Y and Z are independently N or CH; V and U are independently O, NH, $NCH_3$ or S;

$R_{11}$ is H, $CO_2H$, CONH-alkyl, CONH-aryl, aryl, heteroaryl, halide or CO-(amino acid residue)$_q$, wherein q is 1 or more, in a specific embodiment 1 to 4, in a more specific embodiment 1 to 2.

The present invention also relates to a compound of formula (2):

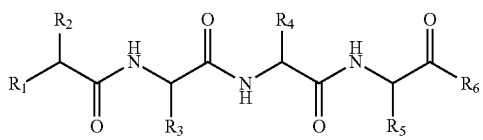

(2)

or a pharmaceutically acceptable salt, hydrate, solvate, or stereoisomer thereof, wherein $R_1$ is H, $NH_2$, $NHR_7$ or one or more amino acid residues; wherein $R_7$ is an alkyl, aryl, $(C=O)$-alkyl, $(C=O)$-aryl, $SO_2$-alkyl or $SO_2$aryl;

$R_2$ and $R_5$ are independently $-CH_2-R_8$ or

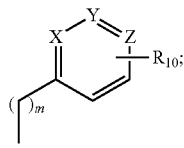

wherein $R_8$ is $(CH_2)n\text{-}NH(C=NH)NH.R_{14}$ or $(CH_2)n\text{-}NH_2$; n is 1 to 3; m is 0 to 3; and $R_{10}$ is $-C(=NH)-NH_2$, $NH_2$ or NH alkyl; $R_{14}$ is H, alkyl, $NH_2$, $NO_2$, COalkyl;

$R_3$ and $R_4$ are independently an alkyl, an aryl, a substituted alkyl or a substituted aryl, a heteroaryl, a substituted heteroaryl, a side chain of an amino acid or a substituted side chain of an amino acid. In an embodiment R4 is the side chain of alanine, valine, isoleucine, leucine, glutamine, alanine, aspartic acid, asparagine, glutamic acid, serine, homoserine, alpha-amino adipic acid, phenylalanine, tyrosine, tryptophan, histidine, pyridylalanine, thienylalanine, thiazolylalanine, furylalanine or naphthylalanine, the side chain being substituted or not; and $R_6$ is

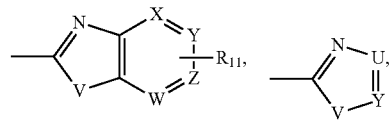

$CF_3$, $CO_2H$, CONH-alkyl, CONH-aryl or CO-(amino acid residue)$_p$, wherein p is 1 or more, in a specific embodiment 1 to 6, in a more specific embodiment 1 to 3; wherein W, X, Y and Z are independently N or CH; V and U are independently O, NH, $NCH_3$ or S; and $R_{11}$ is H, $CO_2H$, CONHalkyl, CONHaryl, aryl, heteroaryl, halide or CO-(amino acid residue)$_q$, wherein q is 1 or more, in an embodiment 1 to 4, in a more specific embodiment 1 to 2.

In an embodiment, $R_{12}$ is H. In another embodiment, $R_{12}$ is $NH_2$. In another embodiment, $R_{12}$ is $NHR_7$.

In an embodiment, $R_7$ is an alkyl (substituted or not). In another embodiment, $R_7$ is an aryl. In another embodiment, $R_7$ is $(C=O)$-alkyl. In another embodiment, $R_7$ is $(C=O)$-aryl. In another embodiment, $R_7$ is $SO_2$-alkyl. In another embodiment, $R_7$ is $SO_2$-aryl. In another embodiment, $R_7$ is.

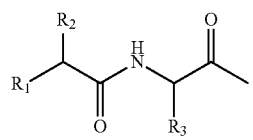

In another embodiment, $R_7$ is

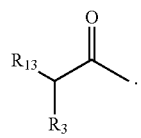

In an embodiment, $R_1$ and/or $R_{13}$ is an alkyl. In another embodiment, $R_1$ and/or $R_{13}$ is an aryl. In another embodiment, $R_1$ and/or $R_{13}$ is $(C=O)$-alkyl. In another embodiment, $R_1$ and/or $R_{13}$ is $(C=O)$-aryl. In another embodiment, R and/or $R_{13}$ is $SO_2$-alkyl. In another embodiment, $R_1$ and/or $R_{13}$ is $SO_2$-aryl.

In an embodiment, $R_2$ and/or $R_5$ is $-CH_2-R_8$. In another embodiment, $R_2$ and/or $R_5$ is

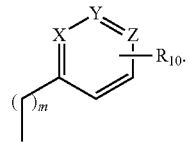

In an embodiment, $R_{10}$ is $-C(=NH)-NH_2$. In another embodiment, $R_{10}$ is $NH_2$. In another embodiment, $R_{10}$ is NH-alkyl.

In an embodiment, $R_3$ and/or $R_4$ is an alkyl. In another embodiment, $R_3$ and/or $R_4$ is an aryl. In another embodiment, $R_3$ and/or $R_4$ is a substituted alkyl. In another embodiment, $R_3$ and/or $R_4$ is a substituted aryl.

In an embodiment, $R_6$ is

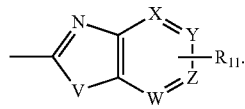

In another embodiment, $R_6$ is

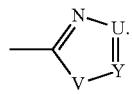

In another embodiment, $R_6$ is $CF_3$. In another embodiment, $R_6$ is $CO_2H$. In another embodiment, $R_6$ is $CONH_2$. In another embodiment, $R_6$ is $CONH$-alkyl. In another embodiment, $R_6$ is $CONH$-aryl. In another embodiment, $R_6$ is CO-(amino acid residue)$_p$, wherein p is 1 or more, in a specific embodiment 1 to 6, in a more specific embodiment 1 to 3.

In an embodiment W, X, Y and/or Z is N. In another embodiment, W, X, Y and/or Z is CH.

In an embodiment, V and/or U is O. In another embodiment, V and/or U is NH. In another embodiment, V and/or U is $NCH_3$. In another embodiment, V and/or U is S.

In an embodiment, $R_{11}$ is H. In another embodiment, $R_{11}$ is $CO_2H$. In another embodiment, $R_{11}$ is CONH-alkyl. In another embodiment, $R_{11}$ is CONH-aryl. In another embodiment, $R_{11}$ is aryl. In another embodiment, $R_{11}$ is heteroaryl. In another embodiment, $R_{11}$ is halide.

In an embodiment, the compound is of formula (1.1):

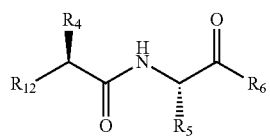

wherein $R_{12}$ is H, $NH_2$ or $NHR_7$, wherein $R_7$ is an alkyl, aryl, (C=O)-alkyl, (C=O)-aryl, $SO_2$-alkyl, $SO_2$-aryl,

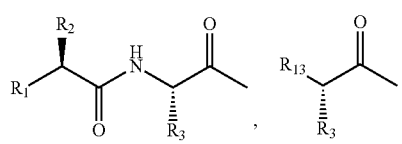

or one or 2 amino acid residue(s); and wherein $R_1$, $R_2$, $R_3$, $R_4$, $R_5$, $R_6$, $R_8$, $R_{10}$, $R_{11}$ and $R_{13}$ are as defined above.

In a specific embodiment, the compound is of formula (2.1):

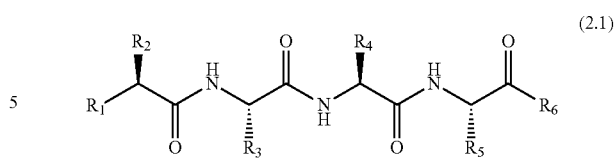

wherein $R_1$, $R_2$, $R_3$, $R_4$, $R_5$ and $R_6$ are as defined above.

In a specific embodiment, the compound is of formula (1.1)

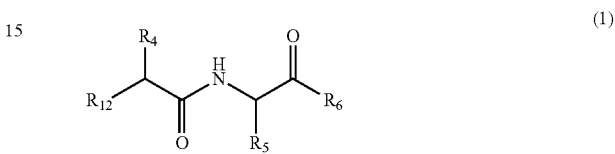

or a pharmaceutically acceptable salt, hydrate, solvate, or stereoisomer thereof, wherein $R_{12}$ is $NH_2$,

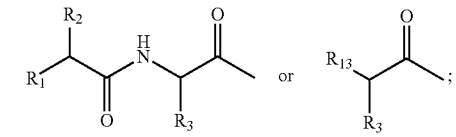

$R_{13}$ is $NH_2$;

$R_1$ is as defined above, or in a specific embodiment, $R_1$ is $NH_2$;

$R_2$ is the side chain of arginine, substituted or not, in an embodiment, not substituted;

$R_5$ is the side chain of arginine or lysine, substituted or not, in an embodiment, not substituted;

$R_3$ is the side chain of glutamine, substituted or not, in an embodiment, not substituted;

$R_4$ is the side chain of alanine, substituted or not, in an embodiment, not substituted;

$R_6$ is

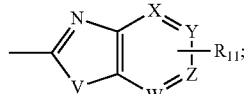

wherein W, X, Y and Z are CH; V is S; and $R_{11}$ is as defined above, in a specific embodiment, $R_{11}$ is H. In a specific embodiment, of the formula 1 as defined above, all amino acid residues are in L-configuration. In a specific embodiment, on amino acid residue is in D configuration. In a specific embodiment, the compound of formula 1 is RQAR-R6, RQAK-R6, QAR-R6 or AR-R6, wherein all amino acids are in L-configuration. In a specific embodiment, the compound of formula 1 is RQAR-R6, wherein A is in D configuration and R, R and R are in L configuration.

In another specific embodiment of the compound of the present invention, (i) $R_1$ is —H or —$NH_2$;

(ii) $R_2$ is

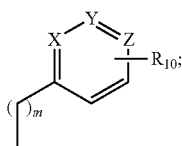

(iii) m is 1; (iv) W is CH; (v) X is CH; (vi) Y is CH; (vii) $R_{10}$ is —C(=NH)NH$_2$; or (viii) any combination of (i) to (vii).

In another specific embodiment of the compound of the present invention, (i) $R_1$ is —NH$_2$; (ii) $R_2$ is —CH$_2$—$R_8$; (iii) $R_3$ is a substituted alkyl; (iv) $R_4$ is an alkyl; (v) $R_5$ is —CH$_2$—$R_8$;
(v) $R_6$ is

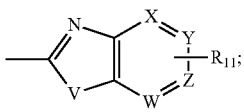

(vi) $R_8$ is —(CH$_2$)$_3$NH(C=NH)NH$_2$ or (CH$_2$)n-NH$_2$, in an embodiment, $R_8$ is —(CH$_2$)$_3$NH(C=NH)NH$_2$; (vii) W is CH; (viii) X is CH; (ix) Y is CH; (x) Z is CH; (xi) V is S; (xii) $R_{11}$ is H; or (xiii) any combination of (i) to (xii).

In another specific embodiment of the compound of the present invention, $R_3$ is substituted alkyl, which is substituted with an alkyl, aryl, (CO)NH$_2$, (CO)OH, NH$_2$, NHCO-alkyl, NHCO-aryl, NHSO$_2$-alkyl, NHSO$_2$-aryl or heteroaryl. In another specific embodiment of the compound of the present invention, $R_3$ is —(CH$_2$)$_2$(C=O)NH$_2$. In another specific embodiment of the compound of the present invention, $R_4$ is —CH$_3$. In another specific embodiment of the compound of the present invention, $R_2$ and $R_5$ have the (S) configuration.

In another specific embodiment of the compound of the present invention, the compound is of formula (3):

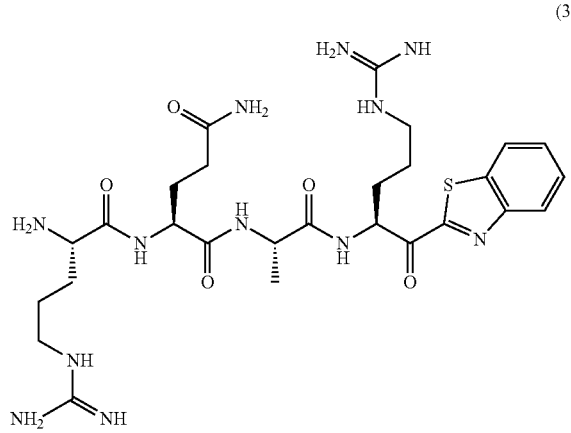

(3)

Definitions

The articles "a," "an" and "the" are used herein to refer to one or to more than one (i.e., to at least one) of the grammatical object of the article.

The use of the word "a" "an" and "the" when used in conjunction with the term "comprising" in the claims and/or the specification may mean "one" but it is also consistent with the meaning of "one or more", "at least one", and "one or more than one".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with, the phrases "including but not limited to" and "comprising but not limited to".

Compound

As used herein, the terms "molecule", "compound" and "agent" are used interchangeably and broadly to refer to natural, synthetic or semi-synthetic molecules or compounds. The term "compound" therefore denotes, for example, chemicals, macromolecules, cell or tissue extracts (from plants or animals) and the like. Non-limiting examples of compounds include peptides, antibodies, carbohydrates, nucleic acid molecules and pharmaceutical agents. The compound can be selected and screened by a variety of means including random screening, rational selection and by rational design using, for example, ligand modeling methods such as computer modeling. As will be understood by the person of ordinary skill, molecules having non-naturally occurring modifications are also within the scope of the term "compound". For example, the compounds of the present invention can be modified to enhance their activity, stability, and/or bioavailability, and also to lower its toxicity. The compounds or molecules identified in accordance with the teachings of the present invention have a therapeutic value in diseases or conditions related to microbial infections, including Orthomyxoviridae infections such as influenza infection.

Compounds of the present invention may include alkyl, aryls, substituted alkyl and substituted aryls.

As used herein the term "alkyl" refers to substituted or unsubstituted, cyclic or acyclic, linear or branched alkyl ($C_1$ to $C_{12}$). In an embodiment, the alkyl is a $C_1$ to $C_{10}$ alkyl, and in a more specific embodiment $C_1$-$C_6$ or $C_1$ to $C_3$. Whenever it appears herein, a numerical range, such as "1 to 12" or "$C_1$-$C_{12}$", refers to each integer in the given range; e.g., "$C_1$-$C_{12}$ alkyl" means that an alkyl group may comprise only 1 carbon atom, 2 carbon atoms, 3 carbon atoms, etc., up to and including 12 carbon atoms, although the term "alkyl" also includes instances where no numerical range of carbon atoms is designated. "Substituted alkyl" refers to alkyl moieties bearing substituents typically selected from alkyl, alkenyl, alkynyl, hydroxy, alkoxy, amide, halide, heterocyclic, aryl, substituted aryl (with substituents on any or all possible aryl positions including but not limited to hydroxyl, amide, halides, nitrile, nitro, alkyl, amino, amides, sulfonamides), guanidine, amidine, heteroaryl, aryloxy, halogen, haloalkyl, cyano, nitro, amino (—NH$_2$), lower alkylamino, lower dialkylamino, amido (—(CO)NR$_6$), azido, acyl (—(CO)R$_6$), alkoxymethyl, mercapto (—S—R$_6$), sulfoxy (—SO—R$_6$), sulfonyl —(SO)$_2$—R$_6$), sulfonamide (—S(O)$_2$N(R$_6$)$_2$), carbonate (—O(CO)—O—R$_6$), oxyacyl (—O(CO)—R$_6$), carboxyl (—CO$_2$H), ester (—(CO)OR$_6$), carbamate (—O(CO)—N(R$_6$)$_2$), wherein R$_6$ is H or lower alkyl, lower alkenyl, lower alkynyl, aryl, heteroaryl, heterocycle, and the like. As used herein, "lower alkyl" refers to alkyl moieties having from 1 to about 6 carbon atoms, for example from 1 to 3 carbon atoms. More preferably, the substituent is an alkyl, aryl, —(CO)NH$_2$, —(CO)OH, —NH$_2$, NHCOalkyl, NHCOaryl, NHSO$_2$alkyl, NHSO$_2$aryl and heteroaryl, guanidine, amidine, halide, OH, OCH$_3$, NO$_2$, NH$_2$ or CO$_2$H. Alkyl, aryl, substituted alkyl and substituted aryl as used herein include the side chains of natural and non-natural amino acids. Hence, in specific embodiments, R$_2$, R$_3$, R$_4$ and/or R$_5$ are side chains of natural/standard or non-natural/non-standard amino acids. In an embodiment, R$_2$ and/or R$_5$ is a side chain of arginine, lysine, histidine or an analog/surrogate thereof such as omithine or citrulline. In an embodiment, R$_4$ is a side chain of alanine, valine, isoleucine, leucine, or an analog/surrogate thereof. In an embodiment, R$_4$ is a side chain of glutamine, alanine, aspartic acid, asparagine, glutamic acid, serine, homoserine, alpha-amino adipic acid, phenylalanine, tyrosine, tryptophan, histidine, pyridylalanine, thienylalanine, thiazolylalanine, furylalanine, naphthylalanine, the side chain being substituted or not with Alkoxy, hydroxyl, halide, aminoalkyl, amide, sulfonamide, aryl, alkyl, heteroaryl or amidine. In an embodiment, at least one or more (e.g., 2, 3 or 4) amino acid residue of the compound is in L configuration. In an embodiment, at least one or more (e.g., 2, 3 or 4) amino acid residue of the compound is in D configuration. Unless indicated otherwise, as used herein in the terms "CONH-amino acid residue(s)" and "CO-amino-acid residue(s)" are used interchangeably: the NH of "CONH" is that of the amino acid residue lined to the CO.

As used herein, "alkenyl" refers to straight, branched chain or cyclic hydrocarbyl groups having at least one carbon-carbon double bond, and having in the range of about 2 up to about 100 carbon atoms, for example from 2 to 12 carbon atoms, and "substituted alkenyl" refers to alkenyl groups further bearing one or more substituents as set forth above. As used herein, "lower alkenyl" refers to alkenyl moieties having from 2 to about 6 carbon atoms, for example from 1 to 3 carbon atoms.

As used herein, "alkynyl" refers to straight or branched chain hydrocarbyl groups having at least one carbon-carbon triple bond, and having in the range of about 2 up to about 100 carbon atoms, for example from 2 to 12 carbon atoms and "substituted alkynyl" refers to alkynyl groups further bearing one or more substituents as set forth above. As used herein, "lower alkynyl" refers to alkynyl moieties having from 2 to about 6 carbon atoms, for example 2, 3 or 4 carbons.

As used herein the term "aryl" refers to substituted or unsubstituted aryl (C$_5$ to C$_{14}$ (e.g., C$_5$-C$_6$)). "Substituted aryl" refers to aryl groups further bearing one or more substituents as set forth above in the definition of "substituted alkyl" above. In a more specific embodiment, the substituent is an alkyl, a heterocycle, an halide, SH, OH, OCH$_3$, NO$_2$, NH$_2$, CO$_2$H, CONH$_2$ or SO$_2$NH$_2$.

As used herein the term "amino acid residue" refers to any natural/standard and non-natural/non-standard amino acid residue in (L) or (D) configuration, and includes alpha or alpha-disubstituted amino acids. It refers to isoleucine, leucine, lysine, methionine, phenylalanine, threonine, tryptophan, valine, arginine, alanine, asparagine, aspartic acid, cysteine, glutamic acid, glutamine, glycine, histidine, proline, serine, tyrosine. It also includes beta-alanine, 3-aminopropionic acid, 2,3-diamino propionic acid, alpha-aminoisobutyric acid (Aib), 4-amino-butyric acid, N-methylglycine (sarcosine), hydroxyproline, omithine (e.g., L-omithine), citrulline, t-butylalanine, t-butylglycine, N-methylisoleucine, phenylglycine, cyclohexylalanine, cyclopentylalanine, cyclobutylalanine, cyclopropylalanine, cyclohexylglycine, cyclopentylglycine, cyclobutylglycine, cyclopropylglycine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (hArg), N-acetyl lysine, 2-amino butyric acid, 2-amino butyric acid, 2,4,-diaminobutyric acid (D- or L-), p-aminophenylalanine, N-methylvaline, selenocysteine, homocysteine, homoserine (HoSer), cysteic acid, epsilon-amino hexanoic acid, delta-amino valeric acid, or 2,3-diaminobutyric acid (D- or L-), etc. These amino acids are well known in the art of biochemistry/peptide chemistry. Similarly, the terms "side chain of amino acid" refer to the side chain of any natural/standard and non-natural/non standard amino acid residue in (L) or (D) configuration as described above.

Compounds of the present invention which include peptides may comprise replacement of at least one of the peptide bonds with an isosteric modification. Compounds of the present invention which include peptides may be peptidomimetics. A peptidomimetic is typically characterised by retaining the polarity, three dimensional size and functionality (bioactivity) of its peptide equivalent, but wherein one or more of the peptide bonds/linkages have been replaced, often by proteolytically more stable linkages. Generally, the bond which replaces the amide bond (amide bond surrogate) conserves many or all of the properties of the amide bond, e.g. conformation, steric bulk, electrostatic character, potential for hydrogen bonding, etc. Typical peptide bond replacements include esters, polyamines and derivatives thereof as well as substituted alkanes and alkenes, such as aminomethyl and ketomethylene. For example, the peptide may have one or more peptide linkages replaced by linkages such as —CH$_2$NH—, —CH$_2$S—, —CH$_2$—CH$_2$—, —CH═CH— (cis or trans), —CH$_2$SO—, —CH(OH)CH$_2$—, or —COCH$_2$—, —N—NH—, —CH$_2$NHNH—, or peptoid linkages in which the side chain is connected to the nitrogen atom instead of the carbon atom. Such peptidomimetics may have greater chemical stability, enhanced biological/pharmacological properties (e.g., half-life, absorption, potency, efficiency, etc.) and/or reduced antigenicity relative its peptide equivalent.

Salts, Esters, Hydrates and Solvates

The compounds of the present invention include pharmacologically acceptable salts and ester derivatives thereof as well as hydrates or solvates thereof and all stereoisomeric forms of the referenced compounds. The compounds and pharmacologically acceptable esters thereof of the present invention can form pharmacologically acceptable salts if necessary.

Salts

The terms "pharmacologically acceptable salt thereof" refer to a salt to which the compounds of the present invention can be converted. Preferred examples of such a salt include alkali metal salts such as a sodium salt, a potassium salt, a lithium salt, magnesium or calcium salts; alkaline earth metal salts such as a calcium salt and a magnesium salt; metal salts such as an aluminum salt, an iron salt, a zinc salt, a copper salt, a nickel salt and a cobalt salt; amine salts such as inorganic salts including an ammonium salt; organic salts or ammonium salts such as a t-octylamine salt, a dibenzylamine salt, a morpholine salt, a glucosamine salt, a phenylglycine alkyl ester salt, an ethylenediamine salt, an N-methylglucamine salt, a guanidine salt, a diethylamine salt, a triethylamine salt, a dicyclohexylamine salt, an N,N'-dibenzylethylenediamine salt, a chloroprocaine salt, a procaine salt, a diethanolamine salt, an N-benzyl-phenethylamine salt, a piperazine salt, a tetramethylammonium salt and a tris(hydroxymethyl)aminomethane salt; inorganic acid salts such as hydrohalic acid salts such as a hydrofluoride, a hydrochloride, a hydrobromide or a hydroiodide, a nitrate, a perchlorate, a sulfate or a phosphate; lower alkanesulfonates such as a methanesulfonate, trifluoromethanesulfonate or an ethanesulfonate; arylsulfonates such as a benzenesulfonate or a p-toluenesulfonate and the like, which are non-toxic to living organisms; organic acid salts such as an acetate, a malate, adipate, a fumarate, a succinate, a citrate, alginate, ascorbate, benzoate, benzenesulfonate, bisulfate, butyrate, camphorate, camphorsulfonate, cinnamate, cyclopentanepropionate, digluconate, dodecylsulfate, ethanesulfonate, glucoheptanoate, glycerophosphate, hemisulfate, heptanoate, hexanoate, hydrochloride, hydrobromide, hydroiodide, 2-hydroxyethanesulfonate, itaconate, lactate, maleate, mandelate, sulfonate, methanesulfonate, trifluoromethanesulfonates, ethanesulfonates 2-naphthalenesulfonate, nicotinate, nitrate, oxalate, pamoate, pectinate, persulfate, 3-phenylpropionate, picrate, pivalate, propionate, tartrate, thiocyanate, tosylate, trifluoroacetic acid, undecanoate, a tartrate, an oxalate or a maleate; and amino acid salts such as a glycine salt, a lysine salt, an arginine salt, an ornithine salt, histidine, a glutamate or an aspartate salt. Additionally, basic nitrogen containing groups may be quaternized with such agents as lower alkyl halides such as methyl, ethyl, propyl, and butyl chlorides, bromides and iodides; dialkyl sulfates including dimethyl, diethyl, and dibutyl sulfate; and diamyl sulfates, long chain halides such as decyl, lauryl, myristyl and strearyl chlorides, bromides and iodides, aralkyl halides including benzyl and phenethyl bromides, and others. For further example, see S. M. Berge, et al. "Pharmaceutical Salts," J. Pharm. Sci. 1977, 66, 1-19. Such salts can be formed quite readily by those skilled in the art using standard techniques.

Preferred examples of the salts formed with an acidic group present in the compounds of the present invention include metal salts such as alkali metal salts (e.g., sodium salts, potassium salts and lithium salts), alkali earth metal salts (e.g., calcium salts and magnesium salts), aluminum salts and iron salts; amine salts such as inorganic amine salts (e.g., ammonium salts) and organic amine salts (e.g., t-octylamine salts, dibenzylamine salts, morpholine salts, glucosamine salts, phenylglycinealkyl ester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts. N-benzylphenethylamine salts, piperazine salts, tetramethylammonium salts and tris(hydroxymethyl)aminomethane salts; and amino acid salts such as glycine salts, lysine salts, arginine salts, ornithine salts, glutamates and aspartates.

All salts are intended to be pharmaceutically acceptable salts within the scope of the invention and all salts are considered equivalent to the free forms of the corresponding compounds for purposes of the invention.

Esters

Physiologically/pharmaceutically acceptable esters are also useful as active medicaments. The term "pharmaceutically acceptable esters" embraces esters of the compounds of the present invention, in which hydroxy groups (e.g., in carboxylic acid) have been converted to the corresponding esters and may act as a prodrug which, when absorbed into the bloodstream of a warm-blooded animal, may cleave in such a manner as to release the drug form and permit the drug to afford improved therapeutic efficacy. Such esters can be formed with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non-toxic to living organisms. Further examples are the esters with aliphatic or aromatic acids such as acetic acid or with aliphatic alcohol (e.g., alkyl esters, including methyl, ethyl, propyl, isopropyl, butyl, isobutyl or pentyl esters, and the like) or aromatic alcohols (e.g., benzyl ester).

Esters can be prepared from their corresponding acids or salts by a variety of methods known to those skilled in the art, such as, for example, by first transforming the acid to the acid chloride and then reacting the acid chloride with a suitable alcohol. Other suitable methods for making esters are described in Kemp and Vellaccio, 1980.

Where esters of the invention have a basic group, such as an amino group, the compound can be converted to a salt by reacting it with an acid, and in the case where the esters have an acidic group, such as a sulfonamide group, the compound can be converted to a salt by reacting it with a base. The compounds of the present invention encompass such salts.

Salts and esters of the compounds of the present invention may be prepared by known method by employing appropriate starting materials or intermediate compounds that are readily available and/or are described herein.

Generally, a desired salt of a compound of this invention can be prepared in situ during the final isolation and purification of a compound by means well known in the art. For example, a desired salt can be prepared by separately reacting the purified compound in its free base or free acid form with a suitable organic or inorganic acid, or suitable organic or inorganic base, respectively, and isolating the salt thus formed. In the case of basic compounds, for example, the free base is treated with anhydrous HCl in a suitable solvent such as THF, and the salt isolated as a hydrochloride salt. In the case of acidic compounds, the salts may be obtained, for example, by treatment of the free acid with anhydrous ammonia in a suitable solvent such as ether and subsequent isolation of the ammonium salt. These methods are conventional and would be readily apparent to one skilled in the art.

The compounds of this invention may be esterified by a variety of conventional procedures including reacting the appropriate anhydride, carboxylic acid or acid chloride with the alcohol group of a compound of this invention. The appropriate anhydride is reacted with the alcohol in the presence of a base to facilitate acylation such as 1,8-bis [dimethylamino]naphthalene or N,N-dimethylaminopyridine. Or, an appropriate carboxylic acid can be reacted with the alcohol in the presence of a dehydrating agent such as dicyclohexylcarbodiimide, 1-[3-dimethylaminopropyl]-3-ethylcarbodiimide or other water soluble dehydrating agents which are used to drive the reaction by the removal of water, and, optionally, an acylation catalyst. Esterification can also be effected using the appropriate carboxylic acid in the presence of trifluoroacetic anhydride and, optionally, pyridine, or in the presence of N,N-carbonyldiimidazole with pyridine. Reaction of an acid chloride with the alcohol can be carried out with an acylation catalyst such as 4-DMAP or pyridine.

One skilled in the art would readily know how to successfully carry out these as well as other known methods of etherification of alcohols.

Prodrugs and Solvates

Prodrugs and solvates of the compounds of the invention are also contemplated herein. A discussion of prodrugs is provided in T. Higuchi and V. Stella, Pro-drugs as Novel Delivery Systems (1987) 14 of the A.C.S. Symposium Series, and in Bioreversible Carriers in Drug Design, (1987) Edward B. Roche, ed., American Pharmaceutical Association and Pergamon Press. The term "prodrug" means a compound (e.g., a drug precursor) that is transformed in vivo to yield a compound of the present invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention or a pharmaceutically acceptable salt, hydrate or solvate of the compound contains a carboxylic acid functional group, a prodrug can comprise an ester formed by the replacement of the hydrogen atom of the acid group with a group such as, for example, (C1-C8)alkyl, (C2-C12)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—(C1-C2)alkylamino(C2-C3)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl, and the like.

Similarly, if a compound of the present invention contains an alcohol functional group, a prodrug can be formed by the replacement of the hydrogen atom of the alcohol group with a group such as, for example, (C1-C6)alkanoyloxymethyl, 1-(($C_1$-$C_6$)alkanoyloxy)ethyl, 1-methyl-1-(($C_1$-$C_6$)alkanoyloxy)ethyl, ($C_1$-$C_6$)alkoxycarbonyloxymethyl, N—($C_1$-$C_6$)alkoxycarbonylaminomethyl, succinoyl, ($C_1$-$C_6$)alkanoyl, α-amino($C_1$-$C_4$)alkanyl, arylacyl and α-aminoacyl, or α-aminoacyl-α-aminoacyl, where each α-aminoacyl group is independently selected from the naturally occurring L-amino acids, $P(O)(OH)_2$, $—P(O)(O(C_1-C_6)alkyl)_2$ or glycosyl (the radical resulting from the removal of a hydroxyl group of the hemiacetal form of a carbohydrate), and the like.

If a compound of the present invention incorporates an amine functional group, a prodrug can be formed by the replacement of a hydrogen atom in the amine group with a group such as, for example, R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl, —C(OH)C(O)OY1 wherein Y1 is H, ($C_1$-$C_6$)alkyl or benzyl, —C($OY_2$)$Y_3$ wherein $Y_2$ is ($C_1$-$C_4$) alkyl and $Y_3$ is ($C_1$-$C_6$)alkyl, carboxy ($C_1$-$C_6$)alkyl, amino($C_1$-$C_4$)alkyl or mono-N— or di-N,N— ($C_1$-$C_6$)alkylaminoalkyl, —C($Y4$)$Y5$ wherein $Y_4$ is H or methyl and $Y_5$ is mono-N— or di-N,N—($C_1$-$C_6$)alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. A "Hydrate" is a solvate wherein the solvent molecule is $H_2O$.

Preparation of solvates is generally known. Thus, for example, M. Caira et al, J. Pharmaceutical Sci., 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, AAPS Pharm Sci Tech., 5(1), article 12 (2004); and A. L. Bingham et al, Chem. Commun., 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

Hydrates

As used herein the terms, "pharmaceutically acceptable hydrate" refer to the compounds of the instant invention crystallized with one or more molecules of water to form a hydrated form.

Stereoisomers, Diastereomers, Enantiomers, Racemates, Tautomers

The compounds of the present invention have asymmetric carbon atoms and can exist in the form of diastereomers, optically pure enantiomers or as racemates. The term "compound" as used herein embraces all of these forms.

Diastereomers (sometimes called diastereoisomers) are stereoisomers that are not enantiomers. Diastereomerism occurs when two or more stereoisomers of a compound have different configurations at one or more (but not all) of the equivalent (related) stereocenters and are not mirror images of each other. When two diastereoisomers differ from each other at only one stereocenter they are epimers. Each stereocenter gives rise to two different configurations and thus to two different stereoisomers.

Diastereomers differ from enantiomers in that the latter are pairs of stereoisomers which differ in all stereocenters and are therefore mirror images of one another. Enantiomers of a compound with more than one stereocenter are also diastereomers of the other stereoisomers of that compound that are not their mirror image. Diastereomers have different physical properties and different reactivity, unlike enantiomers. Diastereomers of the present invention include tomatidine and 3 alpha-hydroxy-tomatidine for exemple.

For purposes of this Specification, "pharmaceutically acceptable tautomer" means any tautomeric form of any compound of the present invention.

The purification of enantiomers and the separation of isomeric mixtures of a compound of the present invention may be accomplished by standard techniques known in the art.

Inhibitors of Matriptase for Treatment of Orthomyxoviridae Infections

The present invention further concerns the use of any inhibitor of matriptase, i.e. any agent that decreases matriptase expression and/or activity, in target cells. Such inhibitors may be useful for the treatment of orthomyxoviridae infections, such as influenza infections. In an embodiment, the inhibitor is a compound defined above. In other embodiments, the inhibitor is an agent for RNA interference, an antibody or a small molecule inhibitor.
Agents for RNA Interference (siRNAs, shRNA, miRNA)

The present invention further concerns the use of RNA interference (RNAi) to decrease matriptase expression/activity in target cells (e.g., respiratory epithelial cells). "RNA interference" refers to the process of sequence specific suppression of gene expression mediated by RNA molecules such as small interfering RNA (siRNA), microRNA (miRNA) or small/short hairpin RNA (shRNA) without generalized suppression of protein synthesis. While the invention is not limited to a particular mode of action, RNAi may involve degradation of messenger RNA (e.g., matriptase mRNA, such as an mRNA comprising a sequence corresponding to the sequence of SEQ ID NO:1) by an RNA induced silencing complex (RISC), preventing translation of the transcribed targeted mRNA. Alternatively, it may involve methylation of genomic DNA, which shuts down transcription of a targeted gene. The suppression of gene expression caused by RNAi may be transient or it may be more stable, even permanent.

RNA interference is triggered by the presence of short interfering RNAs of about 20-25 nucleotides in length which comprise about 19 base pair duplexes. These siRNAs can be of synthetic origin or they can be derived from a ribonuclease III activity (e.g., dicer ribonuclease) found in cells. The RNAi response also features an endonuclease complex containing siRNA, commonly referred to as an RNA-induced silencing complex (RISC), which mediates the cleavage of single stranded RNA having a sequence complementary to the antisense region of the siRNA duplex. Cleavage of the target RNA (e.g., matriptase mRNA) takes place in the middle of the region complementary to the antisense strand of the siRNA duplex (Elbashir et al., 2001, Genes Dev., 15:188).

"Small interfering RNA" of the present invention refers to any nucleic acid molecule capable of mediating RNA interference "RNAi" or gene silencing (see for example, Bass, 2001, Nature, 411:428-429; Elbashir et al., 2001, Nature, 411:494-498; Kreutzer et al., International PCT publication No. WO 00/44895; Zernicka-Goetz et al., International PCT publication No. WO 01/36646; Fire, International PCT publication No. WO99/32619; Mello and Fire, International PCT publication No. WO01/29058; Deschamps-Depaillette, International PCT publication No. WO99/07409; Han et al., International PCT publication No. WO 2004/011647; Tuschl et al., International PCT publication No. WO 02/44321; and Li et al., International PCT publication No. WO 00/44914). Specific embodiments of siRNA of the present invention are double stranded RNA molecules from about ten to about 30 nucleotides long that are named for their ability to specifically interfere with protein expression. In one embodiment, siRNA of the present invention are 12-28 nucleotides long, more preferably 15-25 nucleotides long, even more preferably 19-23 nucleotides long and most preferably 21-23 nucleotides long. Therefore preferred siRNA of the present invention are about 12, 13, 14, 15, 16, 17, 18, 19, 20, 21, 22, 23, 24, 25, 26, 27 or 28 nucleotides in length. As used herein, siRNA molecules need not to be limited to those molecules containing only RNA, but further encompass chemically modified nucleotides and non-nucleotides. siRNA used in examples herein include s13520 (Ambion) Silencer® Select siRNAs gene symbol ST14, and S2: EHU012511 (Sigma-Aldrich) MISSION® esiRNA targeting human ST14 (esiRNA1).

The length of one strand designates the length of an siRNA molecule. For example, a siRNA that is described as a 23 ribonucleotides long (a 23 mer) could comprise two opposite strands of RNA that anneal together for 21 contiguous base pairing. The two remaining ribonucleotides on each strand would form what is called an "overhang". In a particular embodiment, the siRNA of the present invention contains two strands of different lengths. In this case, the longer strand designates the length of the siRNA. For example, a dsRNA containing one strand that is 20 nucleotides long and a second strand that is 19 nucleotides long is considered a 20 mer.

siRNAs that comprise an overhang are desirable. The overhang may be at the 3' or 5' end. Preferably, the overhangs are at the 3' end of an RNA strand. The length of an overhang may vary but preferably is about 1 to 5 nucleotides long. Generally, 21 nucleotides siRNA with two nucleotides 3'-overhang are the most active siRNAs.

siRNA of the present invention are designed to decrease matriptase expression in a target cell by RNA interference. siRNA of the present invention comprise a sense region and an antisense region wherein the antisense region comprises a sequence complementary to a matriptase mRNA sequence and the sense region comprises a sequence complementary to the antisense sequence of matriptase mRNA. A siRNA molecule can be assembled from two nucleic acid fragments wherein one fragment comprises the sense region and the second fragment comprises the antisense region of siRNA molecule. The sense region and antisense region can also be covalently connected via a linker molecule. The linker molecule can be a polynucleotide linker or a non polynucleotide linker.

Antibodies

The present invention further concerns the use of antibodies that inhibit matriptase activity in target cells (e.g., respiratory epithelial cells), e.g., that inhibit the cleavage of Influenza HA by matriptase. In an embodiment, the antibodies specifically recognize/bind to a matriptase polypeptide (e.g., the matriptase polypeptide of SEQ ID NO:2). In an embodiment, the antibodies specifically recognize/bind to an epitope located in a region of matriptase that is involved in the cleavage of Influenza HA (the catalytic domain), for example an epitope located in the region spanning about residues 615 to 855, for example about residues 700 to 840 of matriptase. In an embodiment, the antibodies specifically recognizes/binds to an epitope located in a region spanning about residues 708 to 829 of matriptase. In embodiments, the antibodies specifically recognizes/binds to an epitope comprising one or more (e.g., 1, 2, 3, 4, 5, 6, 7, 8, 9, or all) of the following residues of matriptase: $Phe^{708}$, $Gln^{783}$, $Asp^{799}$, $Ser^{800}$, $Gln^{802}$, $Gly^{803}$, $Ser^{805}$, $Gly^{827}$, $Asp^{828}$ and/or $Gly^{829}$.

The term "antibody" is used in the broadest sense, and covers monoclonal antibodies (including full-length monoclonal antibodies), polyclonal antibodies, multispecific antibodies, chimeric antibodies and humanized antibodies, so long as they exhibit the desired biological activity (e.g., inhibiting the binding of matriptase to influenza HA, and/or the matriptase-mediated cleavage of influenza HA). Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories).

Polyclonal antibodies are preferably raised in animals by multiple subcutaneous (s.c.), intravenous (i.v.) or intraperitoneal (i.p.) injections of the relevant antigen (e.g., a peptide or polypeptide comprising a sequence of matriptase) with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R_1N$=C=NR, where R and $R_1$ are different alkyl groups.

Animals may be immunized against the antigen, immunogenic conjugates, or derivatives by combining the antigen or conjugate (e.g., 100 µg for rabbits or 5 µg for mice) with 3 volumes of Freund's complete adjuvant and injecting the solution intradermally at multiple sites. One month later the animals are boosted with the antigen or conjugate (e.g., with ⅕ to ⅒ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Antibodies specific for the catalytic domain (residues 615 to 855) of human matriptase and exhibiting inhibitory activity against matriptase are described in U.S. Pat. No. 7,572, 444. Examples of such antibodies include those having the sequences depicted in Table 1 below.

TABLE 1

Sequences of representative anti-matriptase antibodies disclosed in U.S. Pat. No. 7,572,444

| Heavy chain | | |
|---|---|---|
| FR1 | CDR1 | FR2 |
| EVQLLESGGGLVQPGGSLRLSCAAS | GFTFSSYAMS | WVRQAPGKGLEWVS |
| EVQLLESGGGLVQPGGSLRLSCAAS | GFTFSSYAMS | WVRQAPGKGLEWVS |
| EVQLLESGGGLVQPGGSLRLSCAAS | GVTFSSYAMS | WVRQAPGKGLEWVS |
| CDR2 | FR3 | CDR3 | FR4 |
| AISGSGGSTYYADSVKG | RFTISRDNSKNTLYLQ MNSLRAEDTAVYYCAK | | WGQGTLVTVSS |
| AISSSGVNTHYADSVKG | RFTISRDNSKNTLYLQ MNSLRAEDTAVYYCAT | IASIALRGYYFDY | WGQGTLVTVSS |
| AISSSGGNTHYADSVKG | RFTISRDNSKNTLYLQ MNSLRAEDTAVYYCAT | IASIATRGYFFNY | WGQGTLVTVSS |

TABLE 1-continued

Sequences of representative anti-matriptase antibodies disclosed in U.S. Pat. No. 7,572,444

Light chain

| FR1 | CDR1 | FR2 |
|---|---|---|
| EIVLTQSPGTLSLSPGERATLSC | RASQSVSSSYLA | WYQQKPGQAPRLLIY |
| EIVLTQSPGTLSLSPGERATLSC | RASQTFGSSYLA | WYQQKPGQAPRLLIY |
| DIVLTQSPGTLSLSPGERATLSC | RASQTFSSNSLA | WYQQKPGQAPSLLIY |

| CDR2 | FR3 | CDR3 | FR4 |
|---|---|---|---|
| GASSRAT | GIPDRFSGSGSGTDFT LTISRLEPEDFAVYYC | | FGQGTKVEIK |
| GASSRAT | VIPDRFSGSGSGTDFT LTISRLEPEDFAVYYC | QQYGSSPWT | FGQGTKVEIK |
| GASSRAT | GIPDRFSGSGSGTDFT LTISRLEPEDFAVYYC | QQYGSSPWT | FGQGTKVEIK |

Other matriptase antibodies are disclosed in Sun et al., 2003, *Biochemistry* 42: 892-900 and Lin et al., 1997, *Journal of Biological Chemistry*, 272: 9147-9152.

Small Molecules and Other Matriptase Inhibitors

Inhibitors of matriptase activity that may be used in the methods of the present invention include those described in U.S. Pat. Nos. 6,677,377 and 7,019,019. The structures of representative examples of such inhibitors are presented in Tables 2 and 3 below:

TABLE 2

Structures of representative matriptase inhibitors disclosed in U.S. Pat. No. 6,677,377

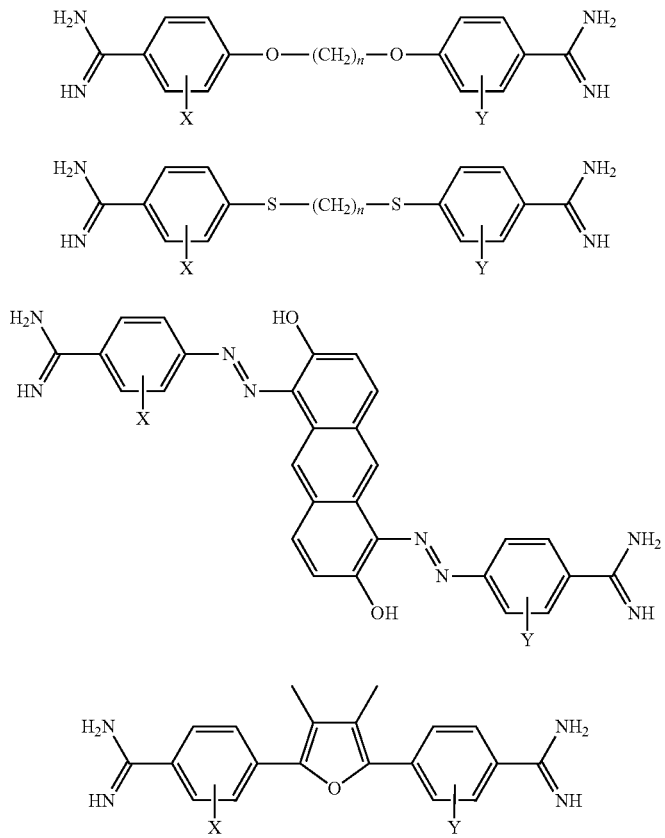

TABLE 2-continued
Structures of representative matriptase inhibitors disclosed in U.S. Pat. No. 6,677,377
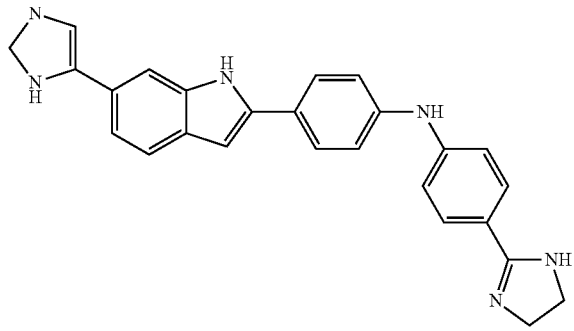 [SMILES: C1=C(c2ccc3cc(-c4ccc(Nc5ccc(C6=NCCN6)cc5)cc4)[nH]c3c2)NCN1]
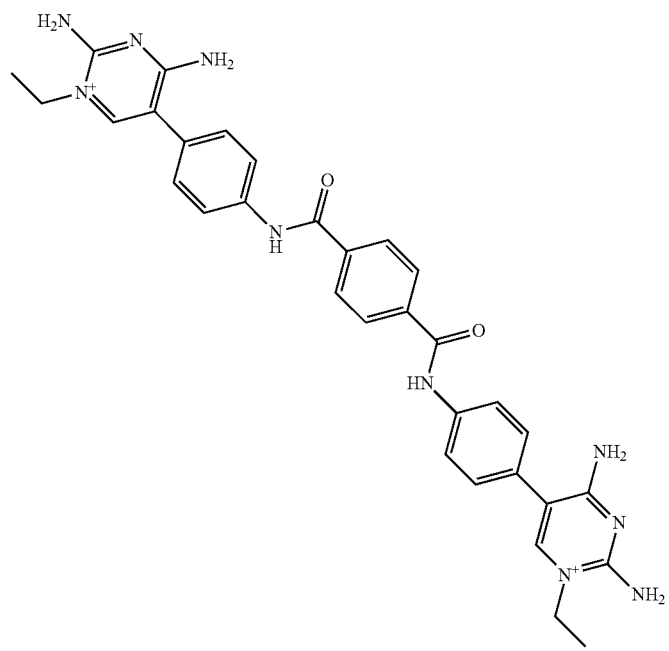 [SMILES: CC[n+]1cc(-c2ccc(NC(=O)c3ccc(C(=O)Nc4ccc(-c5c[n+](CC)c(N)nc5N)cc4)cc3)cc2)c(N)nc1N]
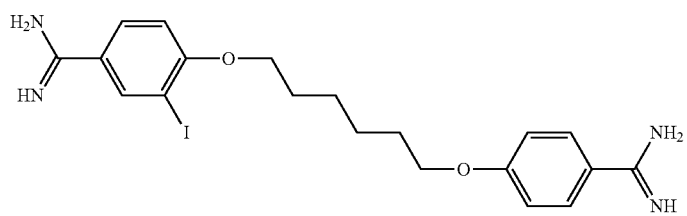
3-iodo-4,4'-hexanediyldioxy-bis-benzamidine
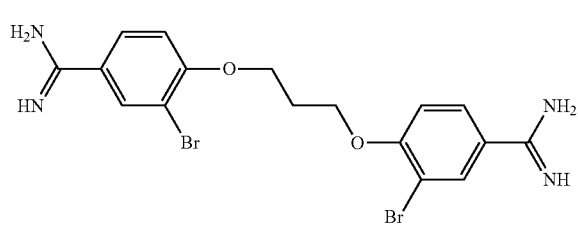 [SMILES: N=C(N)c1ccc(OCCCOc2ccc(C(=N)N)cc2Br)c(Br)c1]
3,3'-dibromo-4,4'-propanediyldioxy-bis-benzamidine TABLE 2-continued
Structures of representative matriptase inhibitors disclosed in U.S. Pat. No. 6,677,377
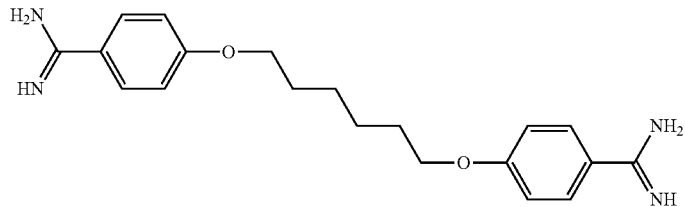
4,4'-hexanediyldioxy-bis-benzamidine
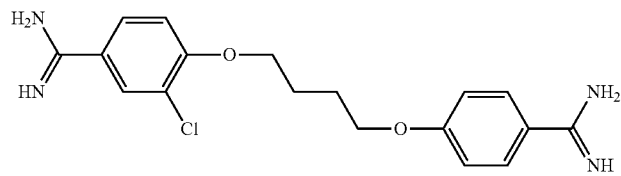 [SMILES: N=C(N)c1ccc(OCCCCOc2ccc(C(=N)N)cc2Cl)cc1]
3-chloro-4,4'-butanediyldioxy-bis-benzamidine
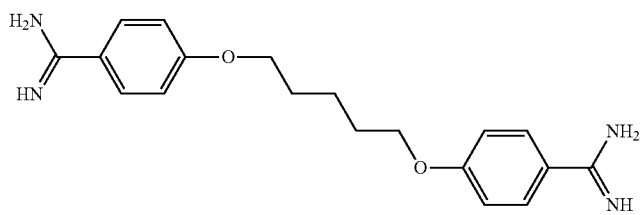
4,4'-pentanediyldioxy-bis-benzamidine
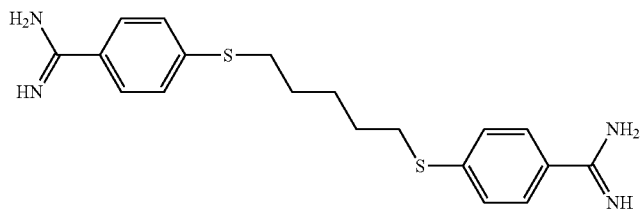 [SMILES: N=C(N)c1ccc(OCCCCCOc2ccc(C(=N)N)cc2)cc1]
1,5-Bis-(4-amidion-phenylmercapto)-pentane
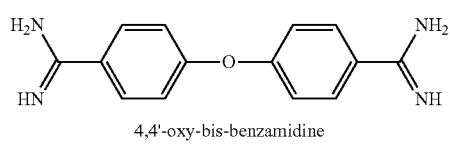
4,4'-oxy-bis-benzamidine
X and Y can be any substituent TABLE 3
Structures of representative matriptase inhibitors disclosed in U.S. Pat. No. 7,019,019
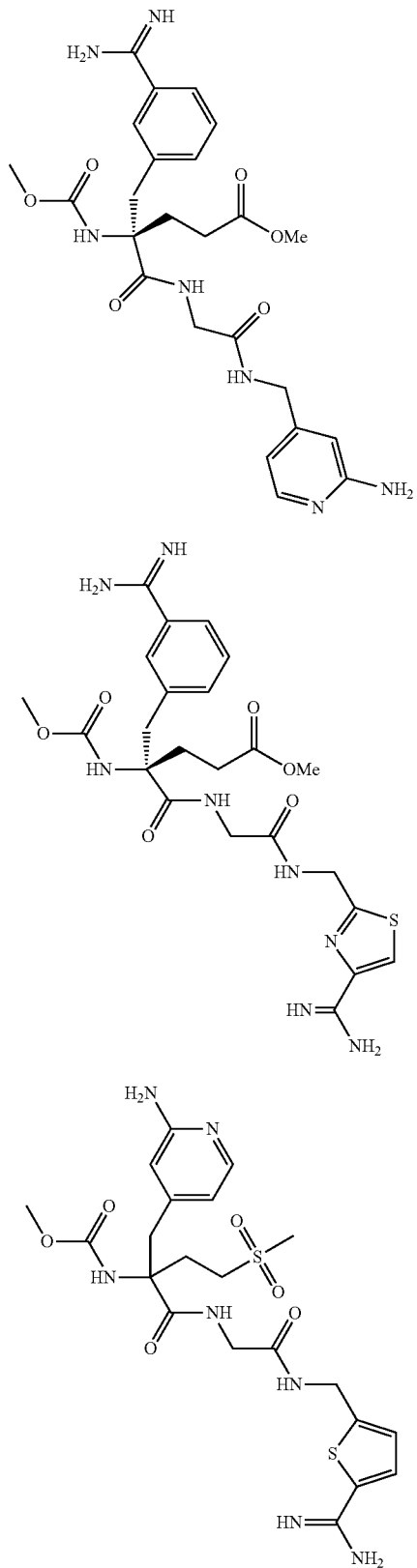
TABLE 3-continued
Structures of representative matriptase inhibitors disclosed in U.S. Pat. No. 7,019,019

41
TABLE 3-continued
Structures of representative matriptase inhibitors
disclosed in U.S. Pat. No. 7,019,019
42
TABLE 3-continued
Structures of representative matriptase inhibitors
disclosed in U.S. Pat. No. 7,019,019
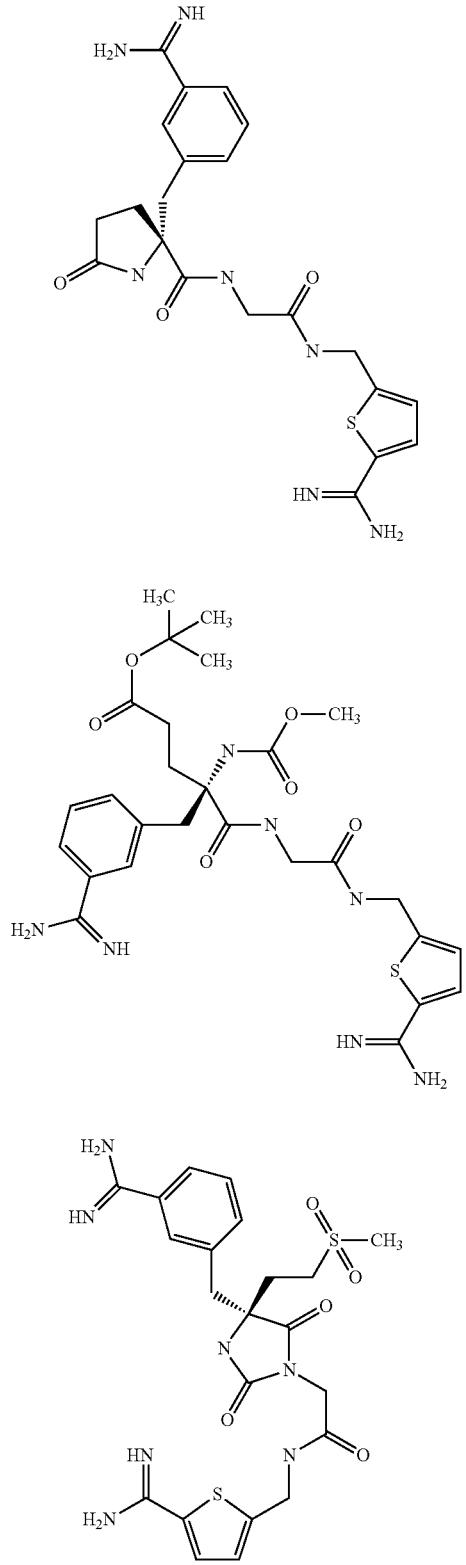
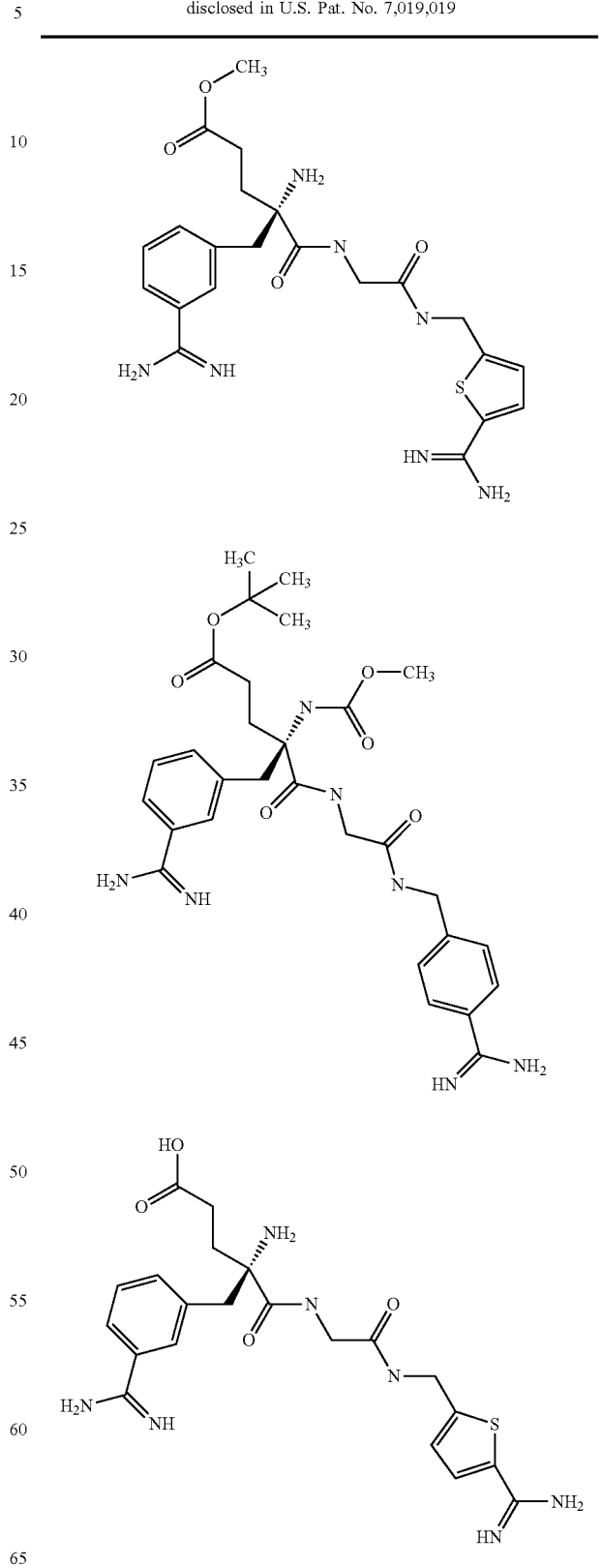

TABLE 3-continued
Structures of representative matriptase inhibitors disclosed in U.S. Pat. No. 7,019,019
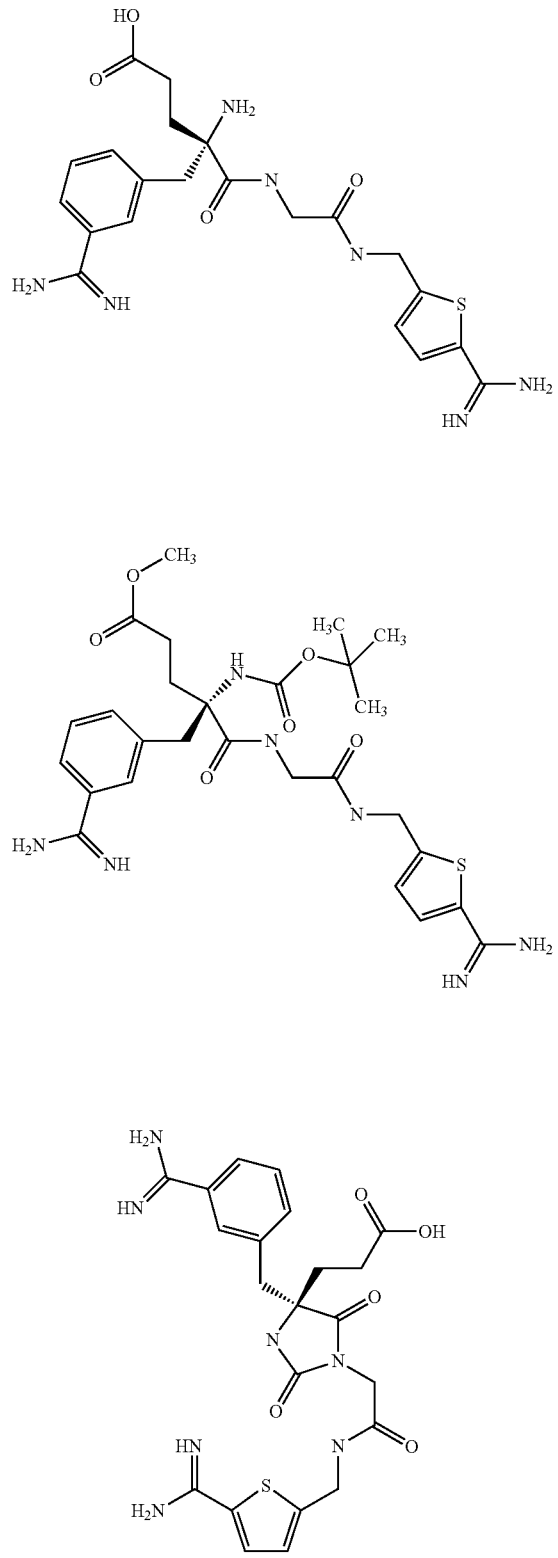
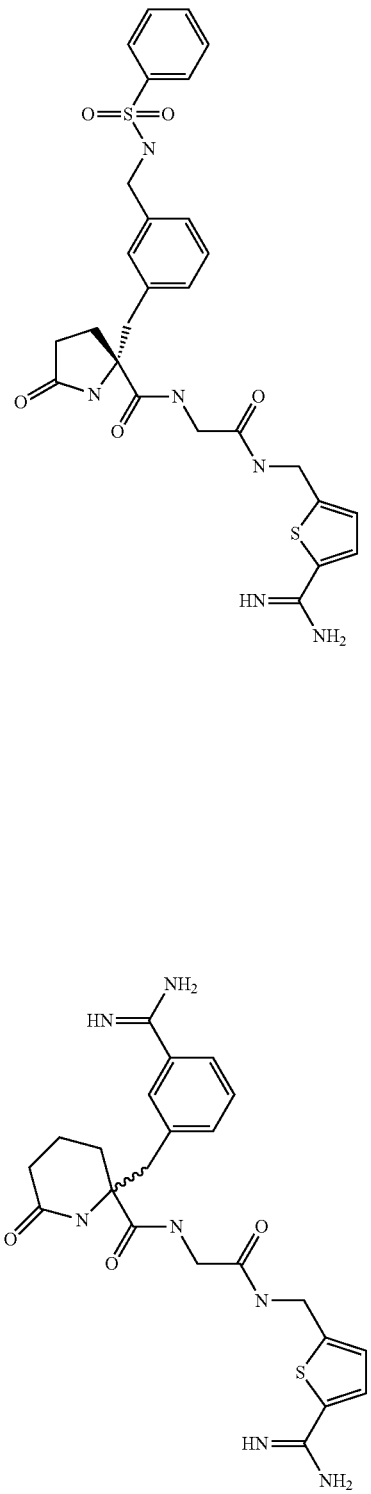

TABLE 3-continued
Structures of representative matriptase inhibitors disclosed in U.S. Pat. No. 7,019,019
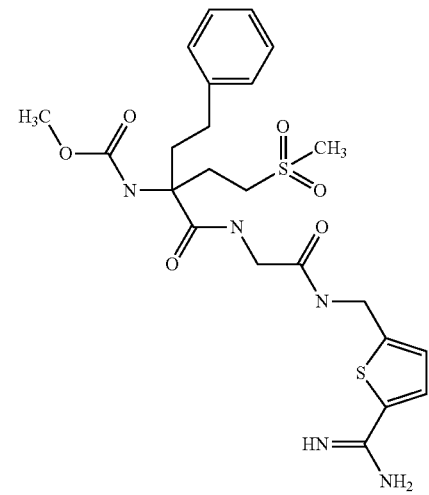 [SMILES: COC(=O)NC(CCc1ccccc1)(CCS(C)(=O)=O)C(=O)NCC(=O)NCc1ccc(C(=N)N)s1]
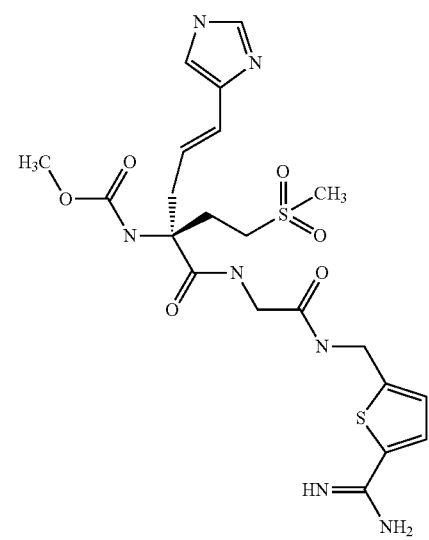 [SMILES: COC(=O)N[C@@](C/C=C/c1c[nH]cn1)(CCS(C)(=O)=O)C(=O)NCC(=O)NCc1ccc(C(=N)N)s1]
TABLE 3-continued
Structures of representative matriptase inhibitors disclosed in U.S. Pat. No. 7,019,019
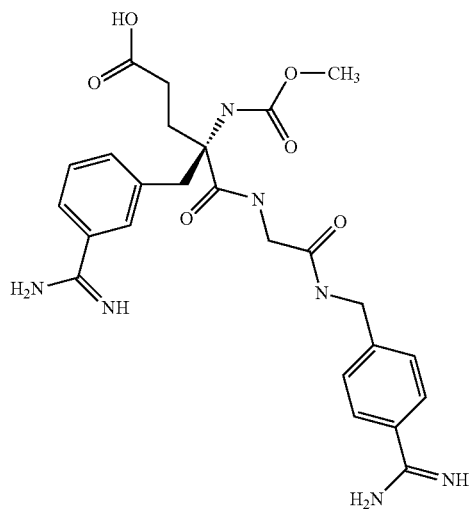
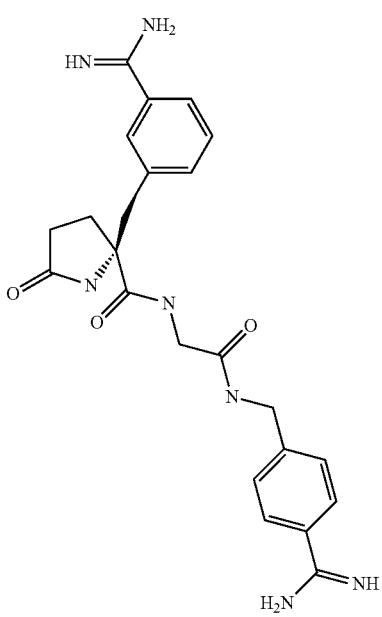 [SMILES: N=C(N)c1ccc(CNC(=O)CNC(=O)[C@@]2(Cc3cccc(C(=N)N)c3)CCC(=O)N2)cc1]

TABLE 3-continued
Structures of representative matriptase inhibitors disclosed in U.S. Pat. No. 7,019,019
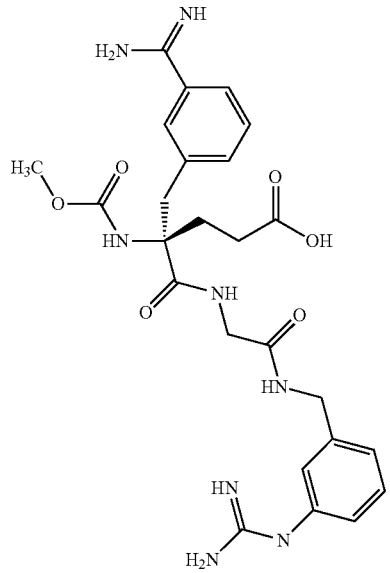 [SMILES: COC(=O)N[C@](CCC(=O)O)(Cc1cccc(C(=N)N)c1)C(=O)NCC(=O)NCc1cccc(NC(=N)N)c1]
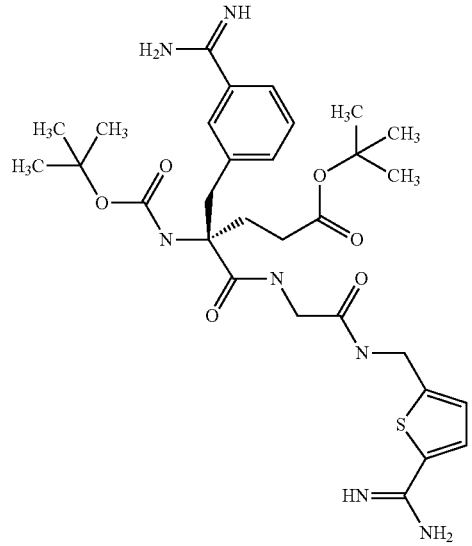
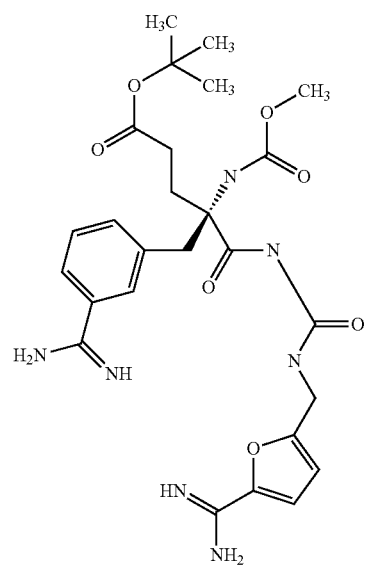
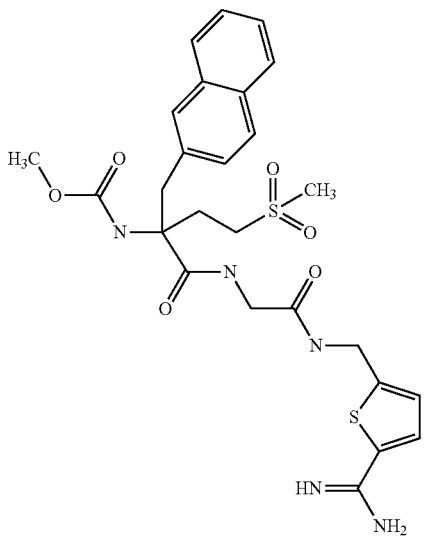 [SMILES: COC(=O)NC(CCS(C)(=O)=O)(Cc1ccc2ccccc2c1)C(=O)NCC(=O)NCc1ccc(C(=N)N)s1]

TABLE 3-continued
Structures of representative matriptase inhibitors disclosed in U.S. Pat. No. 7,019,019
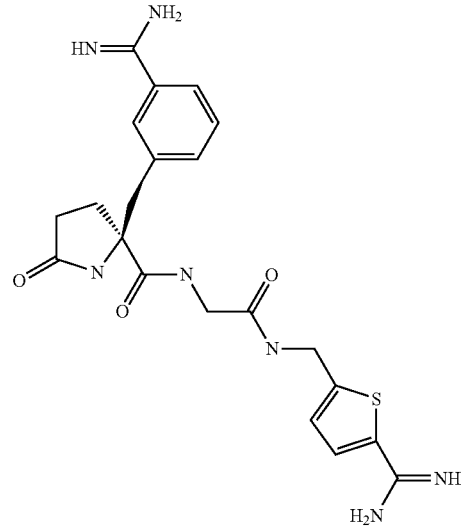 [SMILES: N=C(N)c1cccc(C[C@]2(C(=O)NCC(=O)NCc3ccc(C(=N)N)s3)CCC(=O)N2)c1]
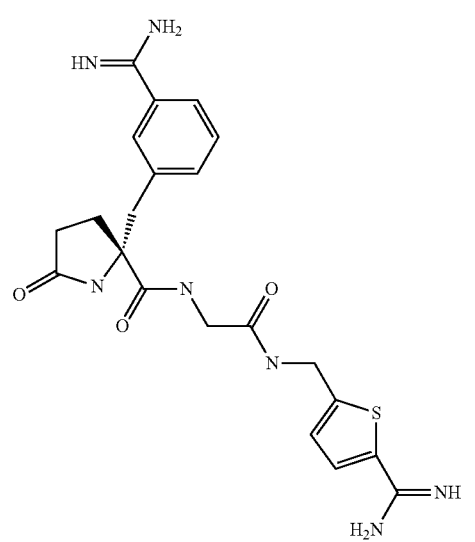 [SMILES: N=C(N)c1cccc(C[C@@]2(C(=O)NCC(=O)NCc3ccc(C(=N)N)s3)CCC(=O)N2)c1]
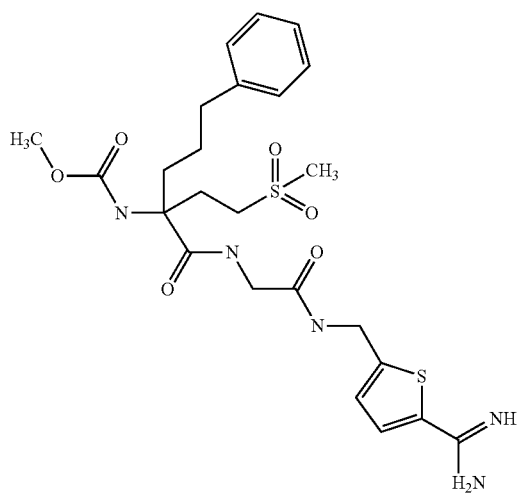 [SMILES: COC(=O)NC(CCCc1ccccc1)(CCS(C)(=O)=O)C(=O)NCC(=O)NCc1ccc(C(=N)N)s1]
TABLE 3-continued
Structures of representative matriptase inhibitors disclosed in U.S. Pat. No. 7,019,019
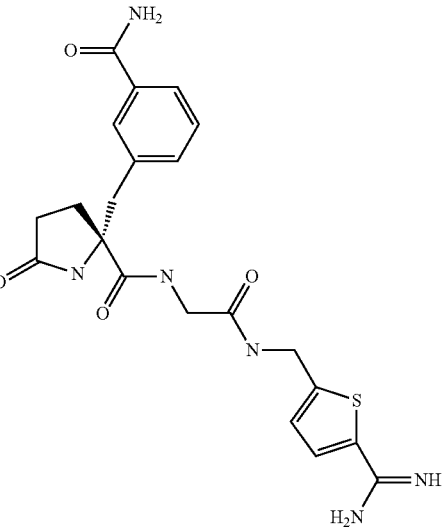
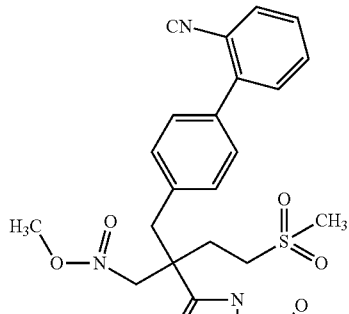
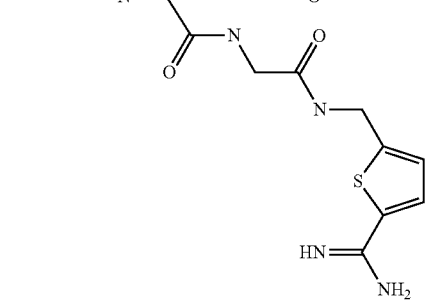

TABLE 3-continued
Structures of representative matriptase inhibitors disclosed in U.S. Pat. No. 7,019,019
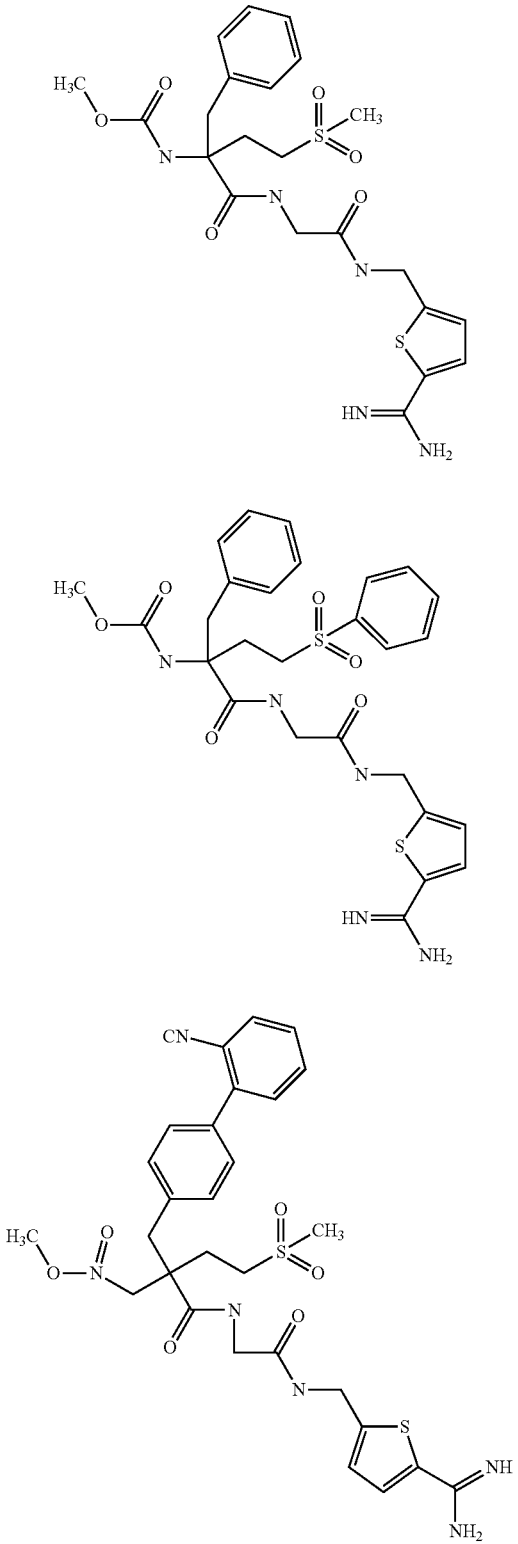
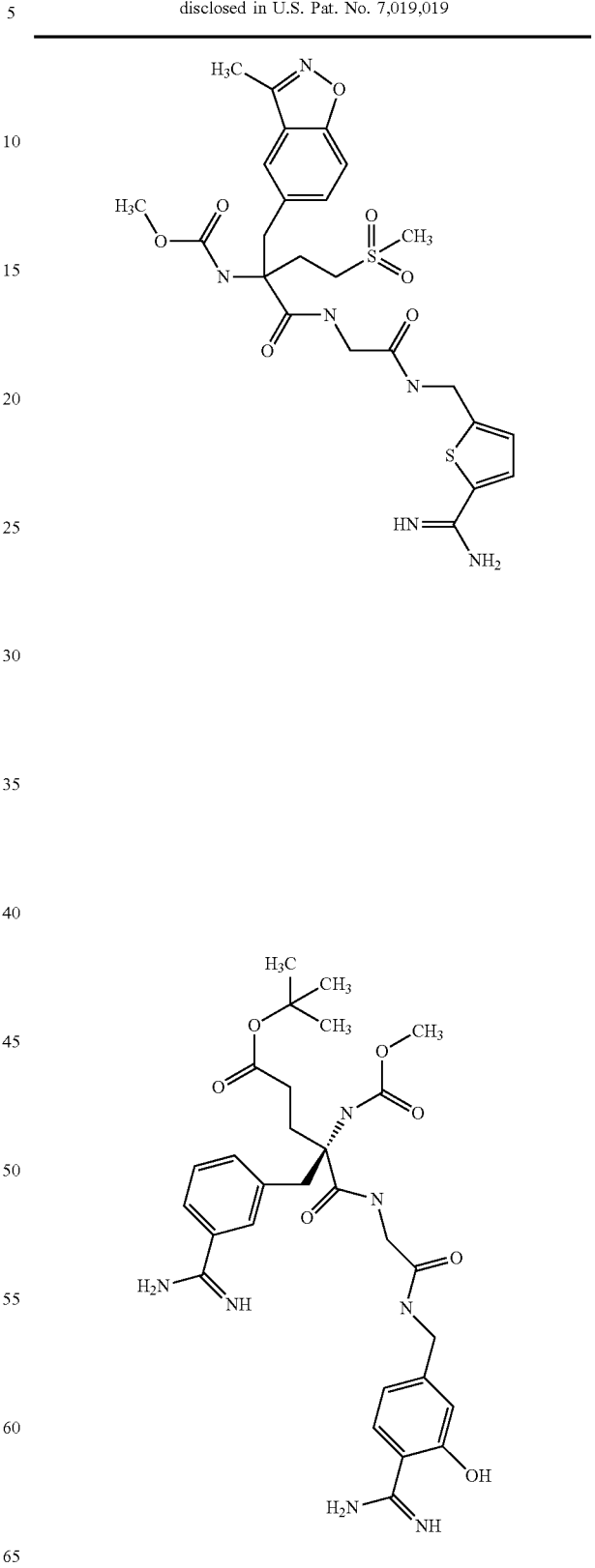

TABLE 3-continued
Structures of representative matriptase inhibitors
disclosed in U.S. Pat. No. 7,019,019
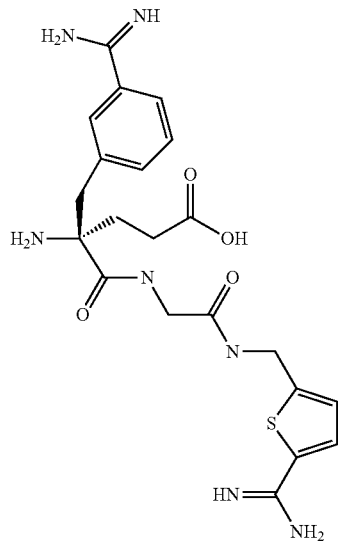 [SMILES: N=C(N)c1cccc(C[C@@](N)(CCC(=O)O)C(=O)NCC(=O)NCc2ccc(C(=N)N)s2)c1]
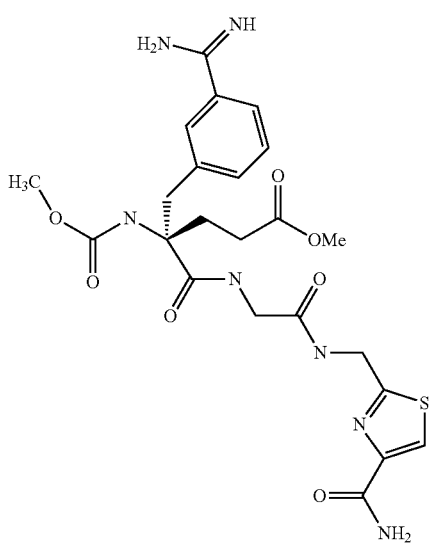 [SMILES: COC(=O)CC[C@](Cc1cccc(C(=N)N)c1)(NC(=O)OC)C(=O)NCC(=O)NCc1nc(C(N)=O)cs1]
TABLE 3-continued
Structures of representative matriptase inhibitors
disclosed in U.S. Pat. No. 7,019,019
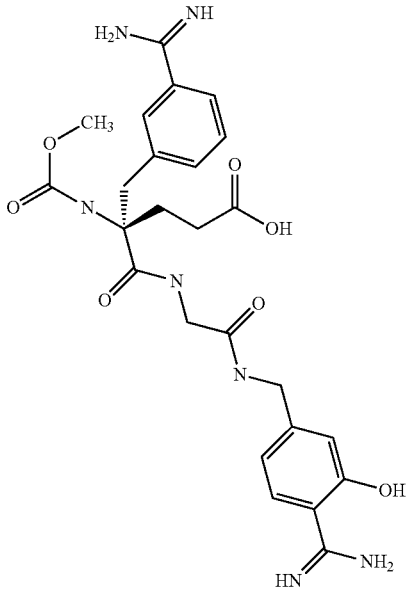 [SMILES: COC(=O)N[C@](CCC(=O)O)(Cc1cccc(C(=N)N)c1)C(=O)NCC(=O)NCc1ccc(C(=N)N)c(O)c1]
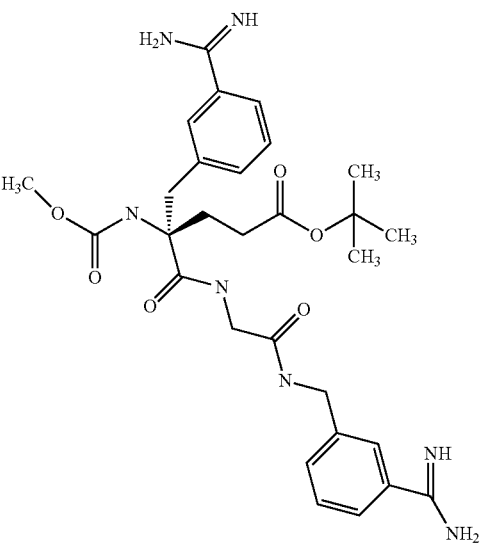 [SMILES: COC(=O)N[C@](CCC(=O)OC(C)(C)C)(Cc1cccc(C(=N)N)c1)C(=O)NCC(=O)NCc1cccc(C(=N)N)c1]
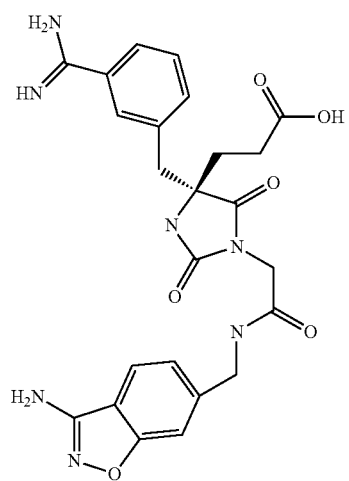 [SMILES: N=C(N)c1cccc(C[C@@]2(CCC(=O)O)NC(=O)N(CC(=O)NCc3ccc4c(N)noc4c3)C2=O)c1]

TABLE 3-continued
Structures of representative matriptase inhibitors disclosed in U.S. Pat. No. 7,019,019
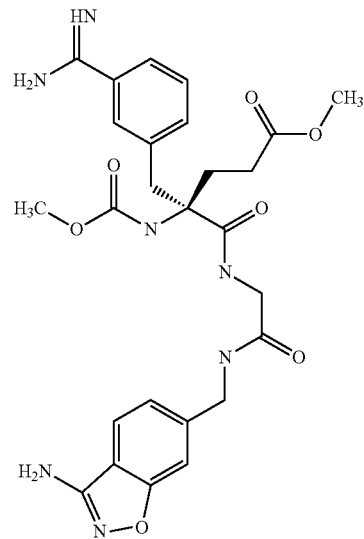
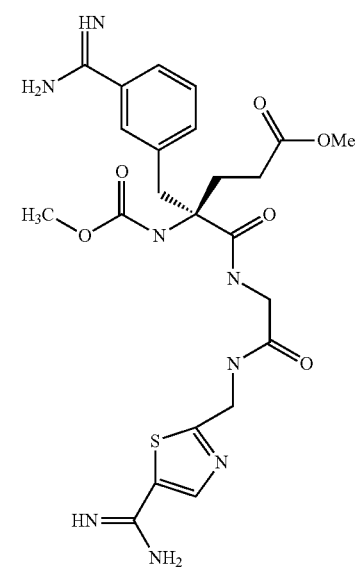 [SMILES: COC(=O)CC[C@](Cc1cccc(C(=N)N)c1)(NC(=O)OC)C(=O)NCC(=O)NCc1ncc(C(=N)N)s1]
TABLE 3-continued
Structures of representative matriptase inhibitors disclosed in U.S. Pat. No. 7,019,019
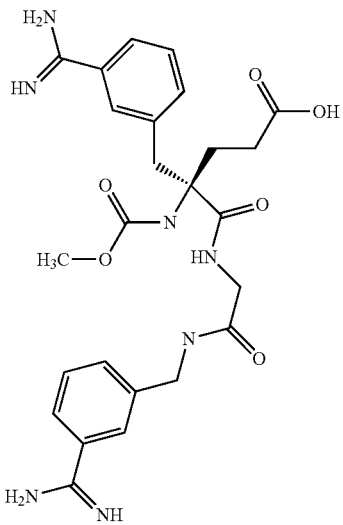 [SMILES: COC(=O)N[C@](CCC(=O)O)(Cc1cccc(C(=N)N)c1)C(=O)NCC(=O)NCc1cccc(C(=N)N)c1]
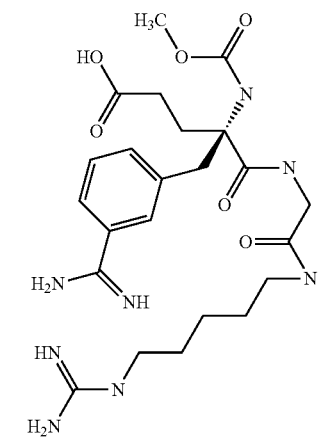
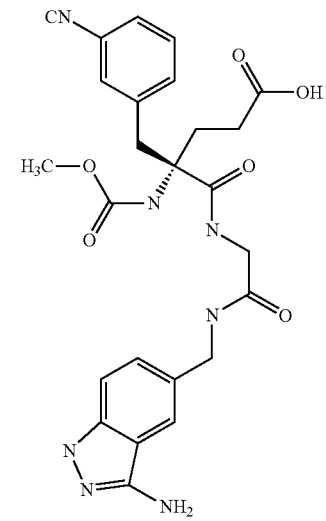

TABLE 3-continued
Structures of representative matriptase inhibitors disclosed in U.S. Pat. No. 7,019,019
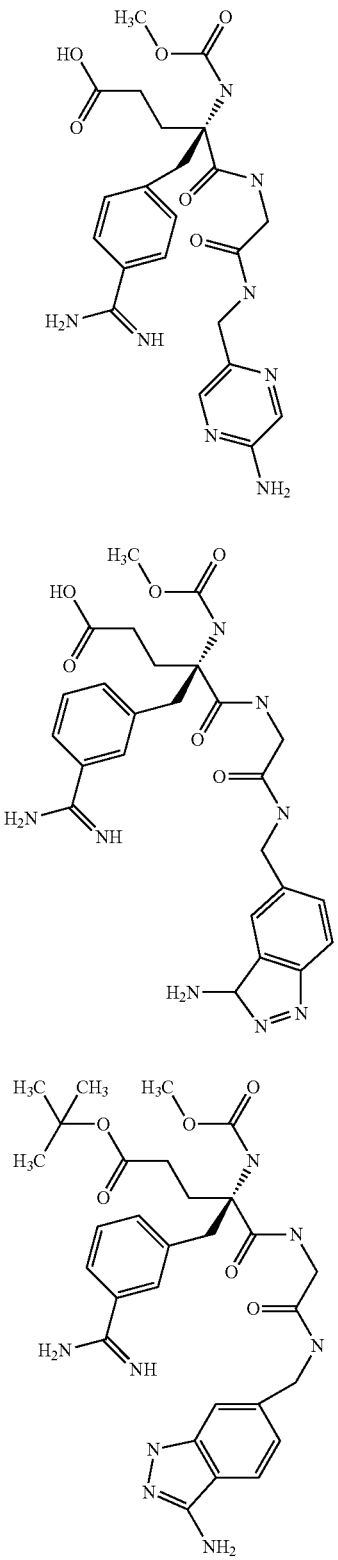
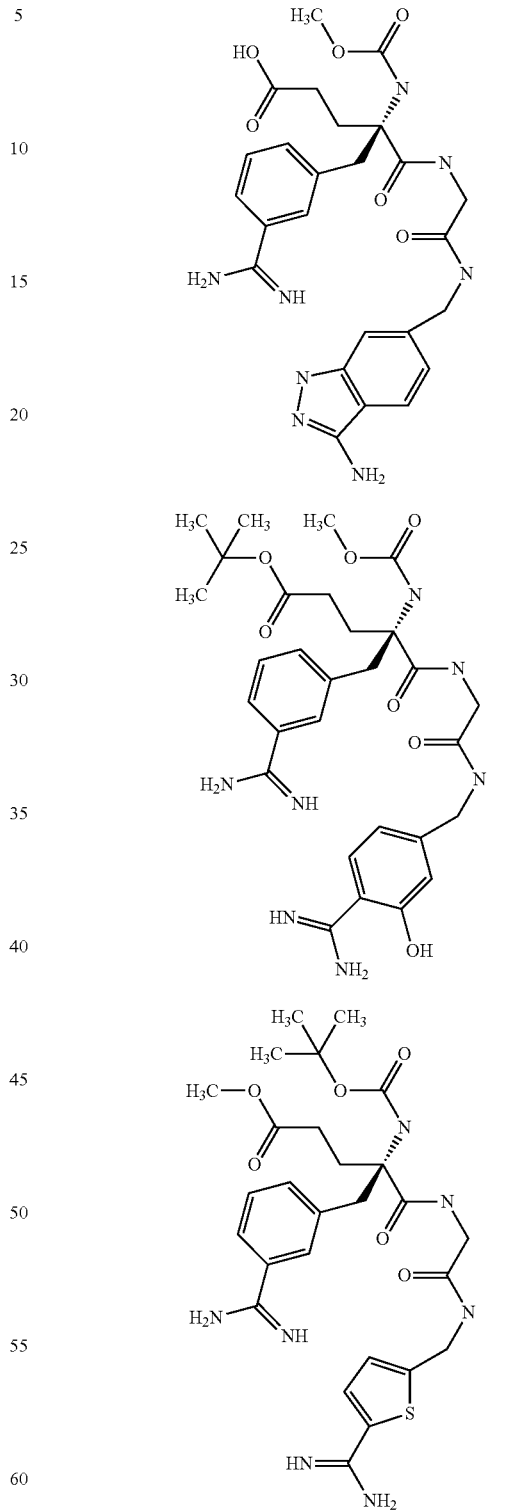
Matriptase inhibitors are also disclosed in PCT publication No. WO 2002/020475. The structures of representative examples of inhibitors disclosed therein are depicted in Table 4 below.

TABLE 4
Structures of representative matriptase inhibitors disclosed in WO 2002/020475
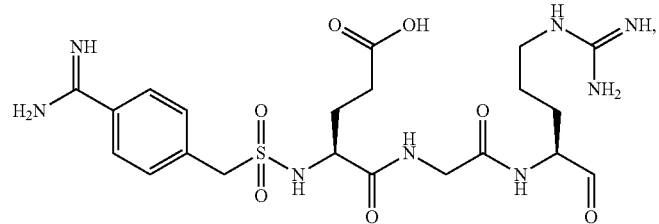 [SMILES: N=C(N)NCCC[C@@H](C=O)NC(=O)CNC(=O)[C@H](CCC(=O)O)NS(=O)(=O)Cc1ccc(C(=N)N)cc1]
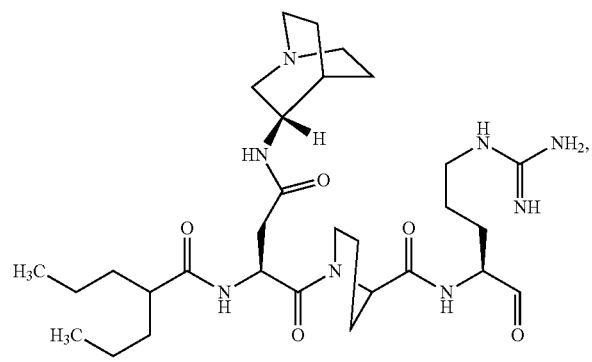 [SMILES: CCCC(CCC)C(=O)N[C@@H](CC(=O)N[C@H]1CN2CCC1CC2)C(=O)N1CCCC1C(=O)N[C@H](C=O)CCCNC(=N)N]
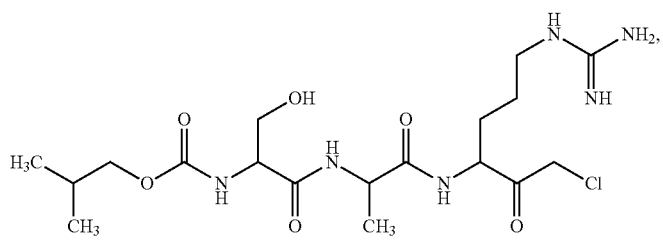 [SMILES: CC(C)COC(=O)NC(CO)C(=O)NC(C)C(=O)NC(CCCNC(=N)N)C(=O)CCl]
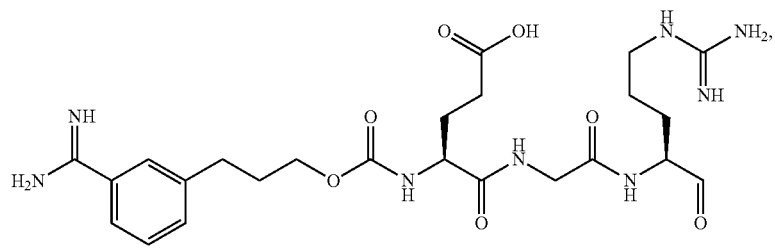 [SMILES: N=C(N)NCCC[C@@H](C=O)NC(=O)CNC(=O)[C@H](CCC(=O)O)NC(=O)OCCCc1cccc(C(=N)N)c1]
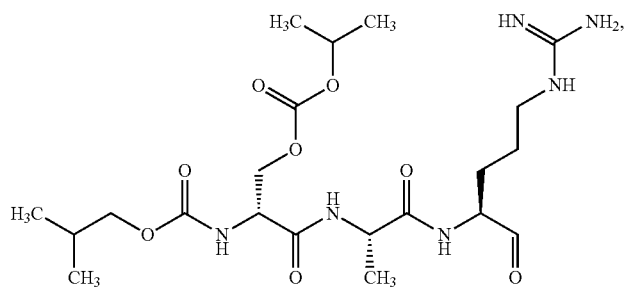 [SMILES: CC(C)COC(=O)N[C@H](COC(=O)OC(C)C)C(=O)N[C@@H](C)C(=O)N[C@H](C=O)CCCNC(=N)N]

TABLE 4-continued
Structures of representative matriptase inhibitors disclosed in WO 2002/020475
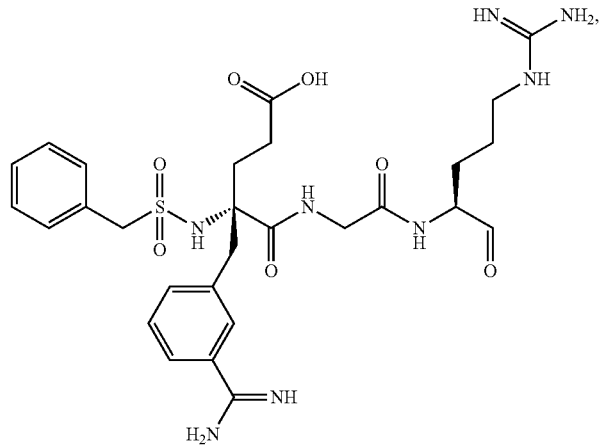 [SMILES: N=C(N)NCCC[C@@H](C=O)NC(=O)CNC(=O)[C@](CCC(=O)O)(Cc1cccc(C(=N)N)c1)NS(=O)(=O)Cc1ccccc1]
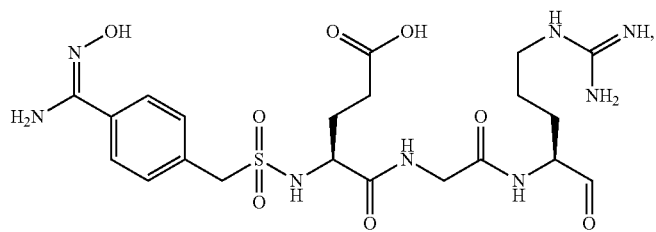 [SMILES: N=C(N)NCCC[C@@H](C=O)NC(=O)CNC(=O)[C@H](CCC(=O)O)NS(=O)(=O)Cc1ccc(/C(N)=N\O)cc1]
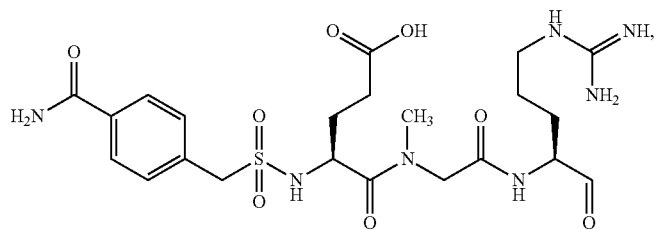 [SMILES: CN(CC(=O)N[C@H](C=O)CCCNC(=N)N)C(=O)[C@H](CCC(=O)O)NS(=O)(=O)Cc1ccc(C(N)=O)cc1]
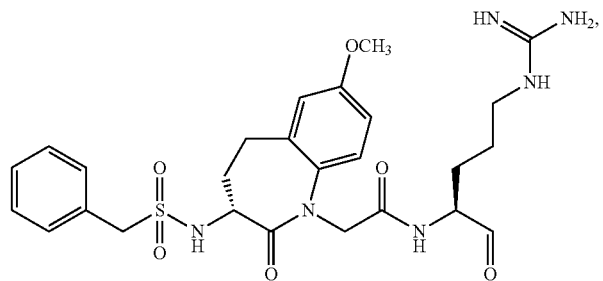 [SMILES: COc1ccc2c(c1)CC[C@@H](NS(=O)(=O)Cc1ccccc1)C(=O)N2CC(=O)N[C@H](C=O)CCCNC(=N)N]
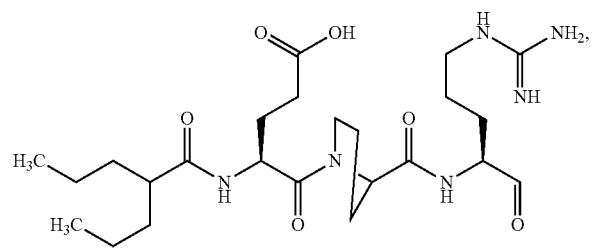 [SMILES: CCCC(CCC)C(=O)N[C@@H](CCC(=O)O)C(=O)N1CCCC1C(=O)N[C@H](C=O)CCCNC(=N)N]

TABLE 4-continued
Structures of representative matriptase inhibitors disclosed in WO 2002/020475
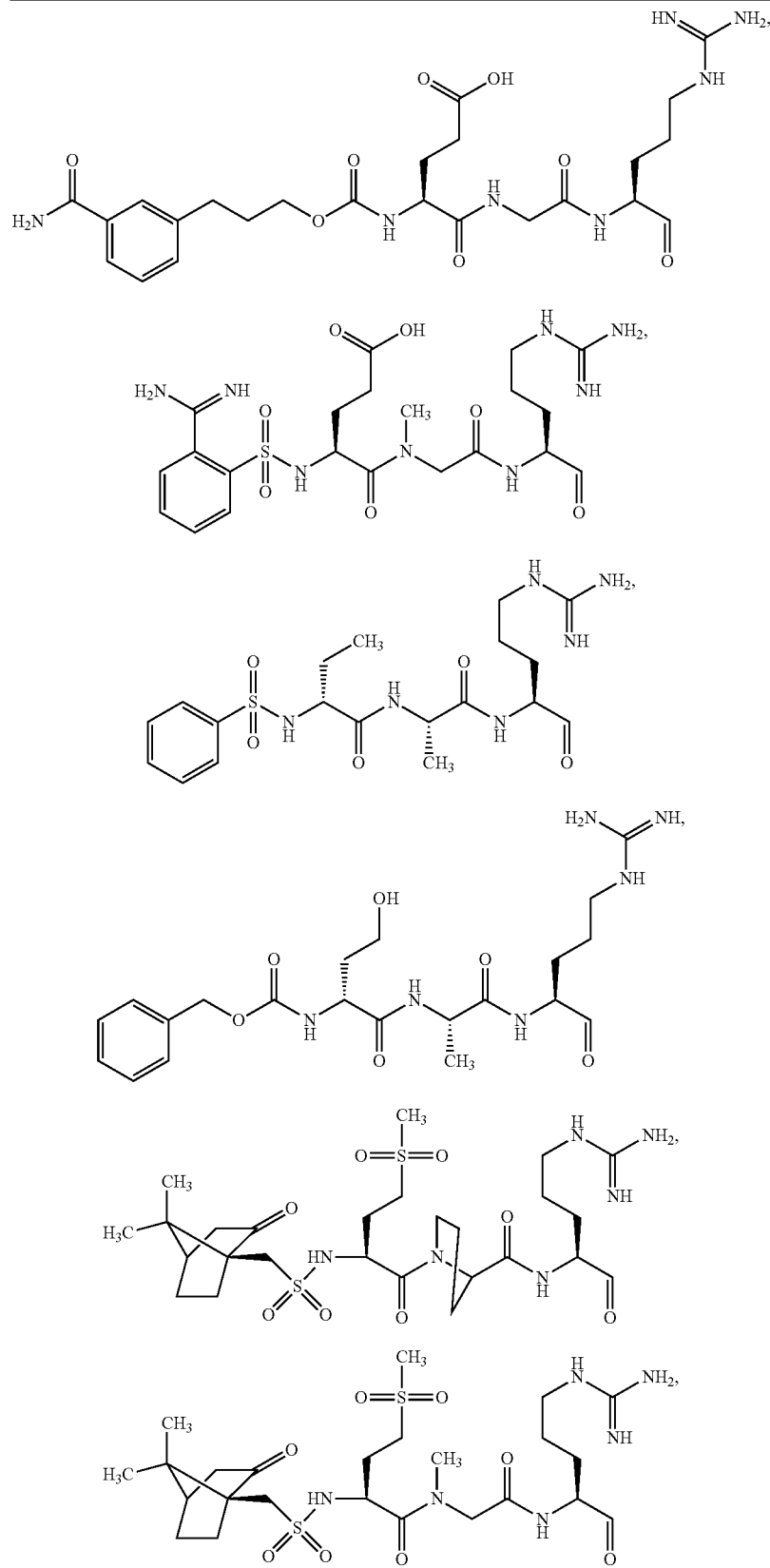

TABLE 4-continued
Structures of representative matriptase inhibitors disclosed in WO 2002/020475
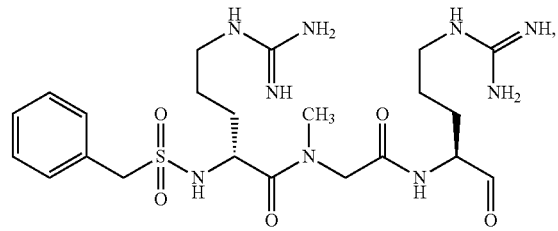 [SMILES: CN(CC(=O)N[C@H](C=O)CCCNC(=N)N)C(=O)[C@@H](CCCNC(=N)N)NS(=O)(=O)Cc1ccccc1]
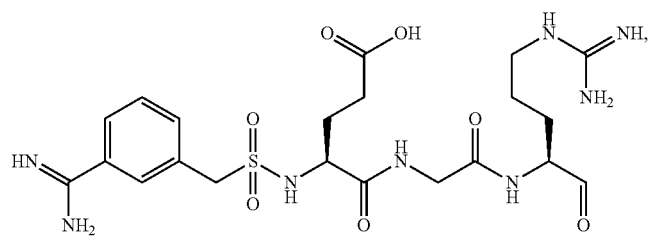 [SMILES: N=C(N)NCCC[C@@H](C=O)NC(=O)CNC(=O)[C@H](CCC(=O)O)NS(=O)(=O)Cc1cccc(C(=N)N)c1]
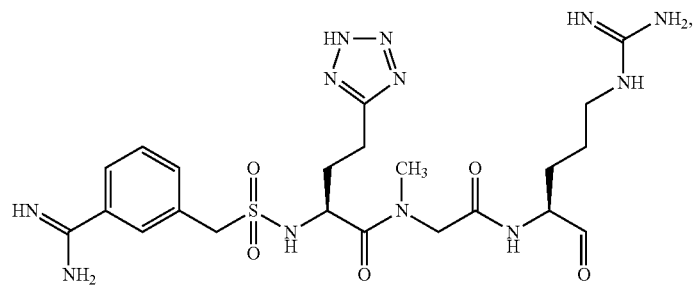 [SMILES: CN(CC(=O)N[C@H](C=O)CCCNC(=N)N)C(=O)[C@H](CCc1nn[nH]n1)NS(=O)(=O)Cc1cccc(C(=N)N)c1]
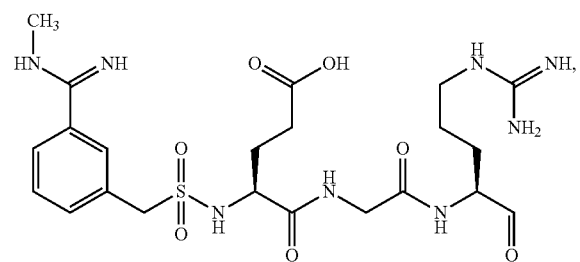 [SMILES: CNC(=N)c1cccc(CS(=O)(=O)N[C@@H](CCC(=O)O)C(=O)NCC(=O)N[C@H](C=O)CCCNC(=N)N)c1]
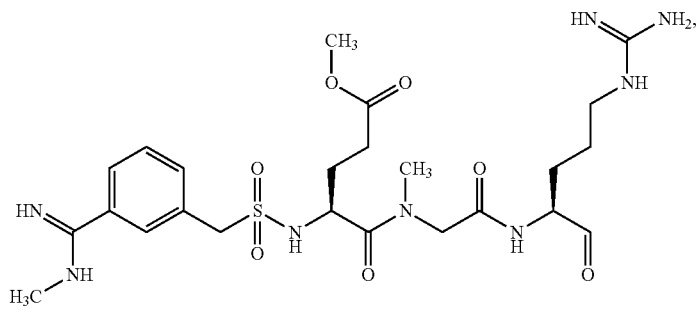 [SMILES: CNC(=N)c1cccc(CS(=O)(=O)N[C@@H](CCC(=O)OC)C(=O)N(C)CC(=O)N[C@H](C=O)CCCNC(=N)N)c1]

TABLE 4-continued
Structures of representative matriptase inhibitors disclosed in WO 2002/020475
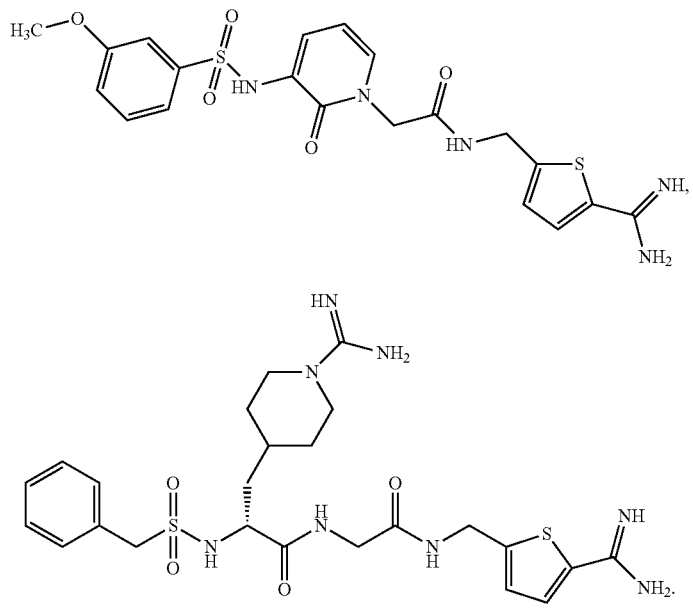
Matriptase inhibitors are also disclosed in U.S. Pat. No. 7,772,251. The structures of representative examples of inhibitors disclosed therein are depicted in Table 5 below.
TABLE 5
Structures of representative matriptase inhibitors disclosed in U.S. Pat. No. 7,772,251
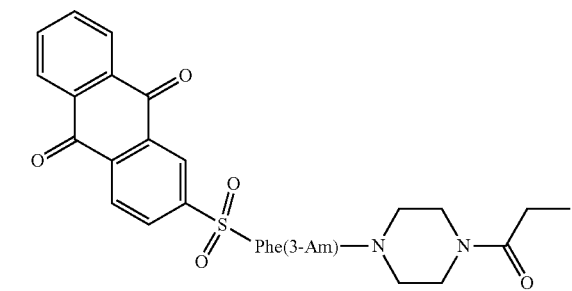
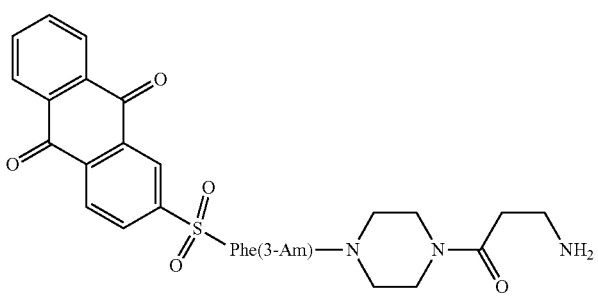

TABLE 5-continued
Structures of representative matriptase inhibitors disclosed in U.S. Pat. No. 7,772,251
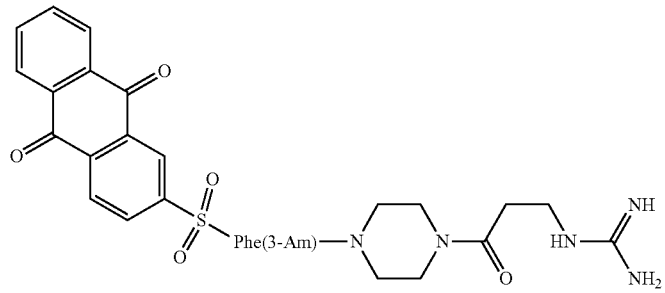
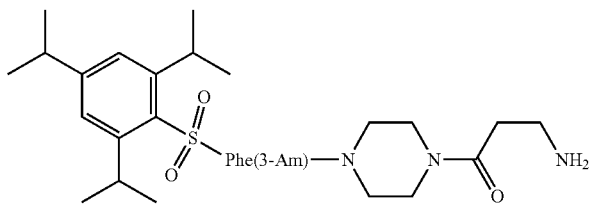
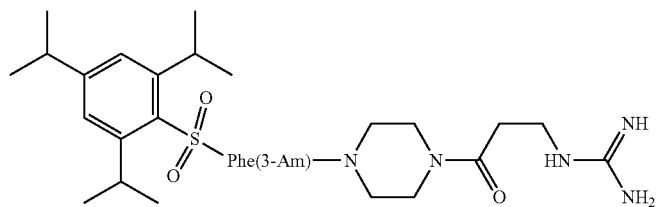
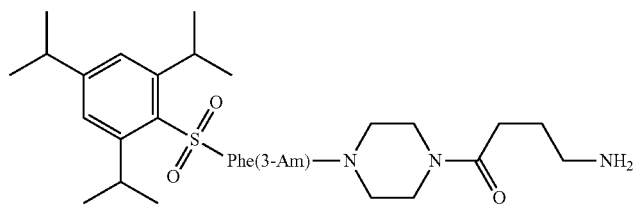
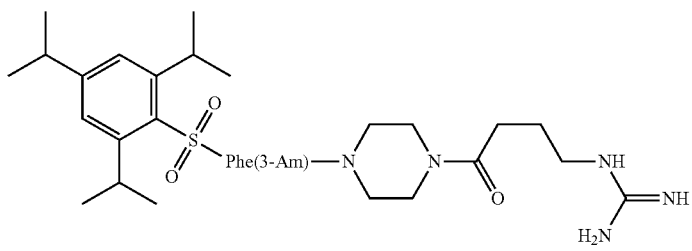
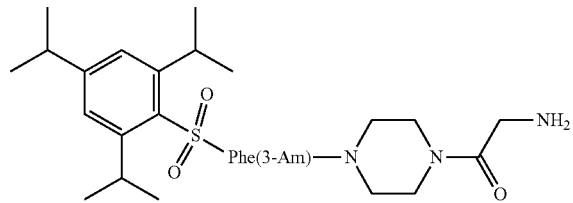
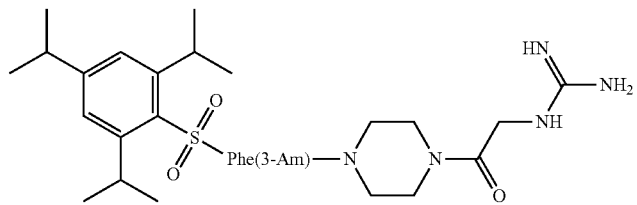

TABLE 5-continued
Structures of representative matriptase inhibitors disclosed in U.S. Pat. No. 7,772,251
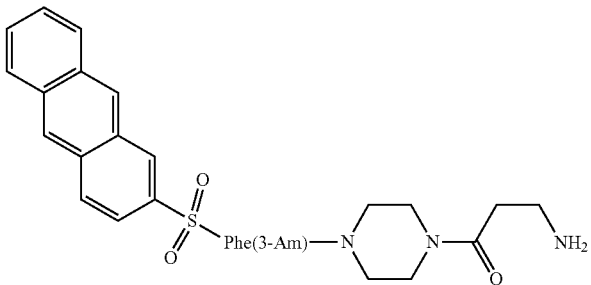
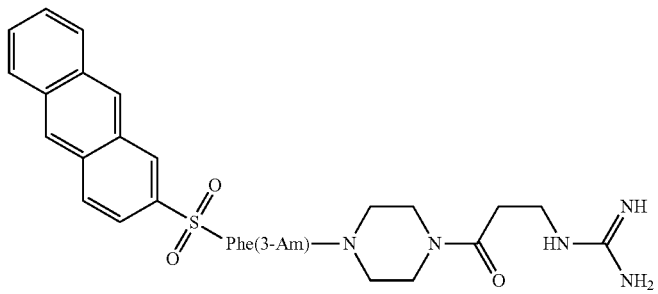
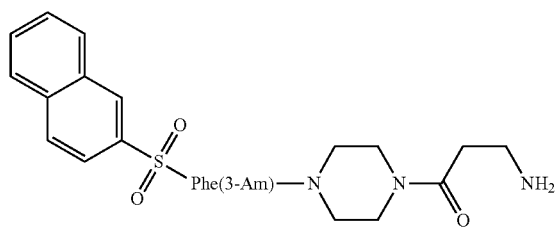
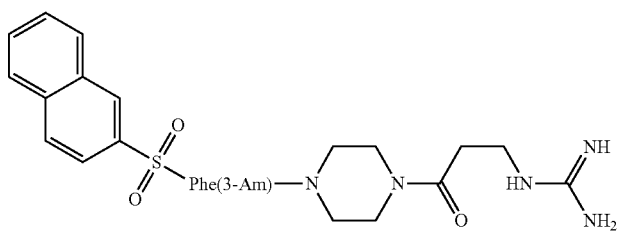
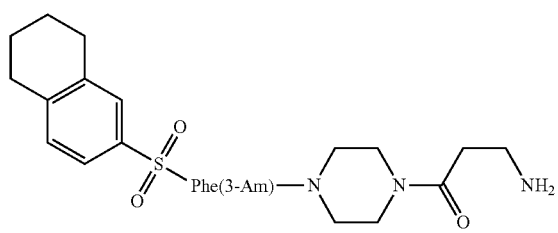
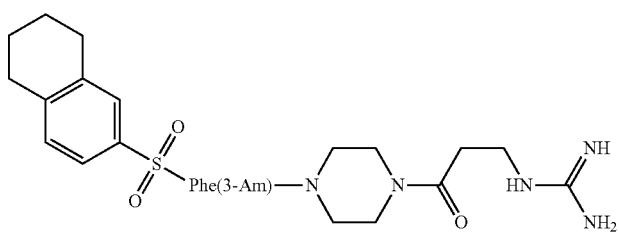

TABLE 5-continued
Structures of representative matriptase inhibitors disclosed in U.S. Pat. No. 7,772,251
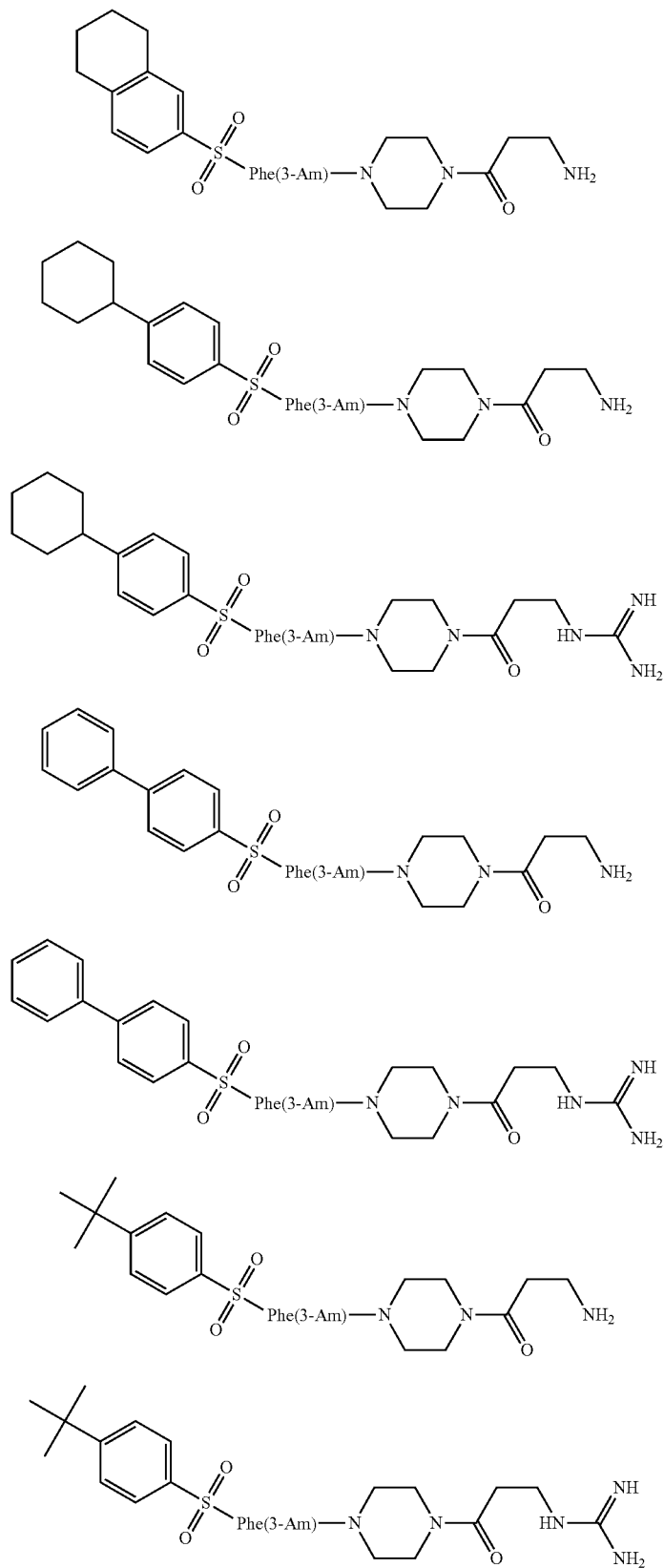

TABLE 5-continued
Structures of representative matriptase inhibitors disclosed in U.S. Pat. No. 7,772,251
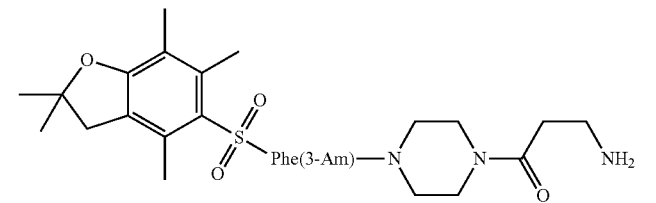
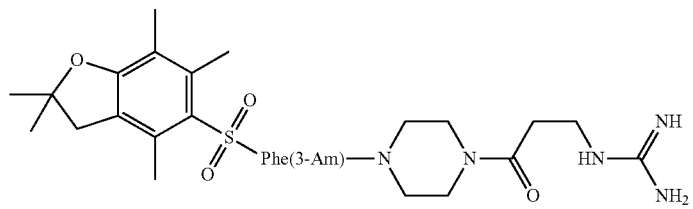
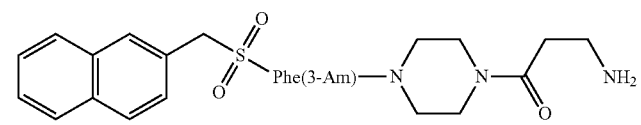
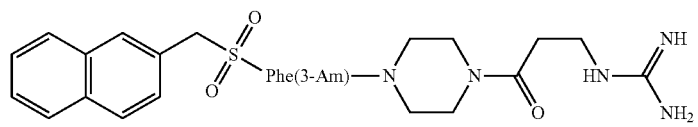
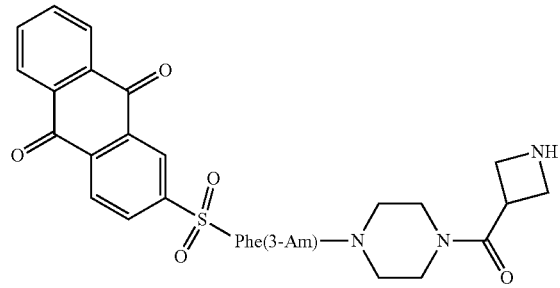
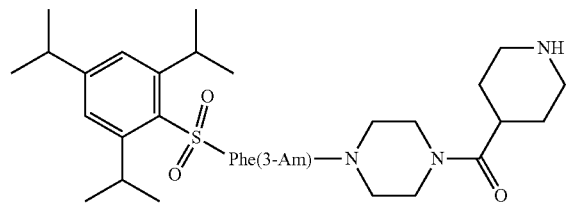
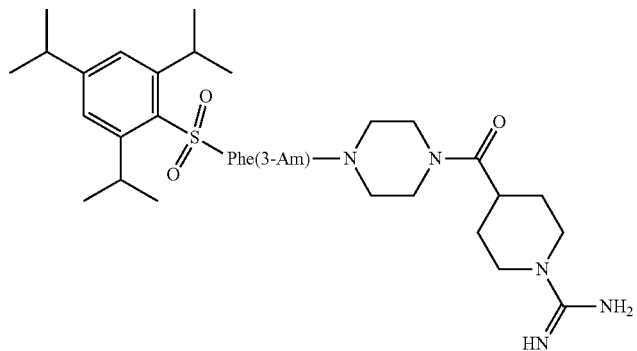

TABLE 5-continued
Structures of representative matriptase inhibitors disclosed in U.S. Pat. No. 7,772,251
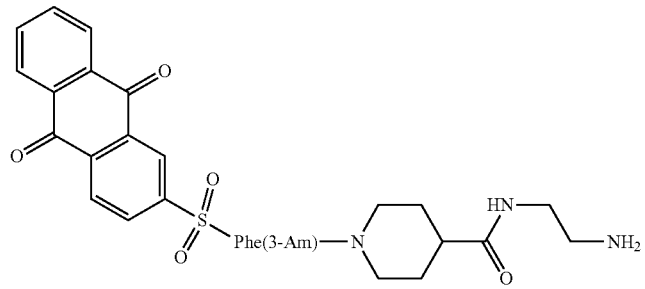
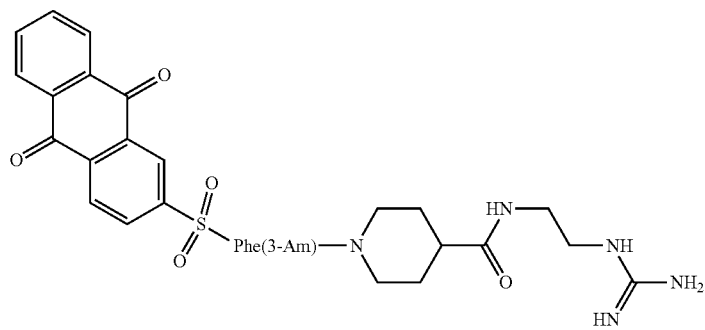
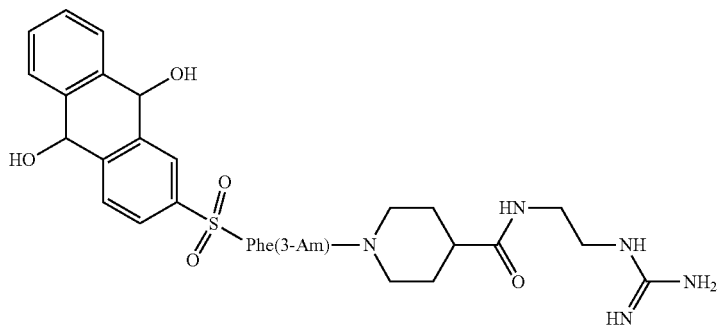
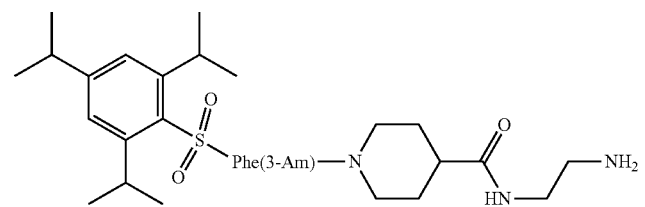
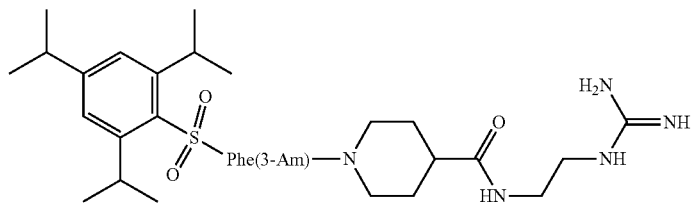
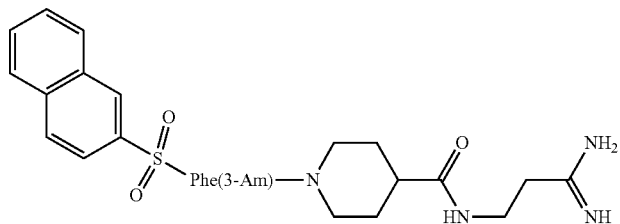

TABLE 5-continued
Structures of representative matriptase inhibitors disclosed in U.S. Pat. No. 7,772,251
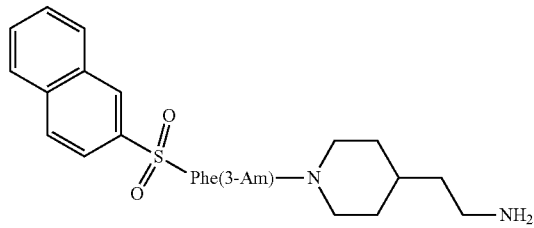
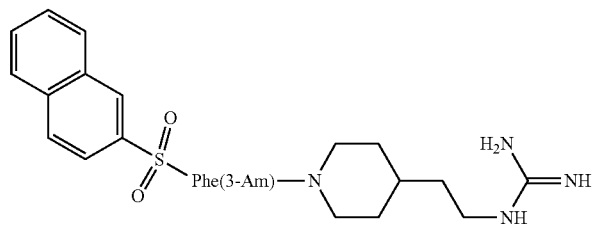
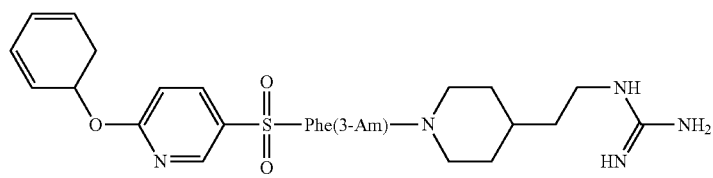
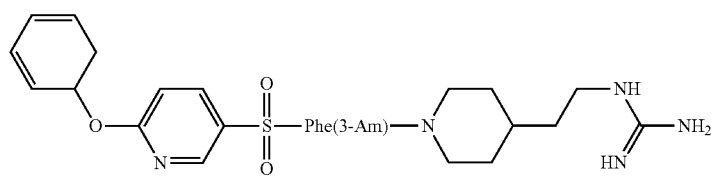
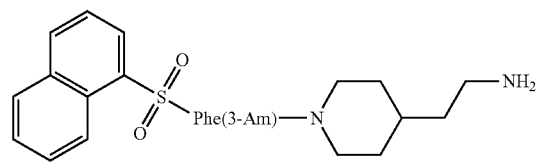
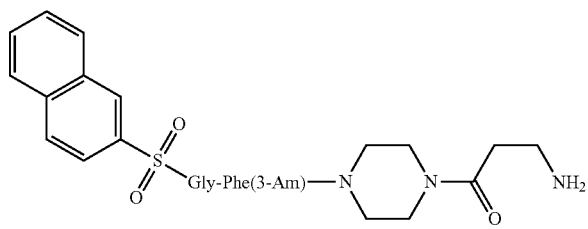
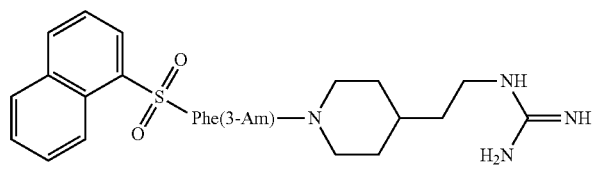

TABLE 5-continued
Structures of representative matriptase inhibitors disclosed in U.S. Pat. No. 7,772,251
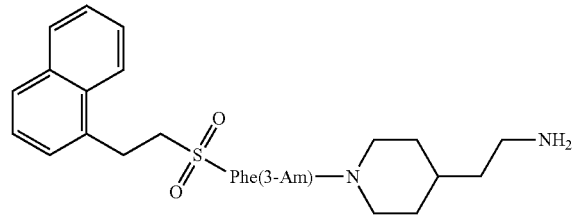
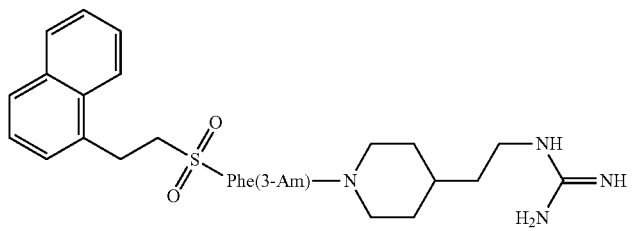
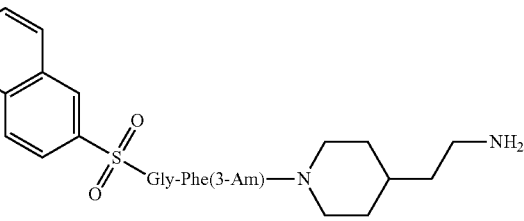
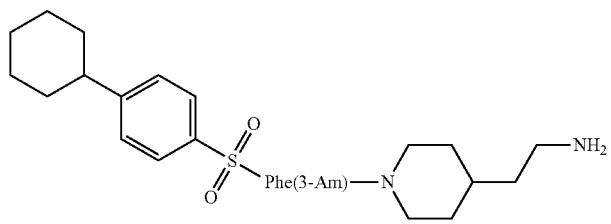
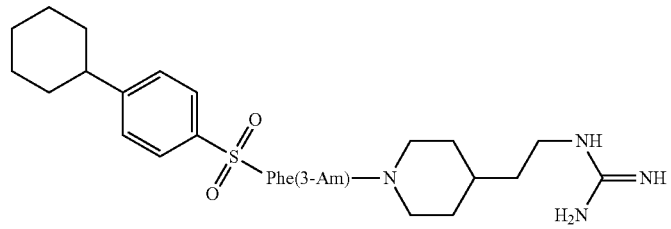
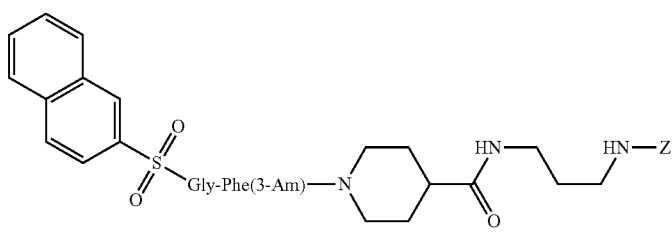

TABLE 5-continued
Structures of representative matriptase inhibitors disclosed in U.S. Pat. No. 7,772,251
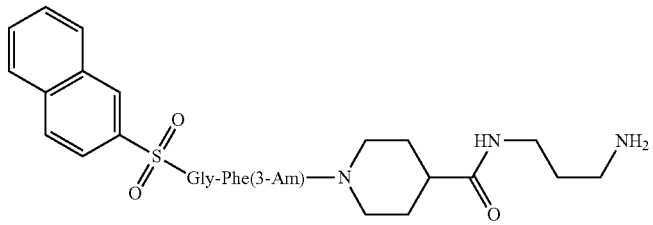
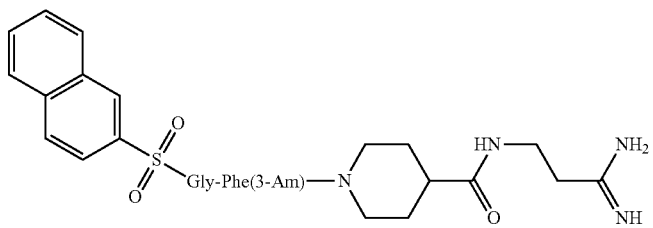
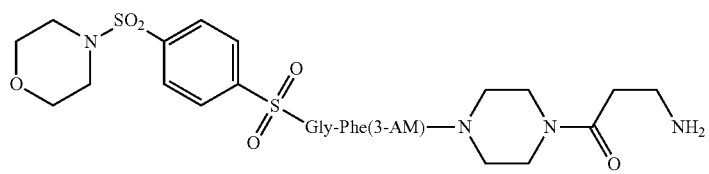
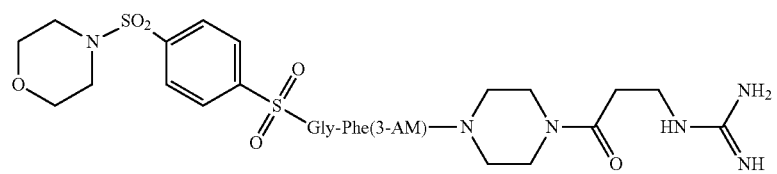
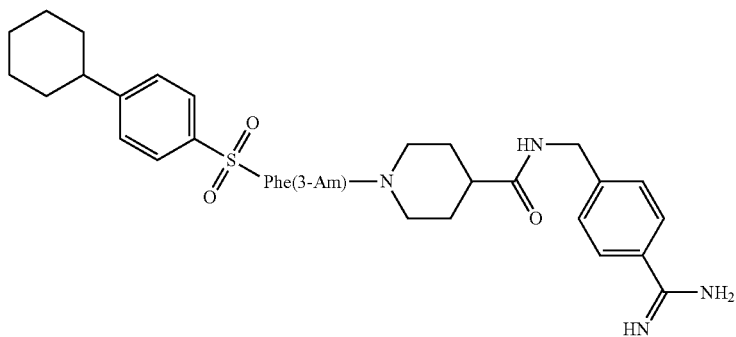
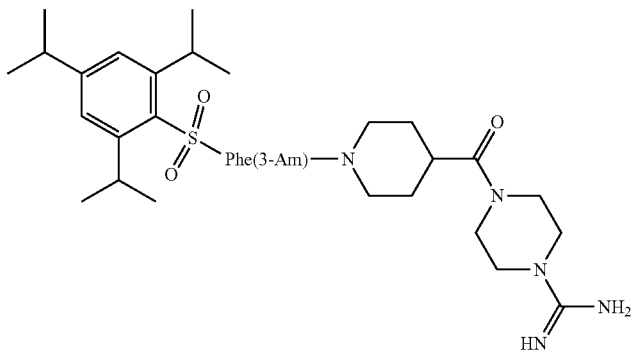

TABLE 5-continued
Structures of representative matriptase inhibitors disclosed in U.S. Pat. No. 7,772,251
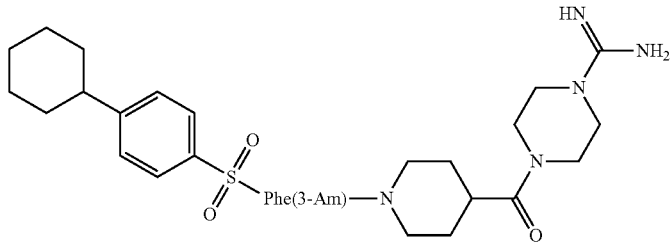
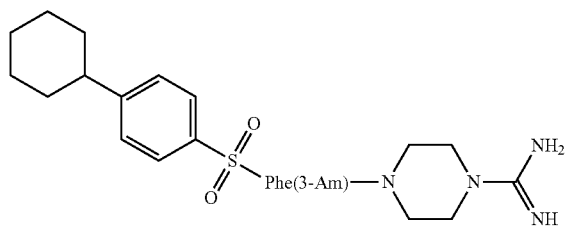
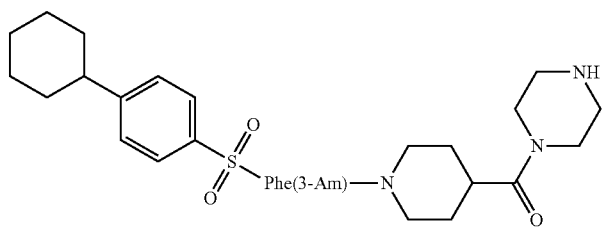
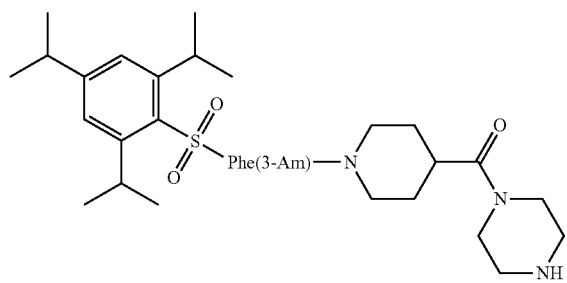
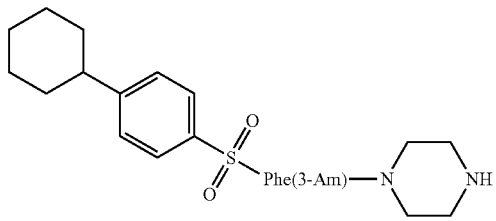
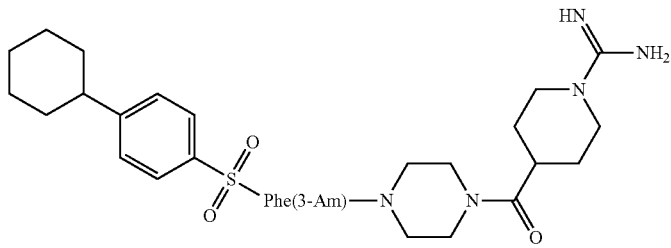

TABLE 5-continued
Structures of representative matriptase inhibitors disclosed in U.S. Pat. No. 7,772,251
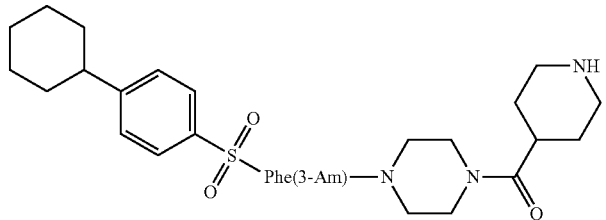
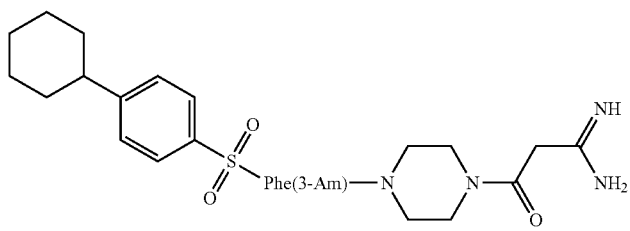
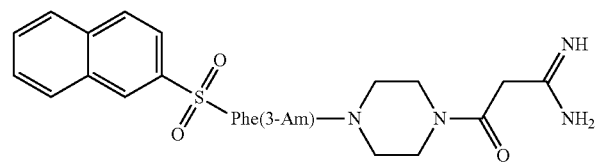
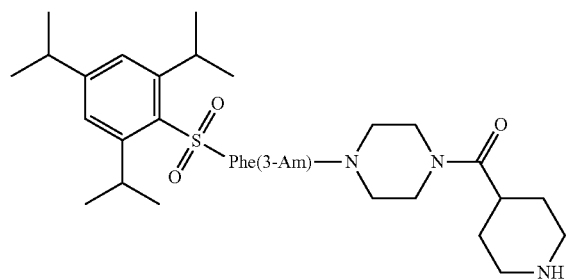
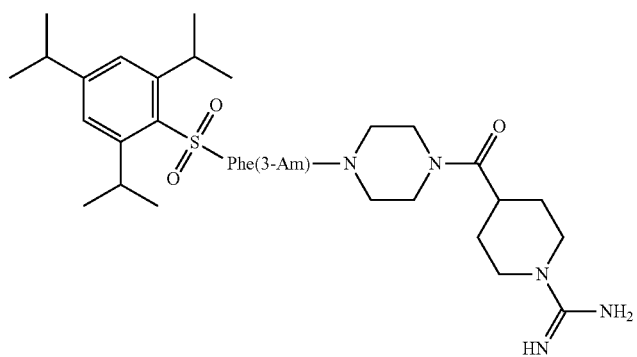

TABLE 5-continued
Structures of representative matriptase inhibitors disclosed in U.S. Pat. No. 7,772,251
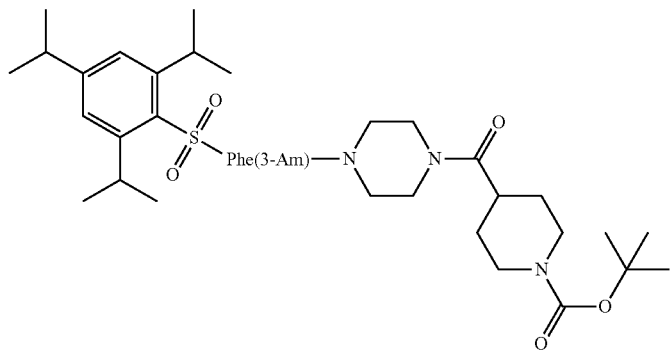
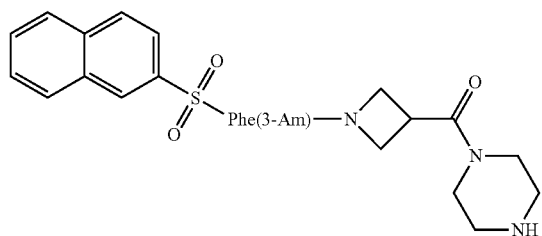
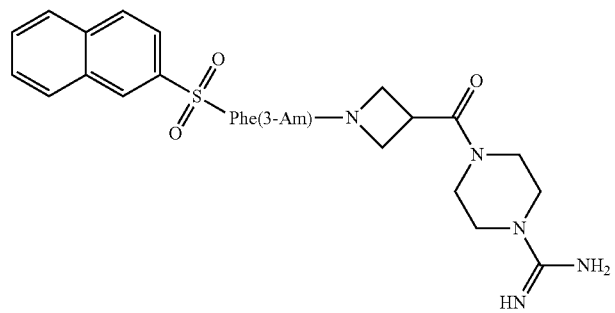
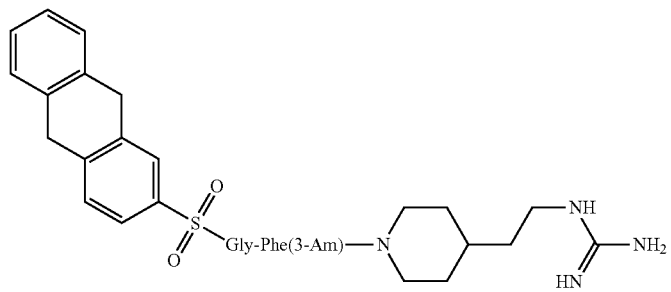
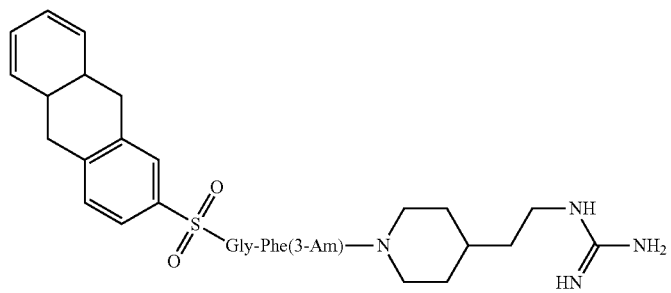

TABLE 5-continued
Structures of representative matriptase inhibitors disclosed in U.S. Pat. No. 7,772,251
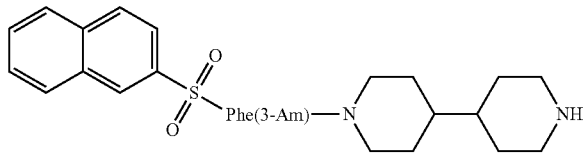
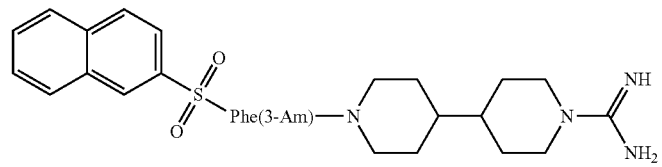
Matriptase inhibitors are also disclosed in US Patent Publication No. 2010/0305090. The structures of representative examples of inhibitors disclosed therein are depicted in Table 6 below.
TABLE 6
Structures of representative matriptase inhibitors disclosed in US Patent Publication No. 2010/0305090
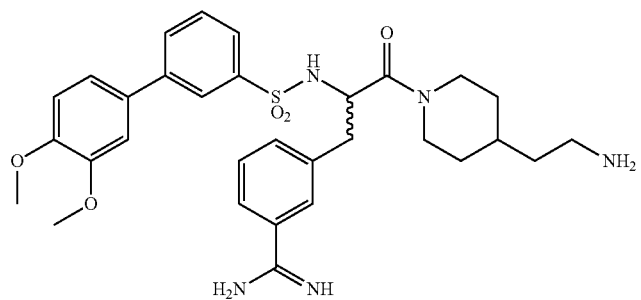 [SMILES: COc1ccc(-c2cccc(S(=O)(=O)NC(Cc3cccc(C(=N)N)c3)C(=O)N3CCC(CCN)CC3)c2)cc1OC]
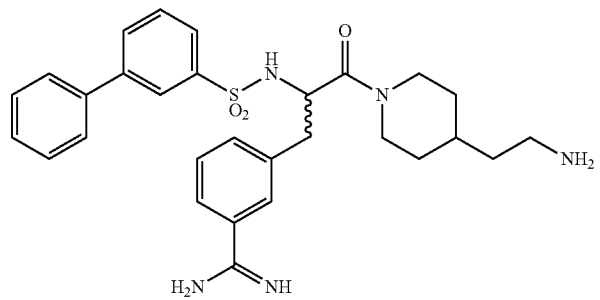 [SMILES: N=C(N)c1cccc(CC(NS(=O)(=O)c2cccc(-c3ccccc3)c2)C(=O)N2CCC(CCN)CC2)c1]
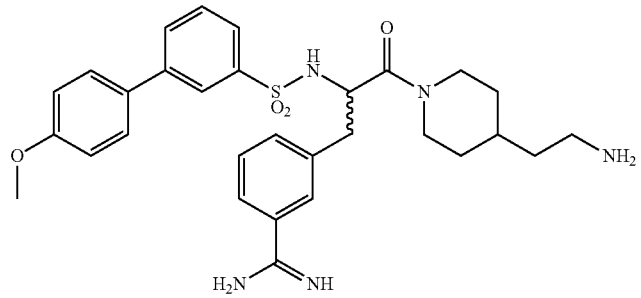 [SMILES: COc1ccc(-c2cccc(S(=O)(=O)NC(Cc3cccc(C(=N)N)c3)C(=O)N3CCC(CCN)CC3)c2)cc1]

TABLE 6-continued
Structures of representative matriptase inhibitors disclosed in US Patent Publication No. 2010/0305090
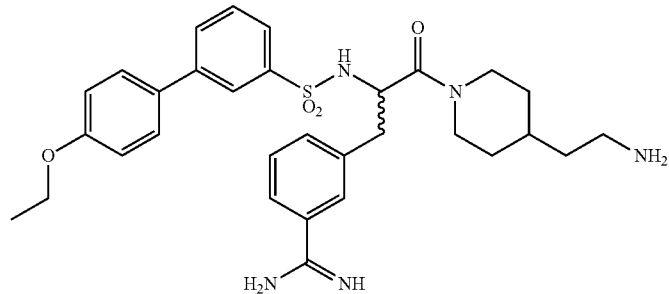 [SMILES: CCOc1ccc(-c2cccc(S(=O)(=O)NC(Cc3cccc(C(=N)N)c3)C(=O)N3CCC(CCN)CC3)c2)cc1]
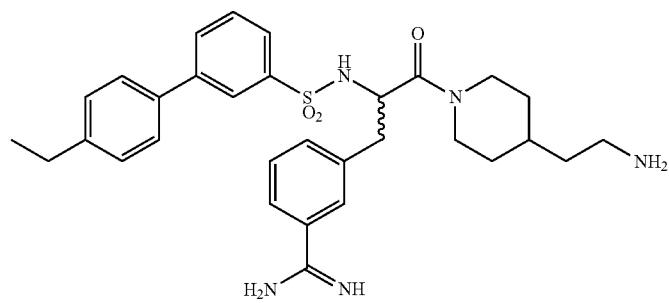 [SMILES: CCc1ccc(-c2cccc(S(=O)(=O)NC(Cc3cccc(C(=N)N)c3)C(=O)N3CCC(CCN)CC3)c2)cc1]
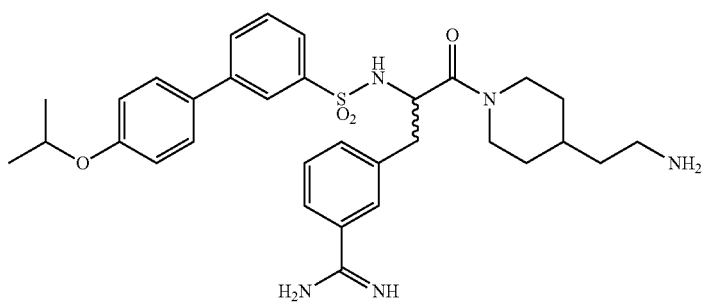 [SMILES: CC(C)Oc1ccc(-c2cccc(S(=O)(=O)NC(Cc3cccc(C(=N)N)c3)C(=O)N3CCC(CCN)CC3)c2)cc1]
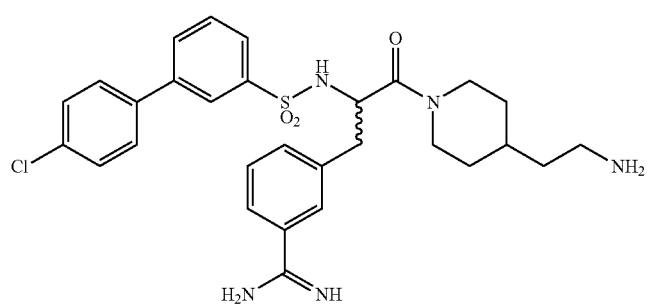 [SMILES: N=C(N)c1cccc(CC(NS(=O)(=O)c2cccc(-c3ccc(Cl)cc3)c2)C(=O)N2CCC(CCN)CC2)c1]
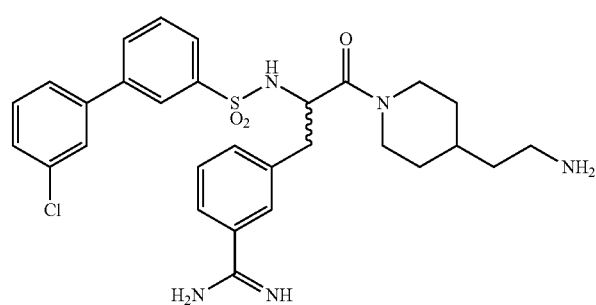 [SMILES: N=C(N)c1cccc(CC(NS(=O)(=O)c2cccc(-c3cccc(Cl)c3)c2)C(=O)N2CCC(CCN)CC2)c1]

TABLE 6-continued
Structures of representative matriptase inhibitors disclosed in US Patent Publication No. 2010/0305090
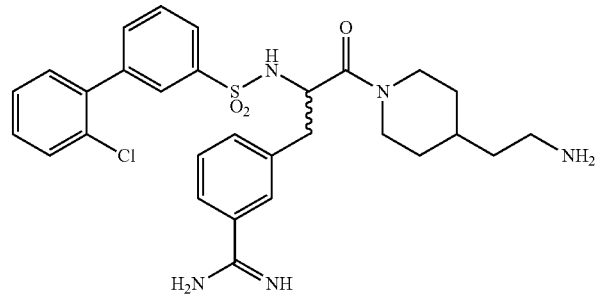 [SMILES: N=C(N)c1cccc(CC(NS(=O)(=O)c2cccc(-c3ccccc3Cl)c2)C(=O)N2CCC(CCN)CC2)c1]
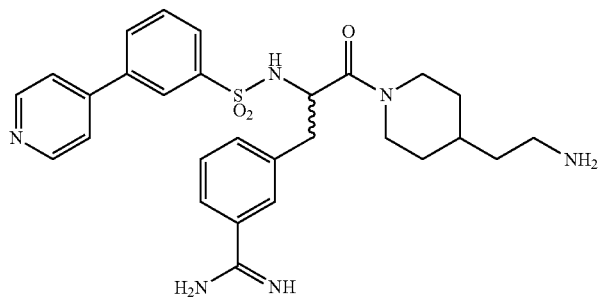
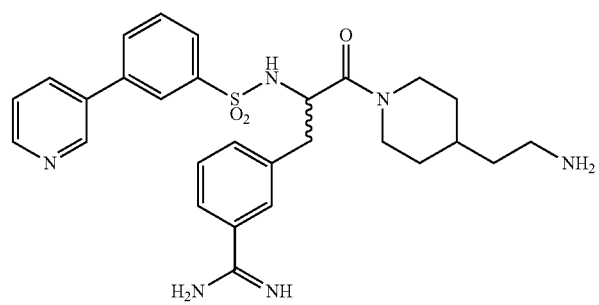 [SMILES: N=C(N)c1cccc(CC(NS(=O)(=O)c2cccc(-c3cccnc3)c2)C(=O)N2CCC(CCN)CC2)c1]
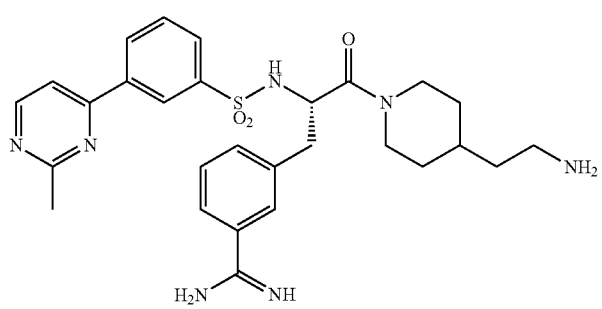 [SMILES: Cc1nccc(-c2cccc(S(=O)(=O)N[C@@H](Cc3cccc(C(=N)N)c3)C(=O)N3CCC(CCN)CC3)c2)n1]
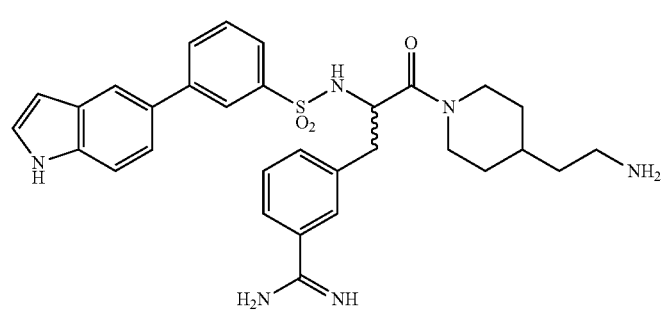 [SMILES: N=C(N)c1cccc(CC(NS(=O)(=O)c2cccc(-c3ccc4[nH]ccc4c3)c2)C(=O)N2CCC(CCN)CC2)c1]

TABLE 6-continued
Structures of representative matriptase inhibitors disclosed in US Patent Publication No. 2010/0305090
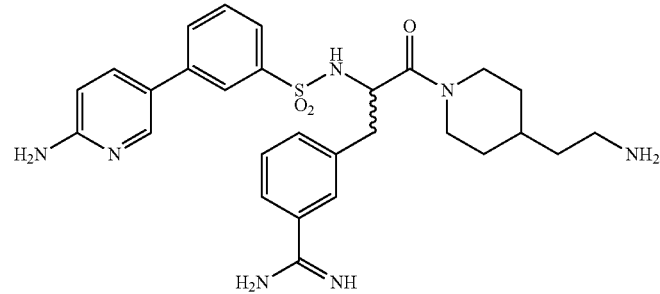 [SMILES: N=C(N)c1cccc(CC(NS(=O)(=O)c2cccc(-c3ccc(N)nc3)c2)C(=O)N2CCC(CCN)CC2)c1]
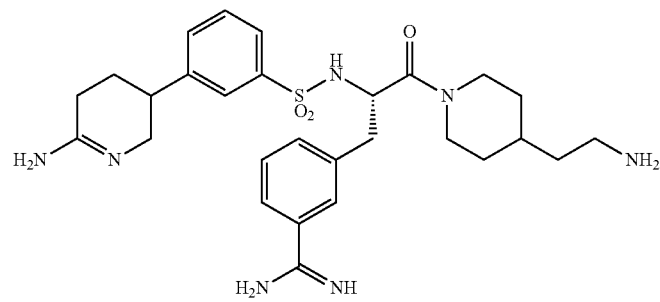 [SMILES: N=C(N)c1cccc(C[C@H](NS(=O)(=O)c2cccc(C3CCC(N)=NC3)c2)C(=O)N2CCC(CCN)CC2)c1]
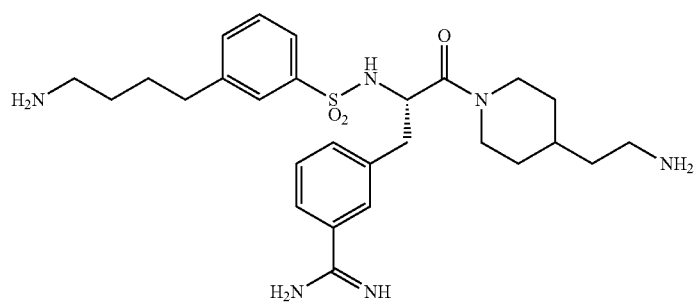 [SMILES: N=C(N)c1cccc(C[C@H](NS(=O)(=O)c2cccc(CCCCN)c2)C(=O)N2CCC(CCN)CC2)c1]
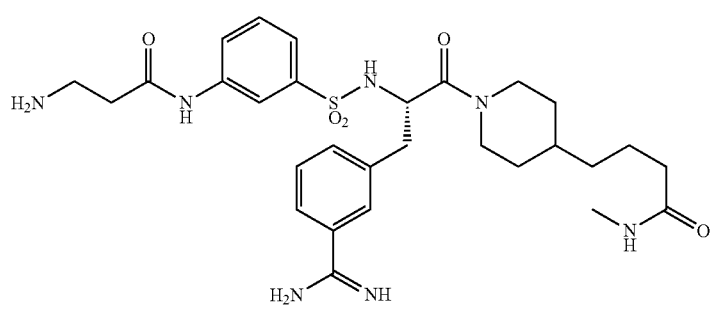 [SMILES: CNC(=O)CCCC1CCN(C(=O)[C@H](Cc2cccc(C(=N)N)c2)NS(=O)(=O)c2cccc(NC(=O)CCN)c2)CC1]
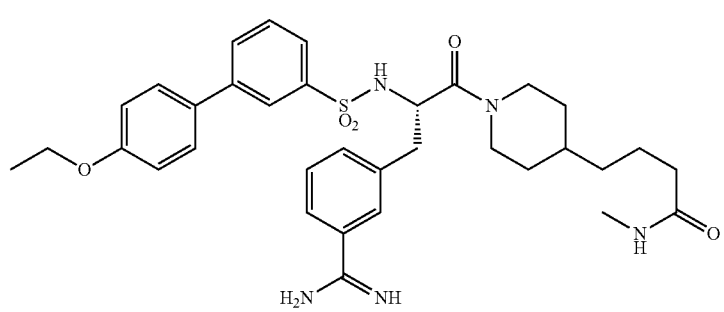 [SMILES: CCOc1ccc(-c2cccc(S(=O)(=O)N[C@@H](Cc3cccc(C(=N)N)c3)C(=O)N3CCC(CCCC(=O)NC)CC3)c2)cc1]

TABLE 6-continued
Structures of representative matriptase inhibitors disclosed in US Patent Publication No. 2010/0305090
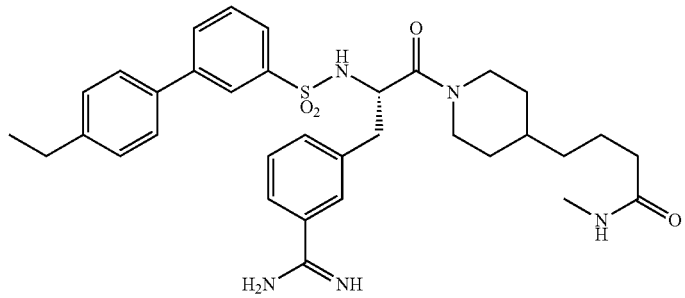 [SMILES: CCc1ccc(-c2cccc(S(=O)(=O)N[C@@H](Cc3cccc(C(=N)N)c3)C(=O)N3CCC(CCCC(=O)NC)CC3)c2)cc1]
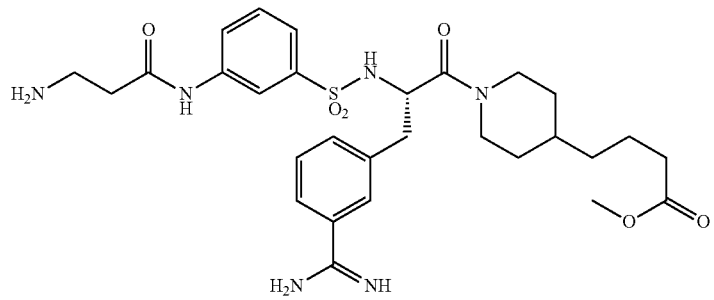 [SMILES: COC(=O)CCCC1CCN(C(=O)[C@H](Cc2cccc(C(=N)N)c2)NS(=O)(=O)c2cccc(NC(=O)CCN)c2)CC1]
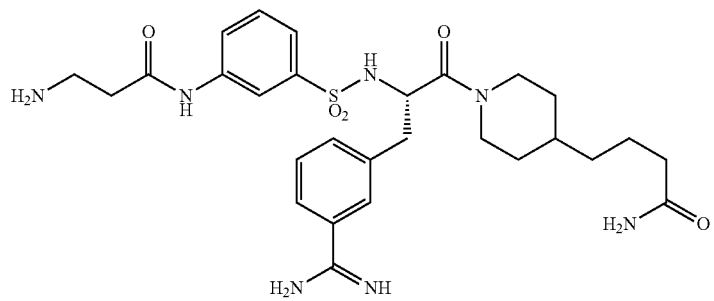 [SMILES: N=C(N)c1cccc(C[C@H](NS(=O)(=O)c2cccc(NC(=O)CCN)c2)C(=O)N2CCC(CCCC(N)=O)CC2)c1]
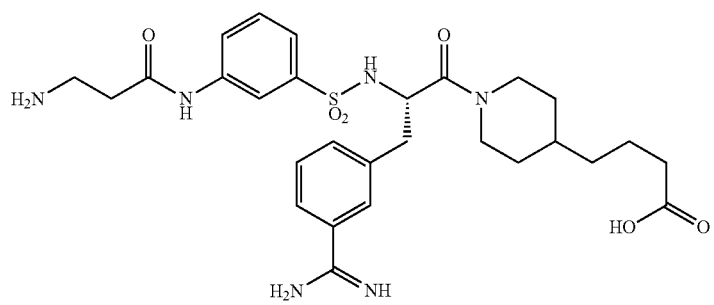 [SMILES: N=C(N)c1cccc(C[C@H](NS(=O)(=O)c2cccc(NC(=O)CCN)c2)C(=O)N2CCC(CCCC(=O)O)CC2)c1]
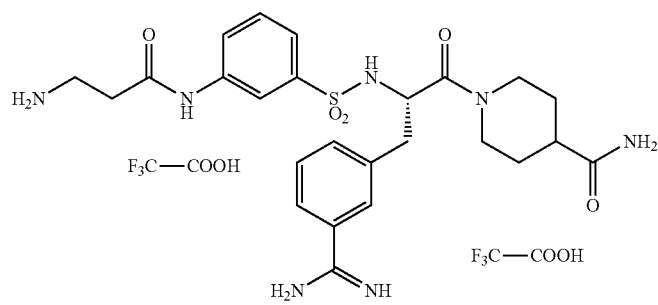 [SMILES: N=C(N)c1cccc(C[C@H](NS(=O)(=O)c2cccc(NC(=O)CCN)c2)C(=O)N2CCC(C(N)=O)CC2)c1 ; O=C(O)C(F)(F)F ; O=C(O)C(F)(F)F]

TABLE 6-continued
Structures of representative matriptase inhibitors disclosed in US Patent Publication No. 2010/0305090
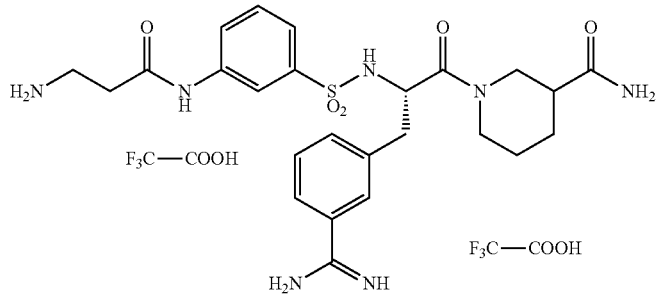 [SMILES: N=C(N)c1cccc(C[C@H](NS(=O)(=O)c2cccc(NC(=O)CCN)c2)C(=O)N2CCCC(C(N)=O)C2)c1 ; O=C(O)C(F)(F)F ; O=C(O)C(F)(F)F]
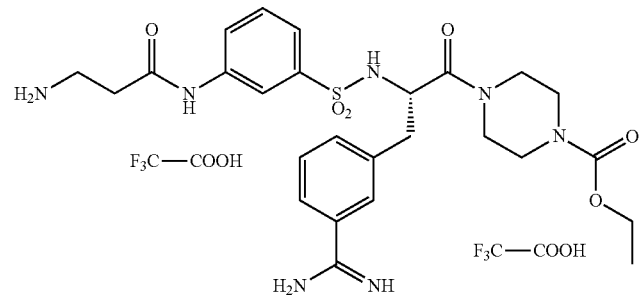 [SMILES: CCOC(=O)N1CCN(C(=O)[C@H](Cc2cccc(C(=N)N)c2)NS(=O)(=O)c2cccc(NC(=O)CCN)c2)CC1 ; O=C(O)C(F)(F)F ; O=C(O)C(F)(F)F]
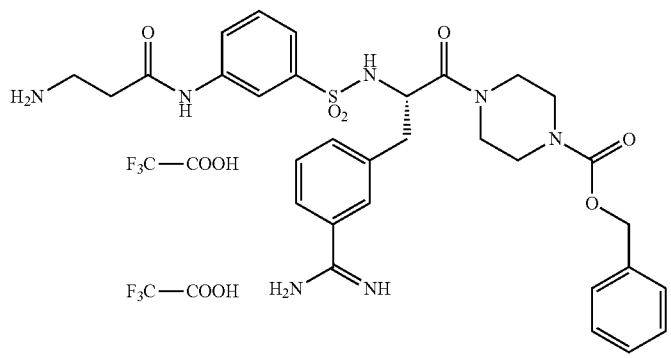 [SMILES: N=C(N)c1cccc(C[C@H](NS(=O)(=O)c2cccc(NC(=O)CCN)c2)C(=O)N2CCN(C(=O)OCc3ccccc3)CC2)c1 ; O=C(O)C(F)(F)F ; O=C(O)C(F)(F)F]
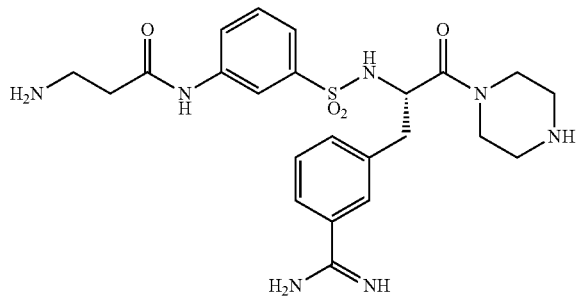 [SMILES: N=C(N)c1cccc(C[C@H](NS(=O)(=O)c2cccc(NC(=O)CCN)c2)C(=O)N2CCNCC2)c1]
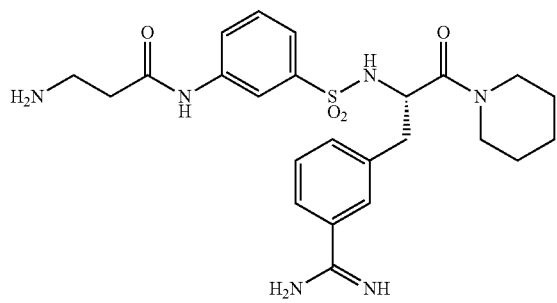 [SMILES: N=C(N)c1cccc(C[C@H](NS(=O)(=O)c2cccc(NC(=O)CCN)c2)C(=O)N2CCCCC2)c1]

TABLE 6-continued
Structures of representative matriptase inhibitors disclosed in US Patent Publication No. 2010/0305090
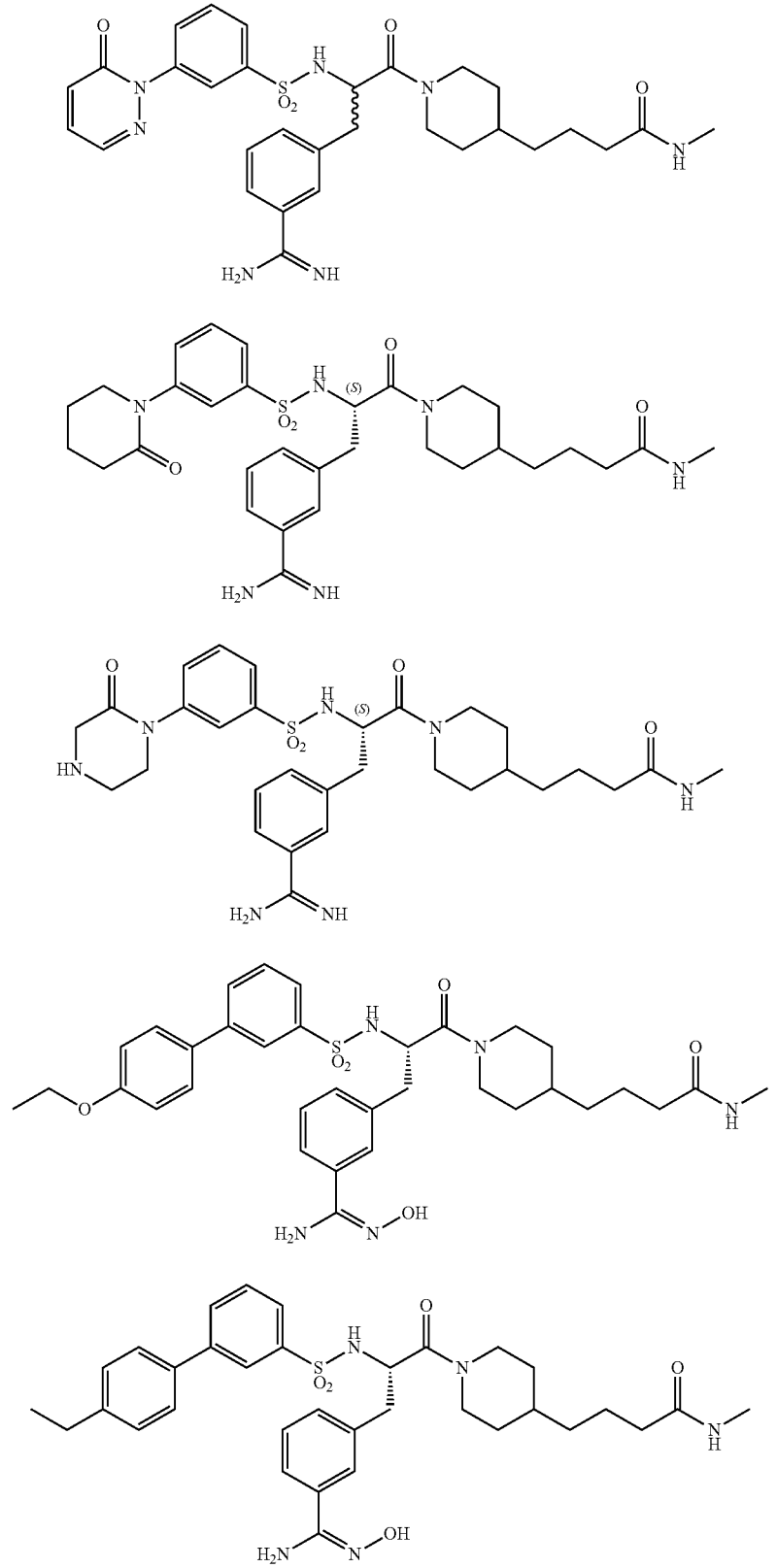

TABLE 6-continued
Structures of representative matriptase inhibitors disclosed in US Patent Publication No. 2010/0305090
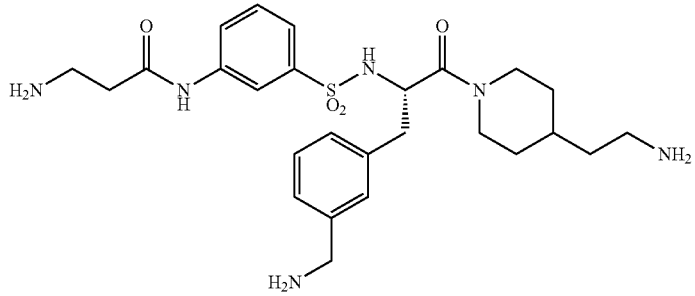 [SMILES: NCCC(=O)Nc1cccc(S(=O)(=O)N[C@@H](Cc2cccc(CN)c2)C(=O)N2CCC(CCN)CC2)c1]
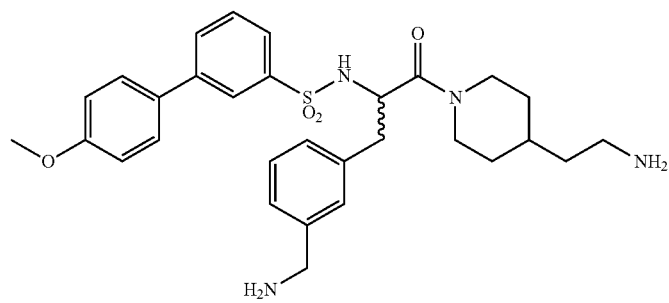 [SMILES: COc1ccc(-c2cccc(S(=O)(=O)NC(Cc3cccc(CN)c3)C(=O)N3CCC(CCN)CC3)c2)cc1]
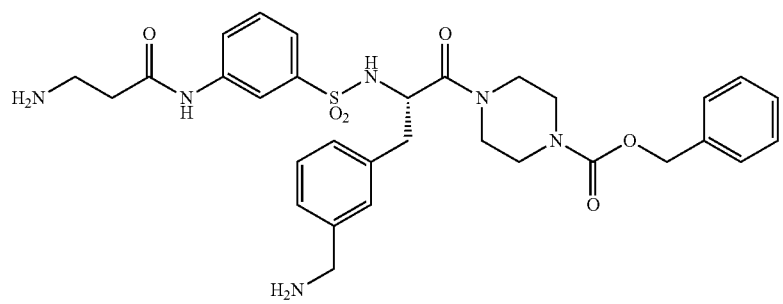 [SMILES: NCCC(=O)Nc1cccc(S(=O)(=O)N[C@@H](Cc2cccc(CN)c2)C(=O)N2CCN(C(=O)OCc3ccccc3)CC2)c1]
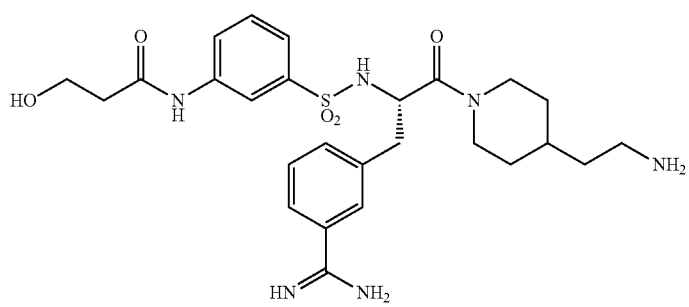 [SMILES: N=C(N)c1cccc(C[C@H](NS(=O)(=O)c2cccc(NC(=O)CCO)c2)C(=O)N2CCC(CCN)CC2)c1]
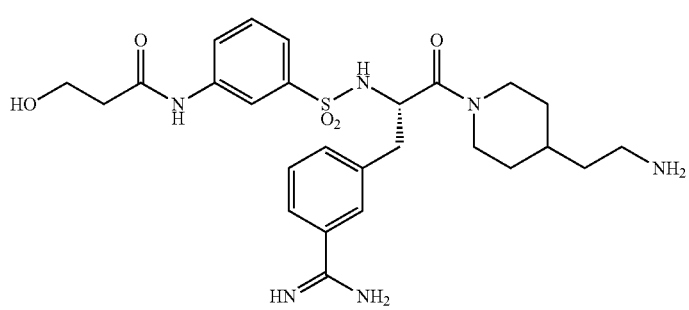 [SMILES: N=C(N)c1cccc(C[C@H](NS(=O)(=O)c2cccc(NC(=O)CCO)c2)C(=O)N2CCC(CCN)CC2)c1]

TABLE 6-continued
Structures of representative matriptase inhibitors disclosed in US Patent Publication No. 2010/0305090
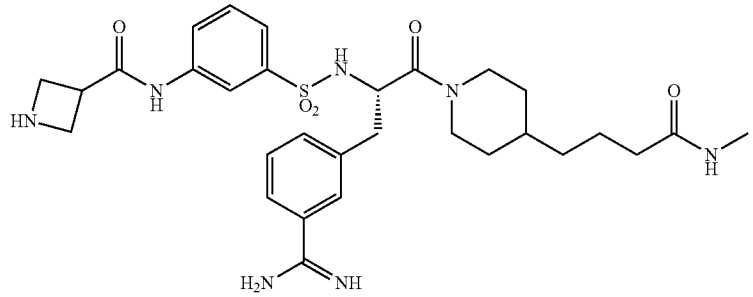 [SMILES: CNC(=O)CCCC1CCN(C(=O)[C@H](Cc2cccc(C(=N)N)c2)NS(=O)(=O)c2cccc(NC(=O)C3CNC3)c2)CC1]
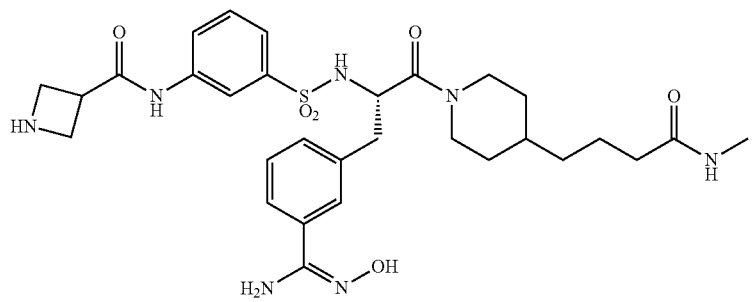 [SMILES: CNC(=O)CCCC1CCN(C(=O)[C@H](Cc2cccc(/C(N)=N\O)c2)NS(=O)(=O)c2cccc(NC(=O)C3CNC3)c2)CC1]
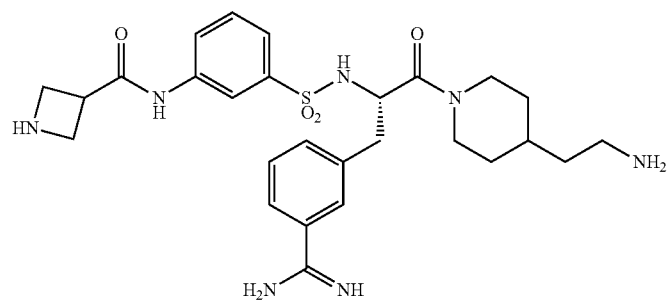 [SMILES: N=C(N)c1cccc(C[C@H](NS(=O)(=O)c2cccc(NC(=O)C3CNC3)c2)C(=O)N2CCC(CCN)CC2)c1]
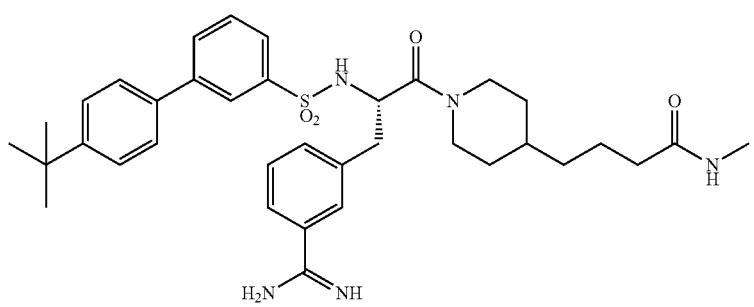 [SMILES: CNC(=O)CCCC1CCN(C(=O)[C@H](Cc2cccc(C(=N)N)c2)NS(=O)(=O)c2cccc(-c3ccc(C(C)(C)C)cc3)c2)CC1]
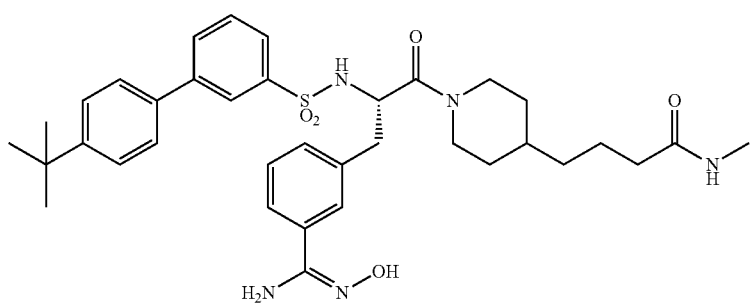 [SMILES: CNC(=O)CCCC1CCN(C(=O)[C@H](Cc2cccc(/C(N)=N\O)c2)NS(=O)(=O)c2cccc(-c3ccc(C(C)(C)C)cc3)c2)CC1]

TABLE 6-continued
Structures of representative matriptase inhibitors disclosed in US Patent Publication No. 2010/0305090
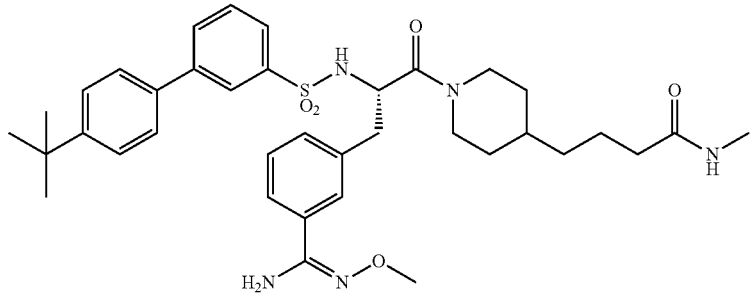 [SMILES: CNC(=O)CCCC1CCN(C(=O)[C@H](Cc2cccc(/C(N)=N\OC)c2)NS(=O)(=O)c2cccc(-c3ccc(C(C)(C)C)cc3)c2)CC1]
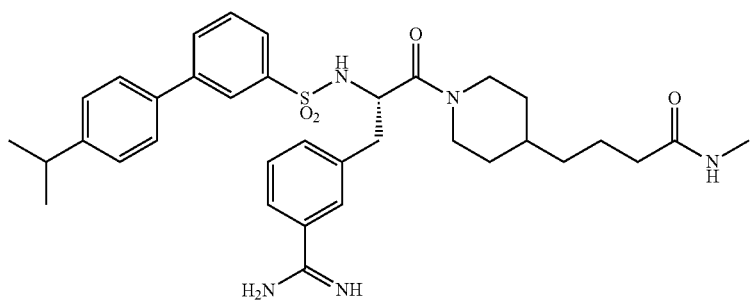 [SMILES: CNC(=O)CCCC1CCN(C(=O)[C@H](Cc2cccc(C(=N)N)c2)NS(=O)(=O)c2cccc(-c3ccc(C(C)C)cc3)c2)CC1]
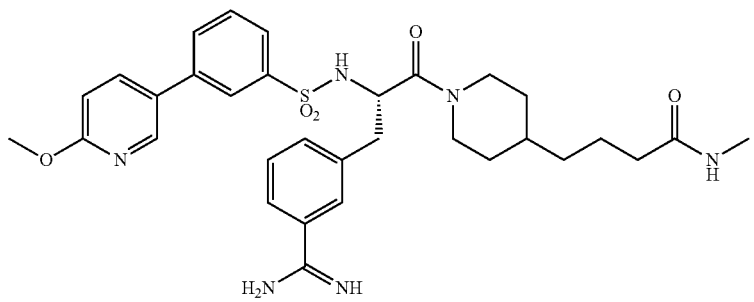
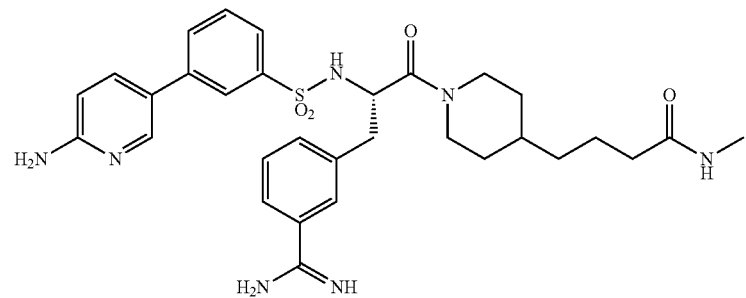 [SMILES: CNC(=O)CCCC1CCN(C(=O)[C@H](Cc2cccc(C(=N)N)c2)NS(=O)(=O)c2cccc(-c3ccc(N)nc3)c2)CC1]
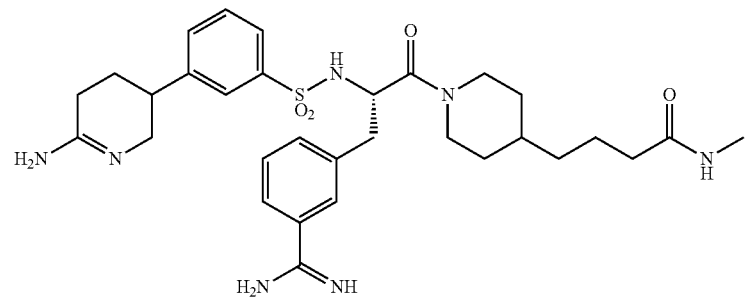 [SMILES: CNC(=O)CCCC1CCN(C(=O)[C@H](Cc2cccc(C(=N)N)c2)NS(=O)(=O)c2cccc(C3CCC(N)=NC3)c2)CC1]

TABLE 6-continued

Structures of representative matriptase inhibitors disclosed in US Patent Publication No. 2010/0305090

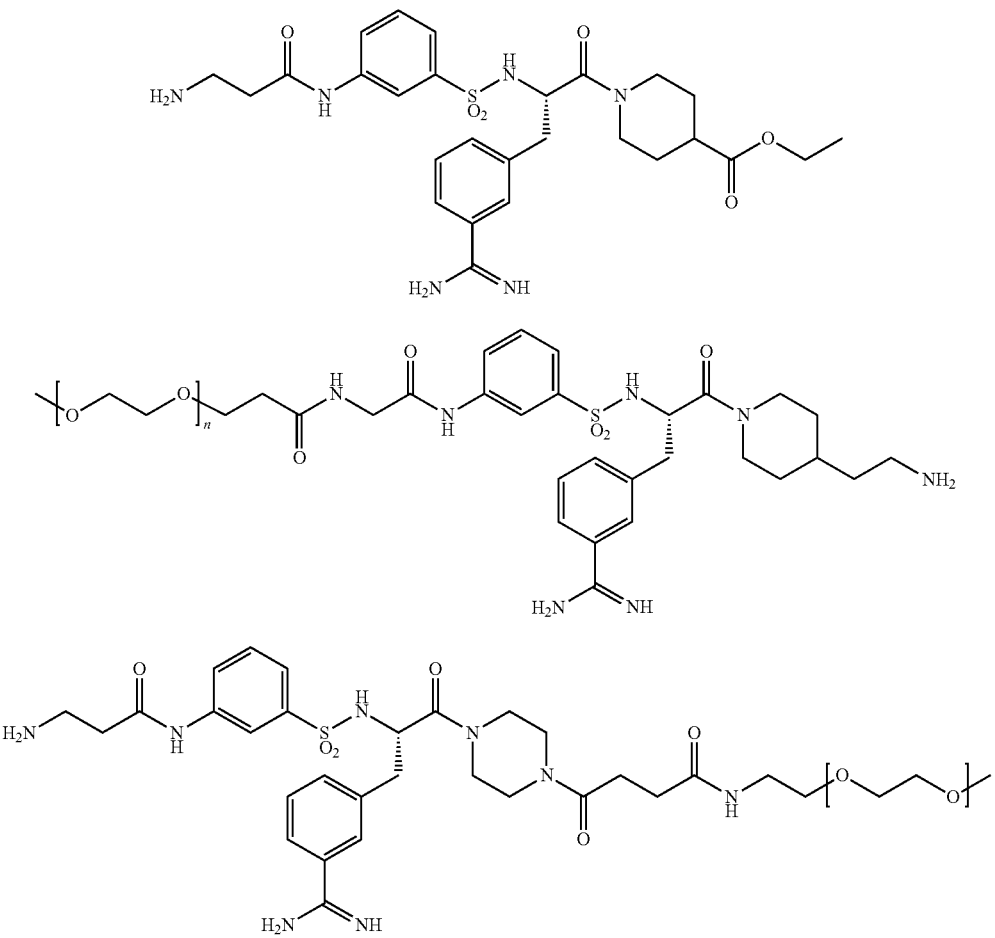

Combinations

As used herein the term "combination" when used in reference to the use of a matriptase inhibitor in combination with another therapeutic/active agent (e.g., anti-flu) means i) simultaneously (e.g., in separate compositions or a single composition); ii) simultaneously as a single dual action compound (e.g., a conjugate of the two, the matriptase inhibitor chemically linked with another antiviral) in a single composition; or iii) subsequently (e.g., in separate compositions wherein the matriptase inhibitor is administered before or after the other antiviral). The matriptase inhibitor and the therapeutic agent can act additively or, more preferably, synergistically. Other therapeutic agents which may be used with matriptase inhibitors include but are not limited to a viral M2 ion channel inhibitor or a neuraminidase inhibitor. More specifically, such agents may be a siRNA, Tamiflu™ (oseltamivir), Relenza™ (zanamivir), laninamivir, peramivir, amantadine, rimantadine, ribavirin vitamin C, Cold Fx™, Echinacea and ginseng.

The present invention encompasses therefore the use of a combination of two, three or more active ingredients including a matriptase inhibitor. A combination of three compounds in accordance of the present invention can include a matriptase inhibitor (e.g., a compound as defined above), another anti-influenza agent and a decongestant.

Routes of Administration

Matriptase inhibitors may be administered in a pharmaceutical composition. Pharmaceutical compositions may be administered in unit dosage form. The route of administration can depend on a variety of factors, such as the environment and therapeutic goals, and particulars about the subject. Any appropriate route of administration may be employed, for example, nasally, transdermal (topical), parenteral, subcutaneous, intramuscular, intramammary, intracranial, intraorbital, ophthalmic, intraventricular, intracapsular, intraarticular, intraspinal, intracisternal, intraperitoneal, intranasal, aerosol, or oral administration. Examples of specific routes of administration include parenteral, e.g., intravenous, intradermal, subcutaneous, intramammary; oral (e.g., inhalation, by nebulizer); transdermal (topical); transmucosal, and rectal administration. A preferred route of administration is with a nebulizer or inhaler.

Conventional pharmaceutical practice may be employed to provide suitable formulations or compositions to administer such compositions to patients. Methods well known in the art for making pharmaceutical compositions and formulations are found in, for example, Remington: The Science and Practice of Pharmacy, ($20^{th}$ ed.) ed. A. R. Gennaro A R., 2000, Lippincott: Philadelphia.

Excipients/Carriers

As indicated above, the composition may further comprise a pharmaceutically acceptable carrier or excipient. As used herein, the terms "pharmaceutically acceptable" refer to molecular entities and compositions that are physiologically tolerable and do not typically produce an allergic or similar untoward reaction, such as gastric upset, dizziness and the like, when administered to animals (e.g., cows, humans). Preferably, as used herein, the term "pharmaceutically acceptable" means approved by regulatory agency of the federal or state government or listed in the U.S. Pharmacopeia or other generally recognized pharmacopeia for use in animals, and more particularly in humans.

The term "carrier" refers to a diluent, adjuvant, excipient, or vehicle with which the compounds of the present invention may be administered. Sterile water or aqueous saline solutions and aqueous dextrose and glycerol solutions may be employed as carriers, particularly for injectable solutions. Suitable pharmaceutical carriers are described in "Remington's Pharmaceutical Sciences" by E. W. Martin.

The pharmaceutical compositions of the present invention may therefore contain non-limiting pharmaceutically acceptable excipients/carriers such as solubilizing/diluting agents, antioxidants, enteric coatings, absorption enhancers, pH adjusting agents and buffers, dispersing agents, coatings, antibacterial, antifungal agents, absorption delaying agents (controlled time-release), osmolarity adjusters, isotonic agents, preservative agents, stabilizers, surfactants, emulsifiers, sweeteners, thickening agents, solvents, emollients, coloring agents, wetting agents, as well as colors and flavors and salts for the variation of osmotic pressure. As mentioned earlier, they may also contain other therapeutically valuable agents. Methods for preparing appropriate formulations are well known in the art (see e.g., Hendrickson, 2005).

The carrier/excipient is selected for administration by the selected route of administration. The use of such media and agents for pharmaceutically active substances is well known in the art (Rowe et al., Handbook of pharmaceutical excipients, 2003, 4th edition, Pharmaceutical Press, London UK). Except insofar as any conventional media or agent is incompatible with the active compound, use thereof in the pharmaceutical compositions of the invention is contemplated.

Therapeutic formulations for oral administration, may be in the form of tablets or capsules; for transmucosal (e.g., rectal, intranasal) or transdermal/percutaneous administration may be in the form of ointments, powders, nasal drops, sprays/aerosols or suppositories; for topical administration, may be in the form of ointments, creams, gels or solutions; for parenteral administration (e.g., intravenously, intramuscularly, intradermal, intramammary, subcutaneously, intrathecally or transdermally), using for example injectable solutions. Furthermore, administration can be carried out sublingually or as ophthalmological preparations or as an aerosol, for example in the form of a spray. Intravenous, intramuscular or oral administration is a preferred form of use.

Oral

For the purpose of oral therapeutic administration, the active compound can be incorporated with excipients and used for example in the form of tablets, troches, dragees, hard or soft gelatin capsules, solutions (e.g., syrups), aerosols, emulsions or suspensions, or capsules. For the preparation of formulations for oral administration, the compounds of the present invention may be admixed with pharmaceutically inert, inorganic or organic excipients (e.g., pharmaceutically compatible binding agents, and/or adjuvant). The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Examples of suitable excipients for tablets, dragees or hard gelatin capsules for example include lactose, maize starch or derivatives thereof, talc or stearic acid or salts thereof. Suitable excipients for use with soft gelatin capsules include for example vegetable oils, waxes, fats, semi-solid or liquid polyols etc.; according to the nature of the active ingredients it may however be the case that no excipient is needed at all for soft gelatin capsules.

For the preparation of solutions and syrups, excipients which may be used include for example water, polyols, saccharose, invert sugar and glucose.

Nasal/Inhalation

A inhibitory compound and/or composition of the invention may also be administered directly to the lung by inhalation. For administration by inhalation, a compound and/or composition of the invention may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the invention directly to the lung. An aerosol spray from pressured container or dispenser which contains a suitable propellant, e.g., a gas such as carbon dioxide, or a nebulizer.

Alternatively, a Dry Powder Inhaler ("DPI") device may be used to administer a compound and/or composition of the invention to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insulator may be formulated containing a powder mix of a compound of the invention and a suitable powder base such as lactose or starch for these systems.

Another type of device that may be used to deliver a compound and/or composition of the invention to the lung is a liquid spray device. Liquid spray systems use extremely small nozzle holes to aerosolize liquid drug formulations that may then be directly inhaled into the lung.

In one embodiment, a nebulizer is used to deliver a compound and/or composition of the invention to the lung. Nebulizers create aerosols from liquid drug formulations by using, for example, ultrasonic energy to form fine particles that may be readily inhaled. Examples of nebulizers include devices supplied by Sheffield/Systemic Pulmonary Delivery Ltd. (see, Armer et al., U.S. Pat. No. 5,954,047; van der Linden er al., U.S. Pat. No. 5,950,619; van der Linden et al., U.S. Pat. No. 5,970,974), Aventis, and Batelle Pulmonary Therapeutics.

In another embodiment, an electrohydrodynamic ("EHD") aerosol device is used to deliver a compound and/or composition of the invention to the lung. EHD aerosol devices use electrical energy to aerosolize liquid drug solutions or suspensions (see e.g., Noakes et al., U.S. Pat. No. 4,765,539). Elm aerosol devices may deliver drugs to the lung more efficiently than other pulmonary delivery technologies.

Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

Transmucosal or Transdermal (Topical)

For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. For suppositories, and local or percutaneous application, excipients which may be used include for example natural or hardened oils, waxes, fats and semi-solid or liquid polyols.

Parenteral

Pharmaceutical compositions suitable for injectable use include sterile aqueous solutions (where water soluble) or dispersions and sterile powders for the extemporaneous preparation of sterile injectable solutions or dispersion. Solutions or suspensions used for parenteral application can include the following components: a sterile diluent such as water for injection (where water soluble), saline solution, fixed oils (e.g., paraffin oil), polyalkylene glycols such as polyethylene glycols, glycerine, propylene glycol or other synthetic solvents, oils of vegetable origin, or hydrogenated napthalenes; antibacterial agents such as benzyl alcohol or methyl parabens; antioxidants such as ascorbic acid or sodium bisulfite; chelating agents such as ethylenediaminetetraacetic acid; reducing agents such as dithiothreitol, buffers such as acetates, citrates or phosphates and agents for the adjustment of tonicity such as sodium chloride or dextrose. The pH can be adjusted with acids or bases, such as hydrochloric acid or sodium hydroxide. Biocompatible, biodegradable lactide polymer, lactide/glycolide copolymer, or polyoxyethylene-polyoxypropylene copolymers may be used to control the release of the compounds. Other potentially useful parenteral delivery systems for compounds of the invention include ethylenevinyl acetate copolymer particles, osmotic pumps, implantable infusion systems, and liposomes. The parenteral preparation can also be enclosed in ampoules, disposable syringes or multiple dose vials made of glass or plastic.

For intravenous or intramammary administration, suitable carriers include physiological saline, bacteriostatic water, Cremophor EL™ (BASF, Parsippany, N.J.) or phosphate buffered saline (PBS).

Liposomal suspensions (including liposomes targeted to specific cell types) can also be used as pharmaceutically acceptable carriers. A variety of liposomal formulations suitable for delivering a compound to an animal have been described and demonstrated to be effective in delivering a variety of compound, including, e.g., small molecules, nucleic acids, and polypeptides.

As mentioned earlier, medicaments containing the compounds of the present invention are also an object of the present invention, as is a process for the manufacture of such medicaments, which process comprises bringing one or more of the compounds of the present invention to, if desired, one or more other therapeutically valuable substances into a galenical administration form.

Kits

The present invention also encompasses kits comprising the compounds of the present invention. For example, the kit can comprise one or more compounds inhibiting influenza virus. The kit may optionally include one or more control samples and a device (e.g., inhaler, nebulizer, etc.). The compounds or agents can be packaged in a suitable container. The kit can further comprise instructions for using the kit.

Applications of the Compounds and Compositions

As used herein, the terms "treat/treating/treatment" and "prevent/preventing/prevention", refer to eliciting the desired biological response, i.e. a therapeutic and prophylactic effect, respectively. In accordance with the subject invention, the therapeutic effect comprises a decrease/reduction in the progress of the infection or in the severity of associated symptoms or a complete cure of the infection and/or associated symptoms. In accordance with the invention, a prophylactic effect may comprise a delay or decrease in the onset of, progression of, or the severity of flu infection and associated symptoms (e.g., viral titer in the subject's blood, cells or nasopharingeal swabs, runny nose, plugged nose, sneezing, sore throat, scratchy throat, cough, hoarseness, head congestion, chest congestion, feeling tired, fever, muscle pain, loss of appetite, headache and chills), following administration of a inhibitor of the present invention. In an embodiment, the composition of the present invention, comprising a inhibitor of formula (1), (1.1), (1.2), (2), (2.1) or (3), prevents the subject from contracting an orthomyxovirus infection. The methods, compositions formulations and uses described herein are suitable for both humans and animals (including birds), preferably mammals.

As used herein, the term "flu" and "flu infection" refers to an infectious disease caused by certain RNA viruses from the orthomyxoviridae (e.g., influenza virus) family. It includes infections by types A, B and C influenza viruses. It affects birds and mammals. The most common symptoms of the disease are chills, fever, sore throat, scratchy throat, muscle pains, headache, chest congestion, head congestion, coughing, weakness, exhaustion, loss of appetite and general discomfort.

Matriptase is known to be expressed in a variety of cancers, notably epithelia-derived human tumors such as prostate, breast, colon, stomach, ovarian, renal and cervical carcinomas (reviewed in Lee, *J. Cancer Mol.* 2(5): 183-190, 2006). Accordingly, in another aspect, the present invention provides a method for inhibiting tumor growth, progression and/or metastasis in a subject in need thereof, the method comprising administering to the subject an effective amount of the inhibitor of formula (1), (1.1), (1.2), (2), (2.1) or (3) defined above. In another aspect, the present invention provides the use of the inhibitor of formula (1), (1.1), (1.2) (2), (2.1) or (3) defined above for inhibiting tumor growth, progression and/or metastasis in a subject. In another aspect, the present invention provides the use of the inhibitor of formula (1), (1.1), (1.2), (2), (2.1) or (3) defined above for the preparation of a medicament for inhibiting tumor growth, progression and/or metastasis in a subject.

Dosages

Compositions and formulations of the present invention are administered in amounts and at a frequency sufficient to prevent or treat flu infections and/or ameliorate any symptom associated with flu. The skilled artisan will appreciate that certain factors may influence the dosage required to effectively treat a subject, including but not limited to the severity of the disease or disorder, previous treatments, the general health, weight and/or age of the subject, the requirements of the patient and the mode of application, and other diseases present. Moreover, treatment of a subject with a therapeutically effective amount of a compound of the present invention can include a series of treatments.

Any amount of a composition of the present invention can be administered to a subject, provided it is not associated with important adverse effects and it is in a non-toxic dose. Typically, the amount of inhibitor contained within a single dose will be an amount that effectively prevents or treats an orthomyxovirus infection (e.g., flu) and one or more associated symptoms, without inducing significant toxicity i.e., the composition improves or reduces one or more of: viral titer in the subject's blood or cells, runny nose, plugged nose, sneezing, sore throat, scratchy throat, cough, hoarseness, head congestion, chest congestion, general weakness, fever, muscle pain, loss of appetite, headache and chills. Generally, the effective dose will not exceed CA, US and EP pharmacopeia for each product individually.

Thus, in one aspect of the present invention, the composition comprising the inhibitors of the present invention, and/or one or more other matriptase inhibitors, is administered prior to the onset of flu symptoms as a preventive measure. In another aspect of the present invention, the pharmaceutical composition of the present invention is administered in combination with a drug or drugs used to treat flu symptoms. In a further aspect, the composition of the present invention is administered once the subject has been diagnosed with flu infection or after the onset of flu symptoms. In another embodiment, the composition of the present invention is administered in combination with one or more other drugs used for the prevention and/or treatment flu infections such as Tamiflu™ (oseltamivir), Relenza™ (zanamivir), laninamivir, peramivir, amantadine, rimantadine, ribavirin, vitamin C, vitamin C, Cold Fx™, echinacea, ginseng, etc.

As used herein the expression "effective amount" or "therapeutically effective amount" is meant to refer to an amount effective to achieve the desired therapeutic effect while avoiding adverse side effects, such as an improvement of the condition of the patient. An effective amount can be administered in one or more doses. For the purposes of this invention, an effective amount on the composition of the present invention is an amount that induces a therapeutic or prophylactic response against flu infections. Such amount may vary according to the nature of the infection (specific type of viral infection), the severity of the infection, the mode of administration, the age, weight and sex of the affected subject, etc. One skilled in the art can easily and without difficulty determine what will be such effective amount. Generally, the effective amount will be between about 1 mg and about 5000 mg, preferably between 5 to 500 mg of inhibitor of the present invention. In an embodiment, the effective amount is between about 5 mg and about 400 mg of inhibitor. In another embodiment, the above-mentioned composition comprises between about 5 mg and about 300 mg of inhibitor.

The effective amount may be given daily in a single or several doses (e.g., twice daily, three times per day or 4 times per day). It may also be given every 2 days, every 3 days or once a week, as prescribed. Preferably, the effective amount is given once daily.

The effective amount to be administered to a human subject may be calculated from studies in animals. The dose may be scaled up to a human equivalent dose (HED) for starting clinical trials using published conversion tables which provide a conversion factor from mice to human of 12.3.

These are simply guidelines since the actual dose must be carefully selected and titrated by the attending physician based upon clinical factors unique to each patient. The optimal daily dose will be determined by methods known in the art and will be influenced by factors such as the age of the patient as indicated above and other clinically relevant factors.

Toxicity and Therapeutic Efficacy

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography in tandem with mass spectrometry.

Viral Targets

Compounds of the present invention may be used as anti-viral agents. In this respect, the compounds of the present invention are used against viruses that require proteolytic cleavage of HA for their activation. In a specific embodiment, viral targets of the present invention are viruses of the orthomyxoviridae family such as influenza (e.g., type A, B or C).

Subjects

The term "subject" in the context of the present invention relates to any mammal including a mouse, rat, cat, dog, cow, pig, monkey, a bird and a horse. In a specific embodiment, it refers to a human. A "subject in need thereof" or a "patient" in the context of the present invention is intended to include any subject that will benefit or that is likely to benefit from the inhibitor of the present invention. In an embodiment, a subject in need thereof is a subject diagnosed with an orthomyxovirus infection (e.g., flu). In another embodiment, a subject in need thereof is a subject that is likely to catch an orthomyxovirus infection (e.g., flu) or in which an orthomyxovirus infection (e.g., flu) infection is likely to have important health consequences (e.g., young children, elderly or immune deficient subjects). The likelihood of contracting an orthomyxovirus infection (e.g., flu) can be determined for instance with the prevalence of the disease in the subject's environment including close members of the family (sisters, brothers, parents, grandparents, uncles and aunts, spouse, colleagues, friends, etc.). In an embodiment, a subject in need thereof is a subject suffering from the orthomyxovirus infection (e.g., flu) or any associated symptoms.

The present invention is illustrated in further details by the following non-limiting examples.

Example 1

Matriptase Expression in Human Airway Epithelial Cells

RNA extracts from various human respiratory system cell lines including Calu-3, H292, A549 and Beas-2B, from normal human lungs (Ambion) were obtained using the Trizol™ extraction method to probe for matriptase mRNA expression. cDNA was obtained after reverse transcription of RNA using random primers. Next, specific primers for matriptase (FW-ctaggatgagcagctgtgga (SEQ ID NO:3); RV-aagaatttgaagcgcacctt (SEQ ID NO:4)) were used to amplify by PCR any RNA message for the protease. Water instead of RNA was used as a negative control (−) and a plasmid containing the matriptase sequence (coding for residues 1-855 of SEQ ID NO:2) was used as a positive control (+). The results showed that mRNA for matriptase was present in Calu-3, H292 and Beas-2B cells as well as in normal human lung cells (FIG. 2). These results showed that human respiratory system cells can produce the messenger RNA for the matriptase serine-protease, thus suggesting that these cells can express the enzyme in protein form.

Figure 3:
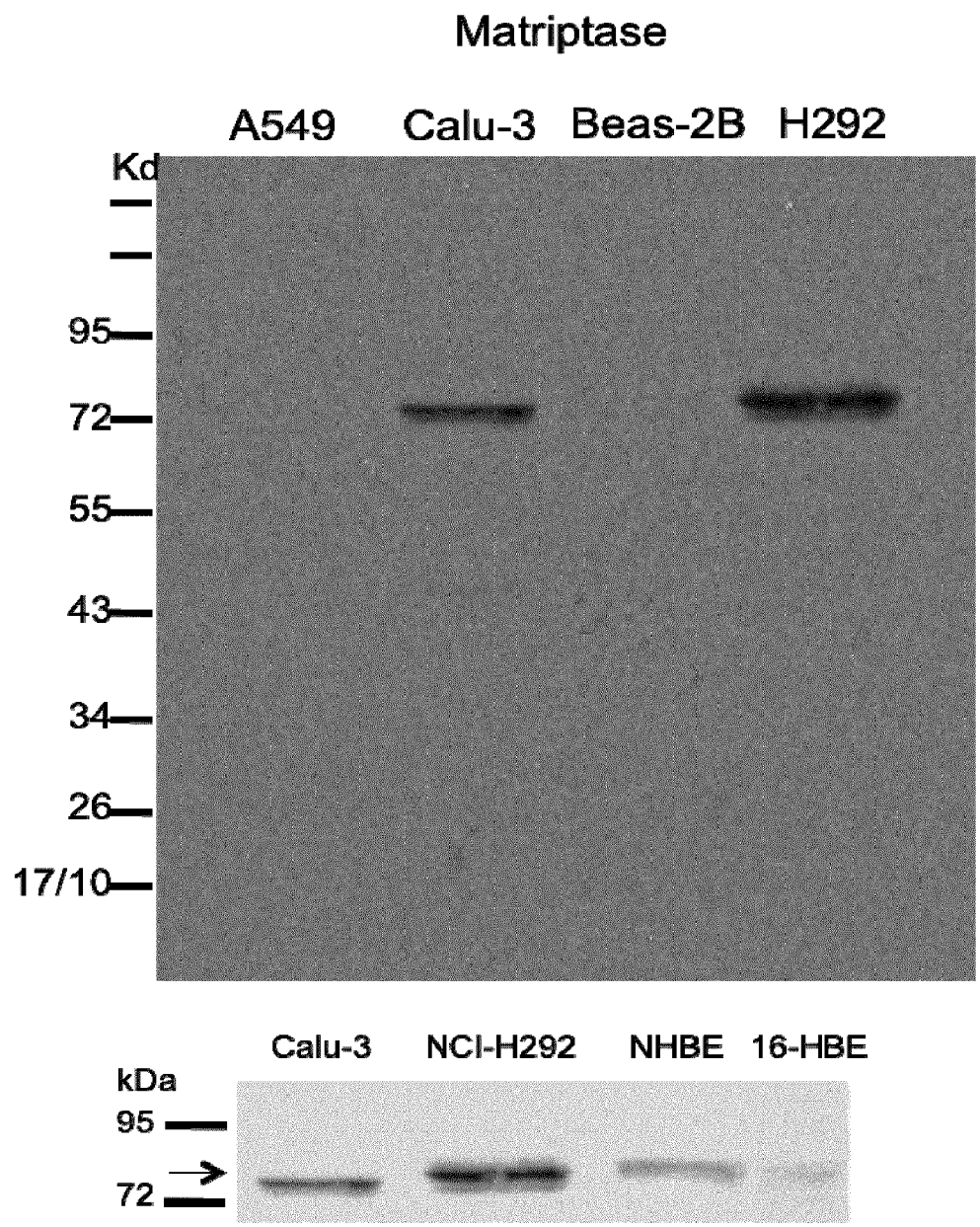
FIG. 3 shows Western blot analyses of matriptase protein expression in human respiratory system epithelial cell lines (upper panel: A549, Calu-3, Beas-2 and H292; lower panel: Calu-3, H292, NHBE and 16-HBE). Whole cell protein extracts were subjected to SDS-PAGE and transferred to nitrocellulose membranes. Using a matriptase-specific rabbit anti-human/mouse antibody and anti-rabbit-HRP secondary antibody, bands were revealed using ECL reagent. In the lower panel, Calu-3, NCl—H292 and NHBE cell extracts were analyzed on the same gel and 16-HBE cell extracts were analyzed on a separate gel using smaller wells. Results presented are reconstituted from the two gels.

It was next determined by Western blot whether the matriptase protein was expressed by human respiratory cells. Protein extracts were obtained from each cell line (Calu-3, H292, A549, Beas-2B, NHBE and 16-HBE) and subjected to electrophoresis in a polyacrylamide gel (SDS-PAGE). Following SDS-PAGE, proteins were transferred to a nitrocellulose membrane. Membranes were blocked using non-fat dry milk in Tris-Buffered Saline (TBS) with Tween™ 20. Membranes were then labeled with a rabbit anti-human matriptase/ST14-specific antibody (Bethyl laboratories, Inc.). Labeled proteins were then revealed using a donkey anti-rabbit secondary antibody coupled to horseradish peroxidase (GE Healthcare UK Ltd.) and enhanced chemiluminescence (ECL). Results showed that matriptase protein is expressed in human respiratory epithelial cell lines Calu-3 and H292, and to a lesser extent in NHBE and 16-HBE cells (FIG. 3). Predicted molecular weight of matriptase is about 75 kDa.

Figure 4:
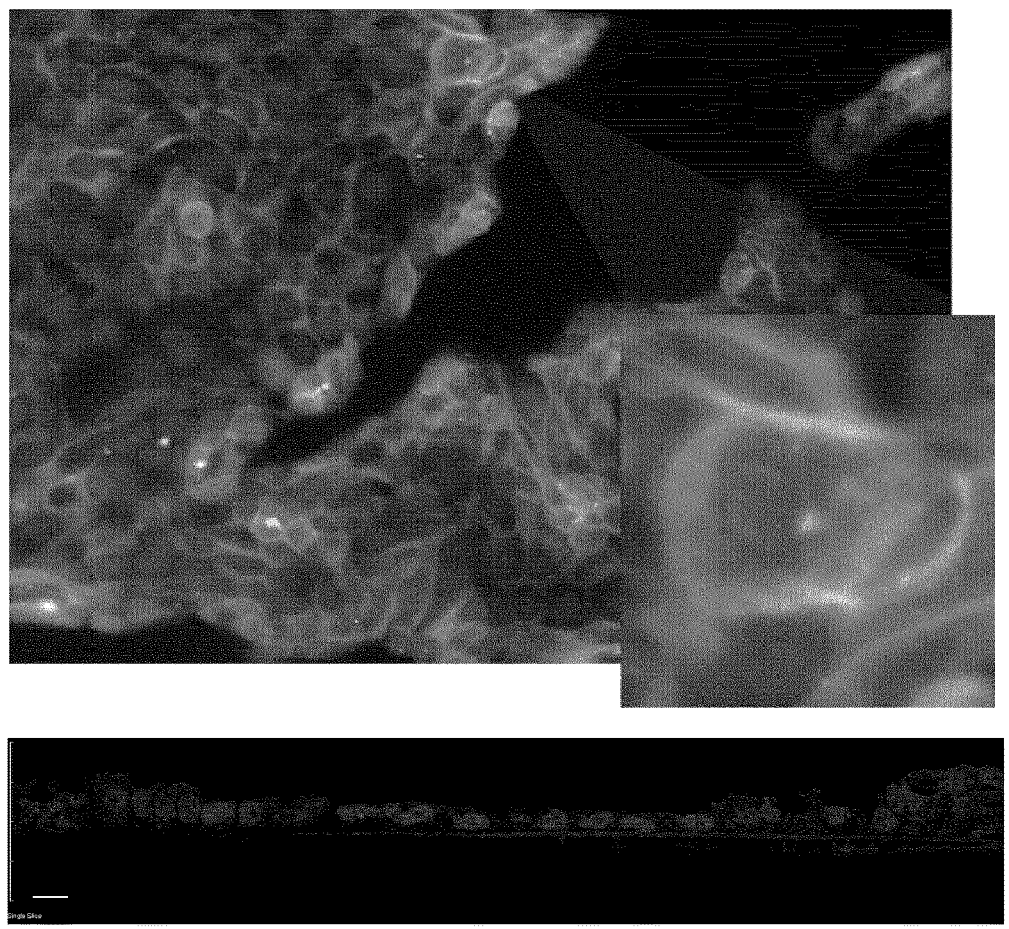
FIG. 4 shows that the matriptase protein is expressed by airway epithelial cells (Calu-3 cells) and that it is localized at least in the plasma membranes of these cells. Upper panel: Immunofluorescence of matriptase in Calu-3 cells. Calu-3 cells were grown on coverslips and stained with DAPI (staining of the nucleus), DiI (staining of membranes) and rabbit anti-human matriptase antibody and anti-rabbit Alexa-488. Fluorescence was detected using an epifluorescence microscope and appropriate filters. Lower panel: Calu-3 cells were grown in transwell chambers to confluence (tight junctions; elevated electrical resistance). Transwell membranes were removed and placed in paraffin blocks. Five-micron sections were cut and stained with DAPI (staining of the nucleus) and rabbit anti-human matriptase antibody and anti-rabbit Alexa-647. Fluorescence was detected using confocal microscopy. The straight line under the cells represents non-specific staining of the transwell membrane on which cells were grown.

The cellular localization of matriptase was also analyzed by immunofluorescence. A monolayer of Calu-3 cells was grown on cover slips and stained with Hoechst (staining of the nucleus; Invitrogen Corp.), DiI (staining of membranes; Invitrogen Corp.) and rabbit anti-human matriptase/ST14 antibody (Bethyl Laboratories Inc.) and goat anti-rabbit Alexa Fluor™-488 antibody (Invitrogen Corp.). Cover slips were analyzed using a Nikon™ TE2000-U fluorescence microscope and the appropriate filters (FIG. 4, upper panel). Also, Calu-3 cells were grown in transwell chambers to confluence (tight junctions; elevated electrical resistance). Transwell membranes were removed and placed in paraffin blocks. Five-micron sections were cut and stained with DAPI (staining of the nucleus) and rabbit anti-human matriptase antibody and anti-rabbit Alexa-647. Fluorescence was detected using confocal microscopy (FIG. 4, lower panel). Results confirmed that the matriptase protein is indeed expressed by airway epithelial cells and that it is localized at least in the plasma membrane of these cells (FIG. 4). These results are in accordance with matriptase being a type II transmembrane serine protease.

Example 2

Figure 5:
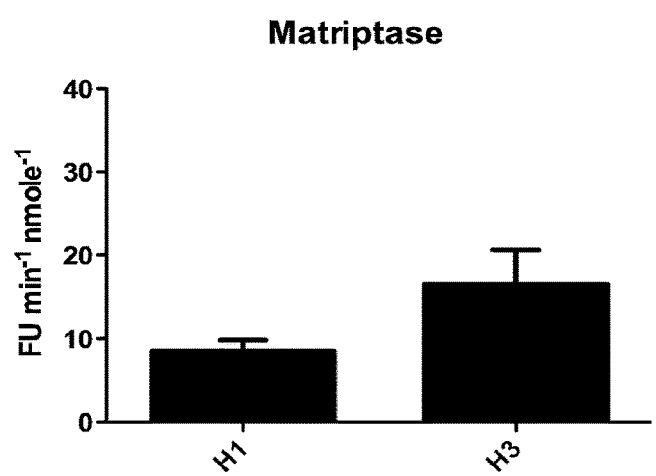
FIG. 5 shows the cleavage of HA sequence internally quenched fluorescent octapeptides by Matriptase. Internally quenched ortho-Aminobenzoic acid (Abz) fluorescent peptide substrates (IQFPs) were designed based on consensus sequences of influenza HAs most relevant to humans (H1 and H3) with the general structure Abz-XXXR↓GLFG-Tyr(3-NO$_2$) (SEQ ID NO: 6). H1 sequence was Abz-IQSR↓GLFG-Tyr(3-NO$_2$) (SEQ ID NO: 7) and H3 sequence was Abz-KQTR↓GLFG-Tyr(3-NO$_2$) (SEQ ID NO: 8). Downward pointing arrow represents cleavage site between enzyme recognition site (P4-P1) and first four amino acids of the influenza fusion peptide (P1'-P4'; conserved among all influenza strains). IQFPs containing HA sequences of H1 or H3 at fixed concentration were incubated with recombinant Matriptase as previously described (Beliveau, F., A. Desilets, and R. Leduc. 2009. Probing the substrate specificities of matriptase, matriptase-2, hepsin and DESC1 with internally quenched fluorescent peptides. *Febs J* 276:2213-2226). These data indicate that Matriptase has the potential to cleave H1 and H3 sequences.

Matriptase Promotes Influenza Hemagglutinin Cleavage/Activation and Multicycle Viral Replication Experiments were performed to determine whether matriptase has the potential to cleave influenza HA sequences. Internally quenched ortho-Aminobenzoic acid (Abz) fluorescent peptide substrates (IQFPs) were designed based on consensus sequences of influenza HAs most relevant to humans (H1 and H3) with the general structure Abz-XXXR↓GLFG-Tyr(3-NO$_2$) (SEQ ID NO: 6). H1 sequence was Abz-IQSR↓GLFG-Tyr(3-NO$_2$) (SEQ ID NO: 7) and H3 sequence was Abz-KQTR↓GLFG-Tyr(3-NO$_2$) (SEQ ID NO: 8). Downward pointing arrow represents cleavage site between enzyme recognition site (P4-P1) and first four amino acids of the influenza fusion peptide (P1'-P4'; conserved among all influenza strains). IQFPs containing HA sequences of H1 or H3 at fixed concentration were incubated with recombinant matriptase as previously described (Beliveau, F., A. Desilets, and R. Leduc. 2009. *Febs J* 276:2213-2226). The data presented in FIG. 5 indicate that matriptase has the potential to cleave influenza H1 and H3 sequences.

Figure 6:
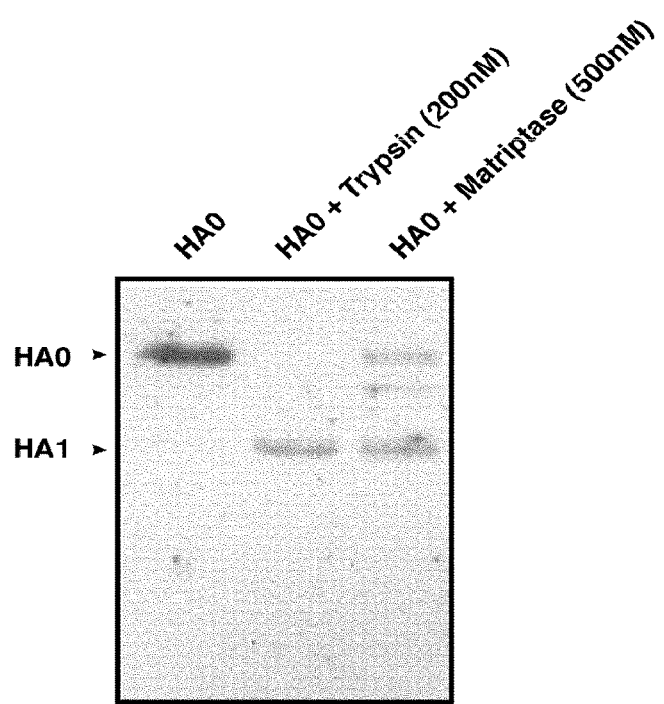
FIG. 6 shows Western blot analyses of influenza HA cleavage by matriptase. A/Puerto Rico/8/34 influenza virus (PR8) HA0 viruses (viruses with uncleaved HA) were generated as described in Klenk et al. 1984. HA0 viruses were incubated with matriptase 500 nM (or trypsin 200 nM as positive control) for 2 h at 37° C. and viral particles were disrupted using triton X-100 at a final concentration of 1%. Viral protein extracts were subjected to SDS-PAGE and transferred to nitrocellulose membranes. Using a H1 (H1N1/Pan)-specific rabbit anti-viral protein antibody and anti-rabbit-HRP secondary antibody, bands were revealed using ECL reagent. HA0 indicates uncleaved HA and HA1 represents the HA1 fragment of cleaved HA.

Next it was also tested whether the recombinant form of matriptase containing residues 596-855 of SEQ ID NO:2 produced in the inventors' laboratories (16), could cleave the HA of influenza A/Puerto Rico/8/34 (PR8) virus (for this assay a virus with non-cleaved HA was generated). HA0 viruses were generated as described in Klenk et al. 1984. HA0 viruses were incubated with matriptase 500 nM (or trypsin 200 nM as positive control) for 2 h at 37° C. and viral particles were disrupted using Triton X-100 at a final concentration of 1%. Viral proteins were subjected to SDS-PAGE and transferred to nitrocellulose membranes. Using a H1 (H1N1/Pan)-specific rabbit anti-viral protein antibody and anti-rabbit-HRP secondary antibody, bands were revealed using ECL reagent. HA0 indicates uncleaved HA and HA1 represents the HA1 fragment of cleaved HA. Results are presented in FIG. 6 and show that matriptase was able to cleave viral HA.

It was then tested whether the above-cited recombinant form of matriptase, could substitute for trypsin in the MDCK cell model of influenza replication using the PR8 virus. This cell model necessitates an exogenous protease to activate the influenza HA and to support multicycle replication.

MDCK cells were cultured to confluence and infected with 25 PFU of the PR8 virus for 1 h (to allow viral attachment) in incomplete medium containing BSA. Cells were then washed and a 1.8% Avicel microcrystalline cellulose solution in MEM containing 43 nM of matriptase (or 43 nM trypsin; positive control) was added to allow viral plaque formation. 48 h later, cells were washed and cells/viral plaques were fixed with Carnoy fixative and revealed with a solution of crystal violet. Viral plaques were counted and results were compared. Results presented in FIG. 7 demonstrate that substituting trypsin for matriptase (residues 596-855 which includes the catalytic domain) as the exogenous protease in the assay resulted in influenza HA activation and multicycle replication of the virus. The efficiency of matriptase compared to trypsin was approximately 80%. The lower left panel shows a compilation of results and efficacy of IN-1 at inhibiting matriptase in this assay (no effect on trypsin indicating selectivity). Panel C shows a concentration-response curve of inhibition of PR8 plaque formation in the presence of IN-1 in MDCK cells supplemented with Matriptase (43 nM). Thus, these results show that matriptase is able to support multicycle replication of influenza virus with high efficiency as compared to trypsin.

Since the above assay involved the addition of exogenous enzymes, it was sought to evaluate whether matriptase is involved in supporting multicycle replication of influenza virus in a system that does not require exogenous proteases. The Calu-3 airway epithelial cell line was used to test this hypothesis.

Using RNA interference technology, siRNAs specific to human matriptase were targeted in these cells. Calu-3 cells were transfected with two different siRNAs (50 nmol, S1: s13520 (Ambion) Silencer® Select siRNAs gene symbol ST14; S2: EHU012511 (Sigma-Aldrich) MISSION® esiRNA targeting human ST14 (esiRNA1)) targeted toward matriptase mRNA (target sequence of EHU012511: ACGTCCTGCTCATCACACTGATAACCAACACT-GAGCGGCGGCATCCCGGCTTTGAGGCCACCTTCT-TCCAGCT GCCTAGGATGAGCAGCTGTGGAGGC-CGCTTACGTAAAGCCCAGGGGACATTCAACAGC-CCCTACTACCCAGG CCACTACCCACCCAACATT-GACTGCACATGGAACATTGAGGTGCCCAACAAC-CAGCATGTGAAGGTGCGCTTC AAATTCTTCTACCT-GCTGGAGCCCGGCGTGCCTGCGG (SEQ ID NO:5)) using various concentrations of Lipofectamine RNAiMAX™ (0.5 to 1.5 μl). Scrambled siRNAs were used as controls. 48 h after transfection, cellular protein extracts were prepared. Extracts were subjected to polyacrylamide gel electrophoresis (SDS-PAGE) and transferred to nitrocellulose membranes. Membranes were probed for matriptase protein expression using a rabbit anti-human matriptase-specific antibody. Membranes were blocked using non-fat dry milk in Tris-Buffered Saline (TBS) with Tween™ 20. Membranes were then labeled with a rabbit anti-human matriptase-specific antibody (Bethyl Laboratories Inc.). Labeled proteins were revealed using a donkey anti-rabbit secondary antibody coupled to horseradish peroxidase (GE Healthcare UK Ltd.) and enhanced chemiluminescence (ECL).

Results presented in FIG. 8 demonstrate that the two independent matriptase-targeted siRNAs significantly block matriptase protein expression. Using 1.5 μl of Lipofectamine RNAiMAX™ for transfection, scrambled siRNA controls (AllStars negative controls, Cat #1027280; Qiagen) had little or no effect on matriptase protein expression, whereas both siRNAs 1 and 2 significantly blocked matriptase protein expression in Calu-3 cells. Densitometric analysis of blots presented in FIG. 8A revealed that matriptase-targeted siRNAs significantly inhibited matriptase protein expression in Calu-3 cells 48 h after transfection. Matriptase protein knock-downs ranged between 80-90% using these siRNAs (FIG. 8B).

Figure 9:
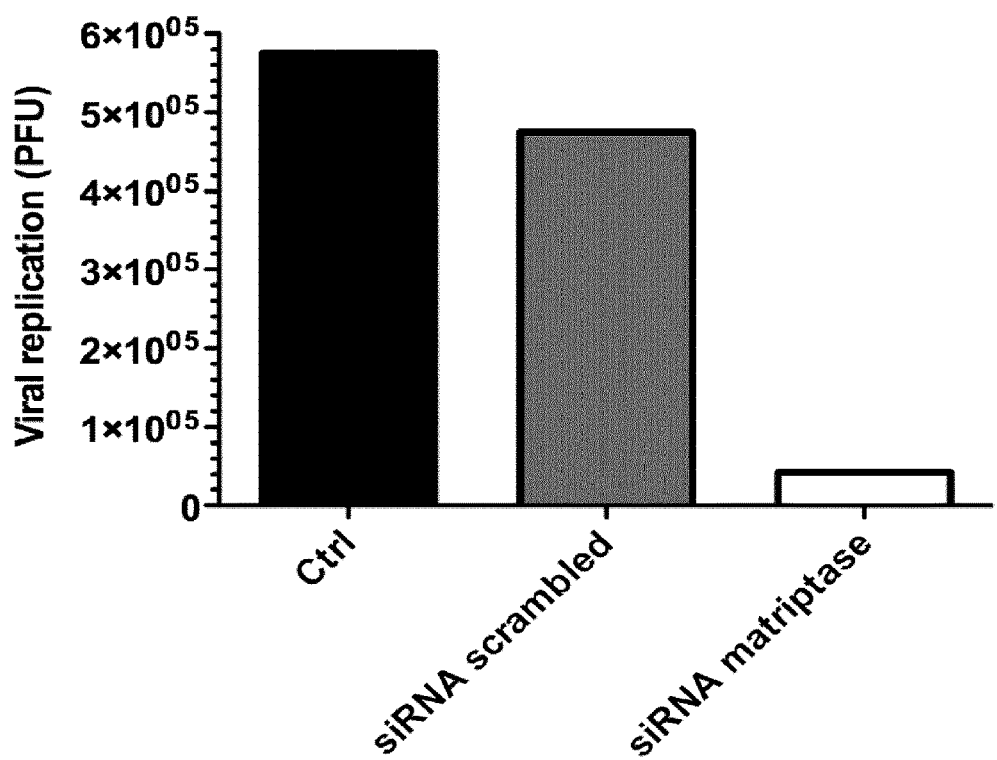
FIG. 9 shows that matriptase promotes influenza HA activation and viral replication in airway epithelial cells. Calu-3 cells were transfected (Lipofectamine RNAiMAX™ 1.5 µl) with siRNAs targeted to matriptase 48 h before infection (scrambled siRNAs were used as controls). Following transfection, cells were washed and infected with influenza A/Puerto Rico/8/34 (1000 PFU) for 1 h to allow viral attachment. Cells were then washed and incubated for 48 h. Supernatants were collected and assayed for infectious viral particles using the MDCK/trypsin system.

Further experiments were conducted to test whether this knockdown of matriptase would inhibit influenza replication. Calu-3 cells were transfected (Lipofectamine RNAiMAX™ 1.5 μl) with siRNAs S1 and S2 described above targeted to matriptase 48 h before infection (scrambled siRNAs were used as controls). Following transfection, cells were washed and infected with influenza A/Puerto Rico/8/34 (1000 PFU) for 1 h to allow viral attachment. Cells were then washed and incubated for 48 h. Supernatants were collected and assayed for infectious viral particles using the MDCK/trypsin system. Influenza virus replicated to high titers in untransfected and in scrambled siRNA-transfected cells, but replication was significantly blocked in matriptase siRNA-transfected cells (FIG. 9). Taken together these results show that matriptase, a type II transmembrane serine protease, located in the plasma membrane of airway epithelial cells (FIG. 4) is capable of promoting multicycle influenza replication (FIGS. 6, 7, and 9) and is responsible for influenza hemagglutinin activation in airway epithelial cells, which are the target of influenza viruses.

Example 3

Synthesis of Matriptase Inhibitors

Specific embodiments of the inhibitors of the present invention have a peptide backbone and include a ketobenzothiazole warhead moiety. The ketobenzothiazole moiety is involved the inhibitory action of these compounds while the peptide backbone play a role in the selectivity for matriptase over other enzymes. Synthesis of ketobenzothiazole inhibitors is exemplified below by IN-1 (compound 1), a potent inhibitor of matriptase identified by the present inventors. Of course the synthesis described below can be adapted to produce variants of peptide-ketobenzothiazole or peptide-ketoheterocyclic inhibitors or other peptide derivatives, which are within the scope of the present invention.

Materials & Methods (chemistry). Amino acids and coupling reagents were obtained from ChemImpex International (USA) and used as received. Reagents and solvents were purchased from commercial vendors and used as received unless otherwise specified. Solvents were dried as follows: THF from sodium benzophenone, DCM from phosphorus pentoxide, and MeOH from magnesium. Flash chromatography was performed on 60F254™ silica from Silicycle, thin layer chromatography from glass CCM plates from Silicycle. Analytical HPLC experiments were performed on a Agilent™ 1100 series instrument equipped with UV detector set at 223 nm and an Agilent™ Eclipse Plus C18 column (3.0×50 mm, 1.8 mm spherical particle size column) with a linear gradient of 2-50% $CH_3CN$ and $H_2O$ containing 0.1% TFA (10 min), 50-100% (4 min), 100% (4 min), 100-2% (1 min) and 2% (3 min). Final products were purified to >95% purity (HPLC-UV) by preparative HPLC (Beckman 126 instrument) using a Vydac™ C18, 250×22 mm ID, 5 μm particle size column and a linear gradient of acetonitrile containing 0.1% TFA at a flow rate of 7 mL/min. All inhibitors were obtained as trifluoroacetic acid (TFA) salts after lyophilisation. Molecular weights of compounds were confirmed by mass spectrometry (Electrospray micromass ZQ-2000 from Waters). $^1H$ and $^{13}C$ NMR spectra were recorded on an ECX-300 (Bruker Inc., USA) at 300 MHz, and are referenced to internal solvent signals.

Synthetically, compound 1 (IN-1, RQAR-ketobenzothiazole) and its analogues were assembled similarly to the method reported by Costanzo et al. (*J. Med. Chem.* 2005, 48, 1984-2008) by peptide coupling of warhead-functionalized P1 fragment with protected P4-P2 fragment (Schemes 1 to 4). The synthesis of IN-1 is shown as an example. Firstly, fragment 1-C carrying the serine trap was prepared from the corresponding Weinreb amide 1-B, by addition of in situ generated 2-lithio-benzothiazole. The resulting ketobenzothiazole was reduced in the same operation with $NaBH_4$ as a means of protecting the electrophilic keto group, then the Boc group was deprotected by acidolysis. In parallel, L-Ala benzyl ester tosylate was coupled with Fmoc-Gln-OH using HATU to afford dipeptide 1-f. After Fmoc removal, the crude dipeptide was coupled with Boc-Arg(Mtr)-OH in the presence of EDC and HOBt to give the corresponding fully protected tripeptide. Benzyl ester hydrogenolysis then generated the desired fragment 1-H. Subsequent coupling of tripeptide 1-H with warhead 1-C provided intermediate 1-K (Scheme 3). The tetrapeptide scaffold 1-K was then oxidized with IBX (Frigerio, et al., *J. Org. Chem.* 1995, 60, 7272-7276) followed by final acidolysis of protective groups with HF. Compounds were generally obtained as a 8:2 mixtures of epimers (Costanzo et al., supra), which were separated by reverse-phase preparative HPLC. Structural analogs 2-7 (Table 7, below) were obtained according to the same synthetic method.

Synthesis of IN-1 (RQAR-Ketobenzothiazole, Compound 1 in Table 7 Below)

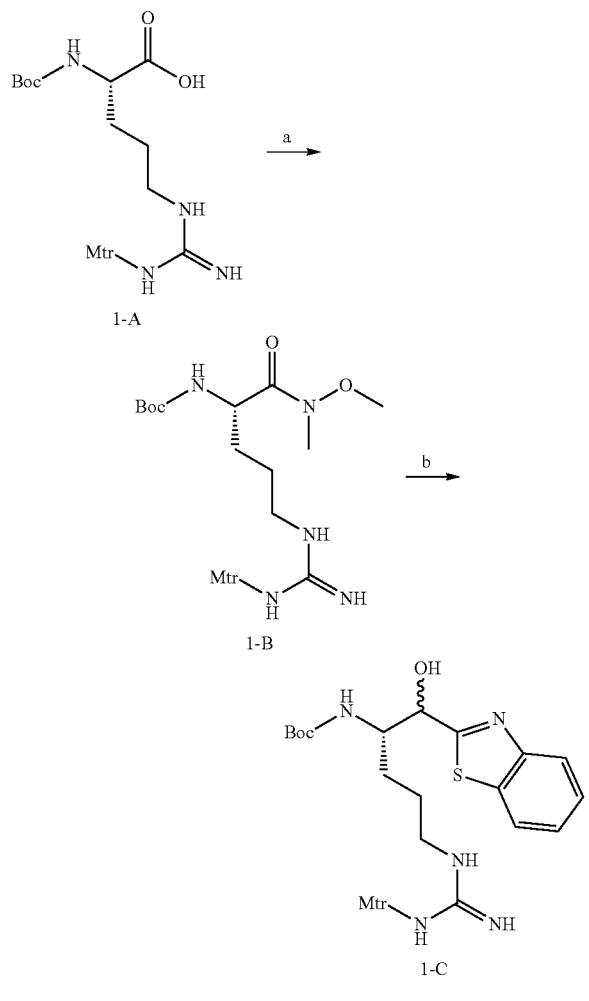

Step a:

To a solution of Boc-Arg(Mtr)-OH (Scheme 1, compound 1-A, 1357.4 mg, 2.79 mmol, 1 eq) in anhydrous THF (93 mL), were added under nitrogen (i) 1273.3 mg of HATU (3.35 mmol, 1.2 eq); (ii) 326.8 mg of HN(Me)OMe.HCl (3.35 mmol, 12 eq) and (iii) 2.4 mL of DIPEA (14 mmol, 5 eq). The reaction mixture was stirred over 3 h at ambient temperature. After completion of the reaction, the mixture was concentrated in vacuo and directly purified by flash chromatography, eluting with EtOAc/hexane (80:20 to 100: 0) to give the Weinreb amide (Compound 1-B) as a white solid (1.4 g, 93%). HPLC: 10.98 min, 90%. $^1$H NMR (300 MHz, CDCl$_3$) δ 1.41 (s, 9H), 1.55-1.71 (m, 4H), 2.59 (s, 3H), 2.67 (s, 3H), 2.80 (s, 3H), 3.22 (s, 3H), 3.29-3.33 (m, 1H), 3.72 (s, 3H), 3.82 (s, 3H), 4.63 (t, 1H), 5.47 (d, 2H), 6.20-6.31 (m, 2H) 6.53 (s, 3H). $^{13}$C NMR (75.4 MHz, CDCl$_3$) δ 11.94, 18.20, 24.12, 24.59, 28.34, 32.13, 41.00, 49.31, 55.46, 61.65, 80.38, 111.77, 120.20, 124.91, 136.25, 138.77, 155.74, 156.62, 158.54. MS (ES) m/z 530.2 (M+H)$^+$.

Step b:

A solution of benzothiazole (1.7 mL, 15.5 mmol, 18 eq) in 52 mL of anhydrous THF was cooled to −75° C. with stirring under nitrogen. Butyllithium (1.02 M in hexane, 14.8 mL, 15.1 mmol, 17.50 eq) was added dropwise over 30 min at −75 to −70° C. and the mixture was stirred for an additional 30 min −75 to −70° C. To this solution was added, dropwise over 50 min, a solution of the Weinreb amide 1-B (Scheme 1; 456 mg, 0.86 mmol, 1 eq) in 27 mL of THF dried at −75 to −70° C. The reaction mixture was stirred at −75° C. for 2 h. The reaction was quenched with 20 mL of saturated aqueous NH$_4$Cl, and extracted with EtOAc (3×50 mL). The combined organic layers were washed successively with water (3×50 mL) and brine (2×50 mL, dried (MgSO$_4$)), filtered through fritted glass, and concentrated in vacuo. The residue was dissolved in dried MeOH (17.2 mL), cooled to −20° C. while stirring and treated with NaBH$_4$ (198 mg, 5.2 mmol, 6 eq). After 1 h, acetone (20 mL) was added and the reaction mixture was warmed to room temperature over 30 min. The reaction mixture was concentrated in vacuo and partitioned between water and EtOAc. The aqueous layer was extracted with EtOAc (2×20 mL), and the combined organic extracts were washed with brine (2×20 mL), dried (MgSO$_4$), filtered through fritted glass and concentrated in vacuo. The residue was purified by flash chromatography, eluting with EtOAc/hexane (80:20 to 100: 0) to give hydroxybenzothiazole (Scheme 1, intermediate 1-C) as a yellow solid (322 g, 63%). HPLC: 12.09 min, 100% purity. $^1$H NMR (300 MHz, CDCl$_3$) δ 1.24 (s, 4H), 1.37 (s, 5H), 1.40-1.72 (m, 4H), 2.58 (s, 3H), 2.64 (s, 3H), 2.66 (s, 3H), 3.08-3.35 (m, 2H), 3.80 (s, 3H), 4.13 (t, 1H), 5.16 (s, 1H), 5.52 (d, 2H), 6.21-6.38 (m, 3H), 6.50 (s, 3H), 7.90 (d, 1H), 7.95 (d, 1H). $^{13}$C NMR (75.4 MHz, CDCl$_3$) δ 11.9, 19.1, 23.2, 24.1, 26.9, 28.8, 40.9, 55.5, 60.4, 80.2, 112.1, 121.6, 122.5, 124.8, 124.9, 125.0, 126.9, 134.7, 136.7, 138.6, 152.7, 156.6, 157.1, 158.5, 173.0. MS (ES) m/z 606.1 (MH)$^+$.

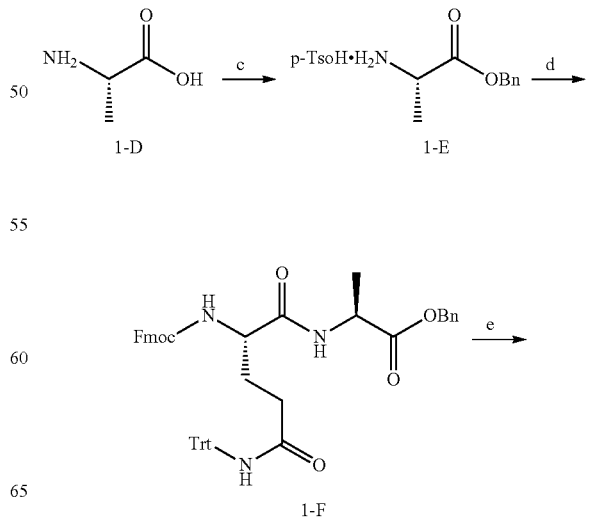

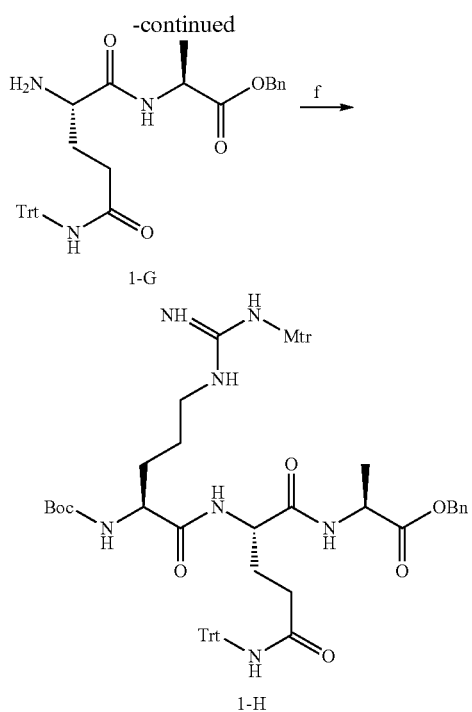

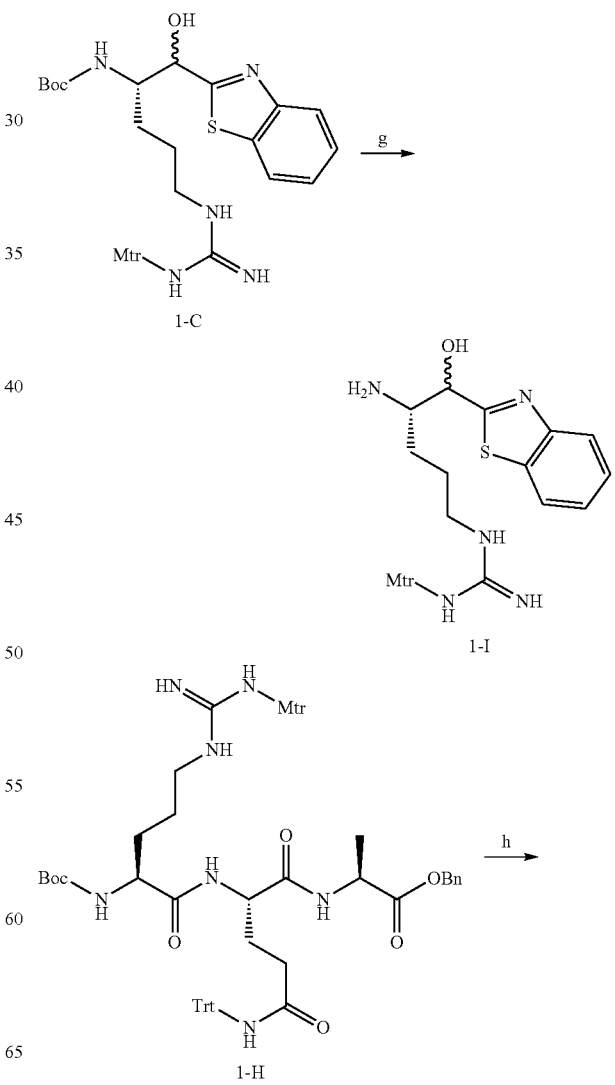

residue was diluted with CH$_2$Cl$_2$ (3×20 mL) and concentrated under in vacuo to give the intermediate free amine as a colorless oil. To a solution of 798 mg Boc-Arg(Mtr)-OH (1.64 mmol, 1.2 eq) in 14 mL of CH$_2$Cl$_2$ was added 314 mg EDC (1.64 mmol, 1.2 eq), 1.37 mmol H$_2$N-Gln(Trt)-Ala-OBn (compound 1-G, 1.00 eq) and 222 mg HOBt (1.64 mmol, 1.2 eq). The mixture was stirred at room temperature overnight. After completion, the reaction mixture was concentrated in vacuo and purified by flash chromatography (EtOAc/Hexane 80:20 to 100:0) to yield intermediate 1-H as a white solid (813 mg, 77%). HPLC-UV: 14.48 min, 80% purity. $^1$H NMR (300 MHz, CDCl$_3$) δ 1.28 (d, 2H), 1.36 (s, 10H), 1.58-1.66 (m, 1H), 2.42 (s, 3H), 2.59 (s, 3H), 2.63 (s, 3H), 3.02-3.18 (m, 1H), 3.77 (s, 3H), 4.08-4.15 (m, 1H), 4.34-4.41 (m, 2H), 4.95 (dd, 2H), 5.35 (d, 2H), 6.08-6.30 (s, 3H), 6.47 (s, 3H), 7.14-7.36 (m, 20H). $^{13}$CNMR (75.4 MHz, CDCl$_3$) δ 11.0, 17.1, 18.4, 24.2, 25.2, 28.3, 29.8, 48.5, 52.7, 53.6, 55.4, 66.9, 77.5, 79.9, 111.7, 121.1, 126.9, 127.9, 128.9, 131.3, 135.3, 138.7, 144.3, 155.0, 155.6, 158.2, 172.5. MS (ES) m/z 1018.0 (M+H)$^+$.

Scheme 3:

Step c:
To a solution of L-alanine (Scheme 2, compound 1-D) (1151.2 mg, 12.9 mmol, 1.00 eq) in 51 mL of toluene, were added (i) 23 mL of BnOH; and (ii) 2457.6 g of APTS.H$_2$O (14.2 mmol, 1.10 eq). Overcoming a Dean-Stark assembly and a condenser, the mixture was stirred at reflux overnight. After completion of the reaction, the mixture was concentrated in vacuo, dissolved in EtOAc (20 mL) and extracted with 1M HCl (3×20 mL). The combined extracts were washed with ether (4×20 mL), adjusted to pH 8-9 with NaHCO$_3$ and extracted with EtOAc (4×20 mL). The combined EtOAc extracts were dried (MgSO$_4$), filtered through fritted glass and concentrated in vacuo. The residue was crystallized in a solution of APTS.H$_2$O (2457.6 mg, mmol, 1 eq) in 20 mL of diethyl ether to give intermediate compound 1-E (Scheme 2) as a white solid (3260.0 mg, (72%; MS (ES) m/z 180.1 (MH)+).

Step d:
To a solution of Fmoc-Gln(Trt)-OH (1.83 g, 3.0 mmol, 1 eq) in 30 mL anhydrous THF were added 1.37 g HATU (3.6 mmol, 1.2 eq), 1.05 g H$_2$N-Ala-OBn (1.42 mmol, 1.0 eq), and 2.6 mL DIPEA (15.0 mmol, 5.0 eq) under nitrogen. The reaction mixture was stirred over 3 h at room temperature. After completion of the reaction, the mixture was concentrated in vacuo and purified by flash chromatography, (EtOAc/Hexane 50:50 to 70:30) to give compound 1-F as a white solid (2.07 g, 90%). HPLC: 15.19 min, 100% purity. $^1$H NMR (300 MHz, CDCl$_3$) δ 1.29 (d, 1H), 1.95-2.00 (m, 4H), 4.10-4.20 (m, 2H), 4.22-4.37 (m, 1H), 4.47-4.52 (m, 1H), 5.05-5.17 (m, 2H), 7.10-7.41 (m, 26H), 7.76 (d, 2H). $^{13}$C NMR (75.4 MHz, CDCl$_3$) δ 17.56, 30.00, 33.29, 47.16, 48.28, 53.35, 66.99, 77.49, 119.97, 125.19, 127.08, 128.22, 128.68, 141.30, 144.47, 144.52, 170.97. MS (ES) m/z 794 (M+Na)$^+$.

Step e-f:
A solution of Fmoc-Gln(Trt)-Ala-OBn (1.06 mg, 1.37 mmol, 1 eq) in 13.2 ml of CH$_2$Cl$_2$/Et$_2$NH (90:10) was stirred for 3 h at room temperature, then concentrated in vacuo. The

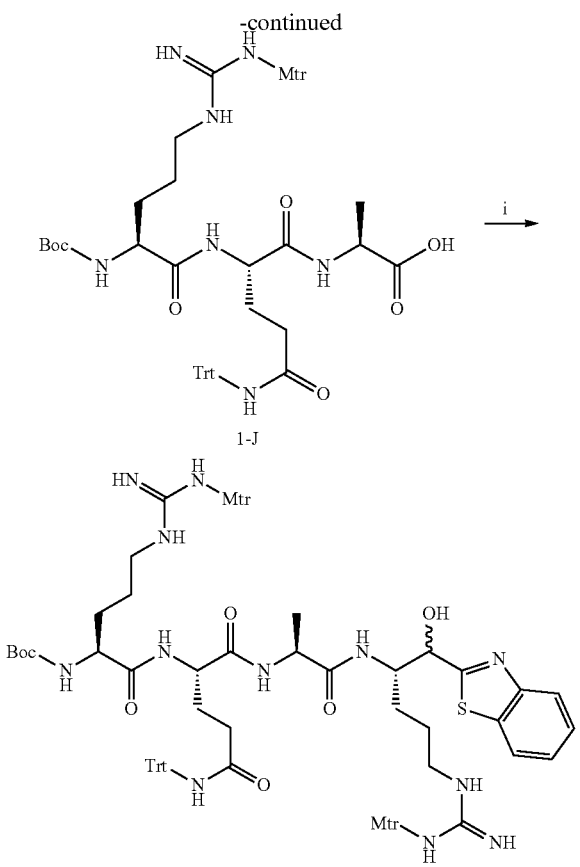

1-J

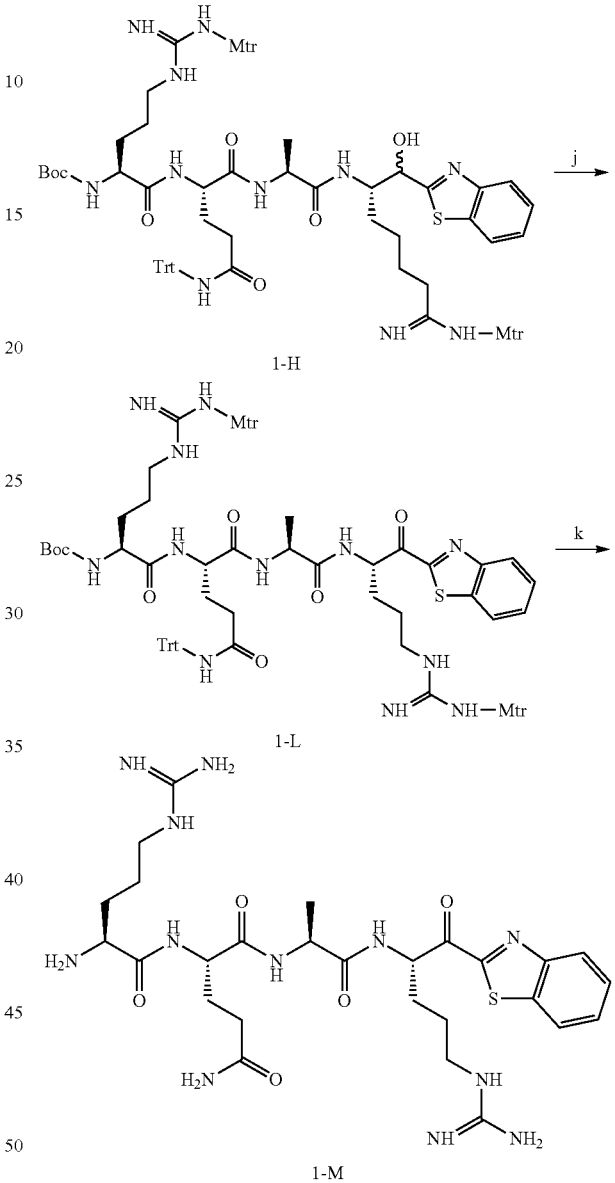

1-K

Step g:

A solution of Boc-Arg(Mtr)-benzothiazole, compound 1-C (Scheme 3; 188.8 mg, 0.31 mmol, 1 eq) in 3.1 mL CH$_2$Cl$_2$/TFA (8:2), was stirred at room temperature for 1 h and concentrated in vacuo. The residue was concentrated many times with CH$_2$Cl$_2$ (3×20 mL) to eliminate TFA and to give intermediate 1-I (Scheme 3) as yellow oil.

Step h:

The intermediate 1-H (320.7 mg, 0.31 mmol, 1 eq), 10% Pd on activated carbon (140 mg), and absolute EtOH (3.1 mL) were stirred under an atmospheric pressure of hydrogen for 1 h at ambient temperature. The resulting mixture was filtered on diatomaceous earth through fritted glass and concentrated in vacuo to give compound crude compound 1-J, which was used as such in the following step.

Step i:

To a solution of Boc-Arg(Mtr)-Gln(Trt)-Ala-OH, compound 1-J (Scheme 3; 0.31 mmol, 1 eq in anhydrous DMF, were added: (i) 353.6 mg of HATU (0.93 mmol, 3 eq); (ii) 0.31 mmol of hydroxybenzothiazole, compound 1-I (Scheme 3, 1.00 eq); and (iii) 0.3 mL of DIPEA (1.55 mmol, 5 eq). The mixture was stirred overnight, concentrated in vacuo and purified by flash chromatography, eluting with MeOH/EtOAc (95:5) to give compound 1-K (Scheme 3; 366.2 g, 84%) HPLC: 14.59 min, 83% purity. $^1$H NMR (300 MHz, CDCl$_3$) δ (s, 9H), 1.39 (d, 3H), 1.47-1.60 (m, 6H), 2.04-2.15 (m, 2H), 2.33-2.58 (m, 10H), 2.84 (s, 6H), 2.97 (s, 6H), 3.03-3.11 (m, 2H), 3.82 (s, 9H), 4.04-4.10 (m, 1H), 4.18-4.28 (m, 2H), 4.30-4.49 (m, 1H), 5.15 (d, 1H), 6.49 (s, 1H), 7.07-7.53 (m, 15H), 7.79-7.92 (m, 2H), 8.32 (d, 1H), 8.65 (d, 1H). $^{13}$C NMR (75.4 MHz, CDCl$_3$) δ 11.97, 17.23, 18.59, 24.17, 28.06, 43.24, 55.51, 76.59, 77.43, 127.02, 127.94, 128.94, 128.60, 128.73, 144.10. MS (ES) m/z 1415.0 (M+H)$^+$.

Scheme 4

Step j:

The reactant IBX (84 mg, 0.3 mmol, 1.2 eq) was added to a solution of compound 1-K (355 mg, 0.25 mmol, 1 eq) in 2.5 mL DMSO. The resulting mixture was stirred overnight at ambient temperature. The reaction mixture was washed with water (2×10 mL) and brine (2×10 mL), dried (MgSO$_4$), filtered through fritted glass, and concentrated in vacuo. The residue was purified by flash chromatography (EtOAc/Hexane 80:20 to 100:0) to give compound 1-L as a yellow solid (170 mg, 48%). HPLC: 14.94 min, 95% purity. $^1$H NMR (300 MHz, CDCl$_3$) δ 1.29 (s, 9H), 1.41 (d, 3H), 1.44-1.87 (m, 4H), 2.00-2.15 (m, 4H), 2.30-2.61 (m, 10H), 2.87 (s, 6H), 2.95 (s, 6H), 3.03-3.36 (m, 2H), 3.79 (s, 9H), 4.03-4.15 (m, 2H), 4.30-4.99 (m, 2H), 6.46 (s, 1H), 7.03-

7.20 (m, 15H), 7.41-7.52 (m, 2H), 7.86 (d, 1H), 8.16 (d, 1H). $^{13}$C NMR (75.4 MHz, CDCl$_3$) δ 11.97, 17.23, 18.59, 24.17, 28.06, 43.24, 55.51, 76.59, 77.43, 127.02, 127.94, 128.60, 128.73, 144.10. MS (ES) m/z 1414.0 (M+H)$^+$.

Step K:

A mixture of Boc-Arg(Mtr)-Gln(Trt)-Ala-Arg(Mtr)benzothiazole (compound 1-L, 206 mg, 0.15 mmol, 1 eq) and anhydrous anisole (200 μL) was placed in a teflon reaction tube of an HF apparatus and cooled to −78° C. Anhydrous HF (15-20 mL) was condensed into the tube, and the temperature was increased to 0° C. The reaction mixture was stirred at 0° C. for 3 h, concentrated in vacuo, and triturated with Et$_2$O (3×20 mL) to give a yellow solid. This solid was purified by reverse-phase HPLC, (water/MeCN/TFA 70:30: 0.1), which allowed the separation of two diastereoisomers (88:12). The major diastereomer 1-M (IN-1, Compound 1) was obtained as a white solid after lyophilisation (56 mg, 35%). HPLC: 7.31 min, 94% purity. The second diastereomer was also isolated as a pure product (8 mg, 6.87 min, 95% purity). $^1$H NMR (300 MHz, D$_2$O) δ 1.38 (d, 3H) 1.49-1.58 (m, 2H), 1.61-1.69 (m, 2H), 1.73-1.92 (m, 2H), 2.19-2.25 (m, 4H), 3.09-3.23 (m, 1H), 3.98 (t, 1H), 4.23-4.32 (m, 2H), 7.56-7.68 (m, 2H), 8.11 (d, 1H), 8.19 (d, 1H). $^{13}$C NMR (75.4 MHz, D$_2$O) δ 17.44, 24.12, 24.73, 25.02, 27.94, 33.22, 39.74, 54.66, 55.49, 74.38, 76.60, 121.76, 124.80, 125.94, 144.09, 173.49, 177.48, 177.96. HRMS calculated for C$_{27}$H$_{42}$N$_{12}$O$_5$S: 647.3200; found: 647.3228 (M+H)$^+$.

Synthesis of Structural Analogs of IN-1
(Compounds 2 to 7 in Table 7 Below)

TABLE 7

Structure of structural analogs of IN-1

| Compound # | P$_4$—P$_3$—P$_2$—P$_1$ | R$_1$, R$_2$ |
|---|---|---|
| 1 | R—Q—A—R | =O |
| 2 | R—Q—A—R | H, OH* |
| 3 | R—Q—A—K | =O |
| 4 | Q—A—R | =O |
| 5 | A—R | =O |
| 6 | R | =O |
| 7 | R—Q—A—(D)R | =O |

*3:2 mixture of diastereoisomers, absolute stereochemistry undetermined.

2-(2-amino-5-carbamimidamidopentanamido)-N-(1-{[1-(1,3-benzothiazol-2-yl)-5-carbamimidamido-1-hydroxypentan-2-yl]carbamoyl}ethyl)pentanediamide (compound 2)

The same method used for compound 1 (IN-1) described above was used to synthesize compound 2, which was obtained as a white solid (7.2 mg, 30%). HPLC: 6.08 min, 94%. $^1$H NMR (300 MHz, D$_2$O). δ 1.07 (d, 3H), 1.43-1.61 (m, 4H), 1.70-1.99 (m, 4H), 2.15-2.29 (m, 4H), 3.00-3.18 (m, 1H), 3.93 (t, 1H), 4.04-4.13 (m, 1H), 4.14-4.24 (m, 1H), 5.02 (d, 1H), 7.39-7.55 (m, 2H), 7.89 (d, 1H), 7.97-8.00 (m, 1H). $^{13}$C NMR (75.4 MHz, D$_2$O) δ 17.62, 23.37, 24.37, 26.86, 27.94, 30.82, 40.33, 52.50, 53.07, 73.44, 172.36. HRMS calculated for C$_{27}$H$_{44}$N$_{12}$O$_5$S: 649.3351; found: 649.3366 (M+H)$^+$.

N-(1-{[6-amino-1-(1,3-benzothiazol-2-yl)-1-oxohexan-2-yl]carbamoyl}ethyl)-2-(2-amino-5-carbamimidamidopentanamido)pentanediamide (RQAK-ketobenzothiazole, IN-2, compound 3 in Table 7)

The same method as used for compound 1 was also used to synthesize compound 3 with appropriate adaptations (Lysine instead of Arginine), which was obtained as a white solid (6 mg, 42%). HPLC: 5.11 min, 91%. $^1$H NMR (300 MHz, D$_2$O) δ 1.36 (d, 6H), 1.42-1.54 (m, 4H), 1.61-1.80 (m, 4H), 1.98-2.12 (m, 4H), 2.21-2.31 (m, 4H), 2.94 (t, 1H), 3.84-3.94 (m, 1H), 4.23-4.32 (m, 1H), 4.34-45 (m, 1H), 7.59-7.70 (m, 2H), 8.11 (m, 1H), 8.19 (d, 1H). $^{13}$CNMR (75.4 MHz, D$_2$O) δ 17.64, 22.42, 26.31, 26.80, 30.35, 30.94, 39.06, 40.20, 52.44, 54.98, 122.96, 124.89. HRMS calculated for C$_{27}$H$_{42}$N$_{10}$O$_5$S: 310.1603; found: 310.1603 (M2H$^+$/2).

2-amino-N-(1-{[1-(1,3-benzothiazol-2-yl)-5-carbamimidamido-1-oxopentan-2-yl]carbamoyl}ethyl)pentanediamide (Compound 4)

The same method as used for compound 1 was used to synthesize compound 4 (with appropriate adaptations), which was obtained as a white solid (10.0 mg, 30%). The second diastereomer was also isolated as a pure product (2.1 mg, 6.38 min, 93% purity). HPLC: 7.31 min, 94% purity. $^1$H NMR (300 MHz, D$_2$O) δ 1.36 (d, 3H) 1.58-1.62 (m, 2H), 1.91-1.96 (m, 2H), 2.11 (d, 2H), 2.20-2.25 (m, 2H), 3.17 (d, 2H), 3.97 (d, 1H), 4.14-4.25 (m, 1H), 4.35 (q, 1H), 7.43-7.57 (m, 2H), 8.09 (d, 1H), 8.14 (d, 1H). $^{13}$C NMR (75.4 MHz, D$_2$O) δ 16.47, 24.62, 26.44, 29.89, 30.22, 40.61, 52.13, 122.52, 122.89, 124.85, 127.81, 136.71, 152.61, 156.66, 163.98, 174.58, 176.80, 193.38. HRMS calculated for C$_{27}$H$_{42}$N$_{10}$O$_5$S: 491.2189; found: 491.2161 (M+H)$^+$.

N-[1-(1,3-benzothiazol-2-yl)-5-carbamimidamido-1-oxopentan-2-yl]-2-acetamidopropanamide (Compound 5)

The same method as used for compound 1 was used to synthesize compound 5 (with appropriate adaptations), which was obtained as a white solid (10.8 mg, 30%). The second diastereomer was also isolated as a pure product (5.1 mg, 8.04 min, 99% purity). HPLC: 8.29 min, 97% purity. $^1$H NMR (300 MHz, D$_2$O) δ 1.29 (d, 3H), 1.52-1.63 (m, 2H), 1.77-1.82 (m, 2H), 1.86 (s, 3H), 3.15 (t, 2H), 4.07 (d, 1H), 4.21 (q, 1H), 7.43-7.59 (m, 2H), 8.06 (d, 1H), 8.12 (d, 1H). $^{13}$C NMR (75.4 MHz, D$_2$O) δ 16.51, 21.49, 24.34, 27.56, 40.36, 49.93, 55.22, 122.85, 124.77, 125.12, 136.66, 152.53, 156.66, 163.92, 173.99, 175.41, 193.26. HRMS calculated for C$_8$H$_{24}$N$_6$O$_3$S: 405.1709; found: 405.1683 (M+H)$^+$.

N-[1-(1,3-benzothiazol-2-yl)-5-carbamimidamido-1-oxopentan-2-yl]acetamide (Compound 6)

The same method as used for compound 1 was used to isolate compound 6 (with appropriate adaptations), which was obtained as a white solid (6.2 mg, 48%). HPLC: 8.22 min, 99% purity. $^1$H NMR (300 MHz, CDCl$_3$) δ 1.52-1.68 (m, 2H), 1.97-2.08 (m, 2H), 2.11 (s, 3H), 3.16 (t, 2H), 5-35-5.50 (m, 1H), 7.43-7.59 (m, 2H), 8.08 (d, 1H), 8.17 (d, 1H). $^{13}$C NMR (75.4 MHz, CDCl$_3$) δ 21.47, 24.26, 27.76, 40.33, 55.36, 122.89, 124.84, 127.83, 136.78, 148.14, 152.66, 163.80, 174.27, 193.91). HRMS calculated for $C_{15}H_{19}N_5O_2S$: 334.1332; found: 334.1340 (M+H)$^+$.

Example 4

Ketobenzothiazole Tetrapeptides Inhibit Matriptase Enzymatic Activity

Experimental Procedures

Materials

Purified recombinant human matriptase, matriptase-2, hepsin and furin were prepared as described (1,2). Bovine trypsin and thrombin are from Sigma-Aldrich.

General Kinetic Methods

Enzymatic assays were performed in the following reaction buffer: 50 mM HEPES, pH 7.4 containing 500 µg/ml bovine serum albumin. Enzyme activities were monitored by measuring the release of fluorescence of an amido methyl coumarin (AMC) moiety (excitation, 360 nm; emission, 441 nm) from Boc-Gln-Ala-Arg-AMC (50 µm) (Bachem Biosciences, King of Prussia, Pa.) for 20 min at 37° C. in a FLX-800 TBE™ microplate reader (Bio-Tek Instruments, Winooski, Vt.).

Matriptase Inhibition by Ketobenzothiazole Tetrapeptides

Recombinant purified human matriptase (amino acids 596-855) (1 nM) was incubated with vehicle (1% DMSO) or 1 µM of inhibitors IN-1 (RQAR-ketobenzothiazole, Compound 1) and IN-2 (RQAK-ketobenzothiazole, compound 3) for 10 minutes at room temperature. Enzyme activity was measured for 20 minutes at 37° C. using 50 µM of Boc-Gln-Ala-Arg-AMC as a substrate. Reaction was performed in a 50 mM HEPES buffer (pH 7.4) containing 5 µg/ml BSA.

For $IC_{50}$ determination, residual enzymatic activity ($V_i/V_o$) was plotted as a function of the log transformation of inhibitor concentration (log I). Data were fitted by non-linear regression analysis using GraphPad Prism 5™ software. $IC_{50}$ corresponds to the concentration of inhibitor needed to reduce the maximal enzymatic activity by 50%.

Figure 10:
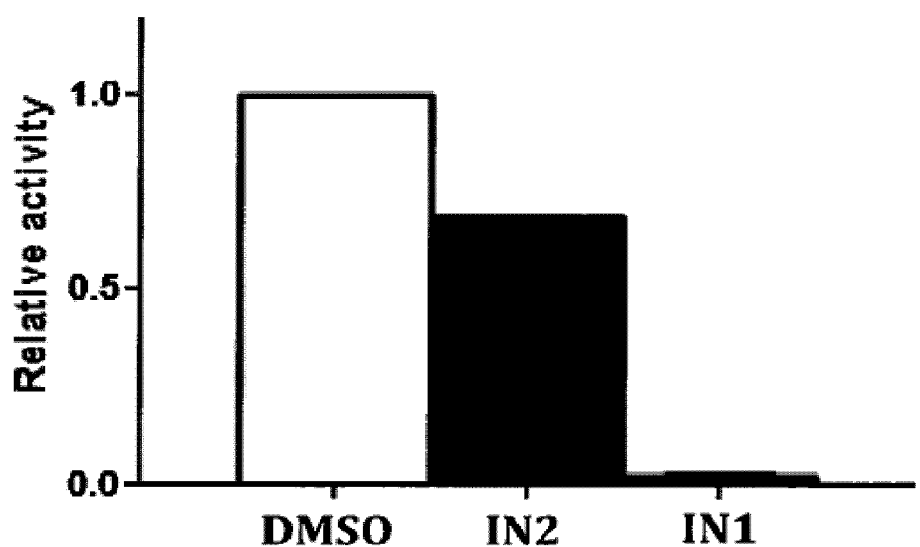
FIG. 10 shows that a ketobenzothiazole tetrapeptide representative of the compounds of the invention inhibits matriptase. Recombinant purified human matriptase (amino acids 596-855) (1 nM) was incubated with vehicle (1% DMSO) or 1 µM of inhibitors (IN-1 and IN-2) for 10 minutes at room temperature. Proteolytic activity was monitored using Boc-Gln-Ala-Arg-AMC as a fluorogenic peptide (50 µM). Results are presented as relative activity compared to the control reaction (vehicle=1).

Results show that matriptase is effectively inhibited by IN-1 and to a lesser extent by IN-2 (FIG. 10). IN-1 inhibited almost completely matriptase activity compared to the control, while IN-2 inhibited about 25% of matriptase activity at 1 µM.

To further evaluate the inhibitor profile, the dissociation of the enzyme: inhibitor complex (EI) was investigated using dilution experiments (Bieth, J. G. *Methods. Enzymol.* 1995, 248, 59-84). Dissociation of the enzyme-inhibitor (EI) complex was investigated using dilution recovery experiments. High concentration of matriptase (0.5 µM) with variable concentration of A) IN-1 (Compound 1) or B) EGR-CMK was incubated for 20 minutes at room temperature in reaction buffer to allow for the formation of the EI complex. Complexes were rapidly (1:2000) diluted in a reaction buffer containing 400 µM of Boc-Gln-Ala-Arg-AMC (~7 times Km). Activity was continuously recorded for 75 minutes and fluorescence plotted as a function of time.

Figure 11A:
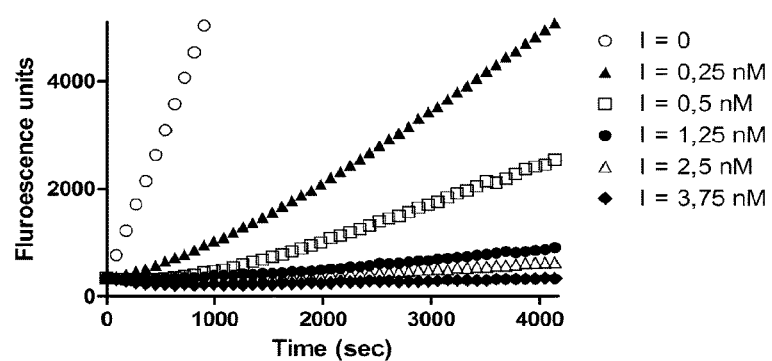
FIGS. 11A and 11B show the dissociation of enzyme:inhibitor (EI) complex using dilution experiments.
Figure 11B:
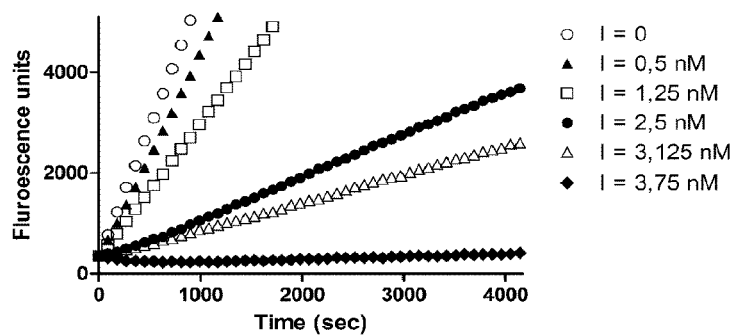

FIGS. 11A and 11B reports the comparison of the dissociation curves for IN-1 (compound 1) (FIG. 11A) and irreversible inhibitor Glu-Gly-Arg chloromethyl ketone (EGR-CMK) (FIG. 11B). The dissociation curve of EGR-CMK displays a linear product versus time relationship, indicative of irreversible inhibition. Conversely, the dissociation curve of IN-1 (compound 1) shows an exponential shape, suggesting dissociation of the enzyme: inhibitor complex. Together, these data confirm the formation of a slow, tight-binding and reversible complex between inhibitor and enzyme. This provides the advantage of a better control on inhibition.

To further characterize matriptase inhibition by IN-1 (compound 1), the inhibition constant ($K_i$) was determined using the Morrison equation for reversible tight-binding inhibition (Bieth, J. G. *Methods. Enzymol.* 1995, 248, 59-84). To evaluate inhibition potency of the ketobenzothiazoles compounds towards proteases, 1 nM of enzymes was added to the reaction buffer containing 0 nM, 10 nM or 10 µM of the different ketobenzothiazoles (0.4 µM, 4 µM and 400 µM for the reduced form of RQAR-ketobenzothiazole (Compound 2)) and 100 µM of Boc-Arg-Arg-Val-Arg-AMC for furin and 100 µM of Boc-Gln-Ala-Arg-AMC for the other proteases. If substantial inhibition occurred using a ratio of I/E<10, compounds were treated as tight-binding inhibitors (Bieth, J. G., *Methods. Enzymol.* 1995, 248, 59-84). For Ki determination of tight-binding inhibitors, enzymes diluted to concentration ranging from 0, 25 to 1 nM were pre-equilibrated with appropriate dilutions of the compounds for 15 minutes at room temperature. Residual enzyme activity was then measured by following the hydrolysis of the fluorogenic substrate Boc-Gln-Ala-Arg-AMC for 30 minutes at room temperature. Data from at least three independent experiments were averaged and residual velocities were plotted as a function of inhibitor concentration. Data were fitted by non-linear regression analysis to the Morrison Ki equation (1):

$$vi/vo = vo*(1-((((Eo+Io+Kiapp)-(((Eo+Io+Kiapp)2)-4*Eo*Io)^{1/2}))/(2*Eo))), \quad (1)$$

where vo and vi are the steady-state rates of substrate hydrolysis in the absence and presence of inhibitor, respectively, Eo, the initial concentration of enzyme, Io, the initial concentration of inhibitor and Kiapp the substrate-dependent equilibrium dissociation constant. The substrate-independent constant Ki was calculated using the equation (2):

$$Kiapp = (Ki*(1+(S/Km))), \quad (2)$$

where S is the initial concentration of substrate and Km the Michaelis-Menten constant for the enzyme—substrate interaction.

If substantial inhibition occurred only when using a ratio of I/E>10, compounds were treated as classical reversible inhibitors. In this case, inhibition assays used for Ki determination were initiated by the addition of 1 nM of protease to a reaction mixture containing the inhibitor and the fluorogenic substrate. Data generated from plots of enzyme velocity versus substrate concentration at several fixed inhibitor concentration were fitted by non-linear regression analysis to equations describing competitive, uncompetitive, noncompetitive and mixed model inhibition (Copeland, R. A Practical Introduction to Structure, Mechanism and Data Analysis. Wiley-VCH, New-York, 2000, chapter 10, pp 1-397.). For inhibition of matriptase by compound 6 (R-Benzo) and thrombin by compound 1 (RQAR-Benzo), the mixed model inhibition was the preferred model as determined by the goodness of fit (R2) and the Akaike's information criteria (AICc) and therefore used for Ki determination. All non-linear regression and statistical analysis were performed using GraphPad™ Prisms version 5.04 for Windows (GraphPad Software, San Diego, Calif., USA).

In these conditions, the RQAR-ketobenzothiazole compound 1 showed high potency for matriptase, with a $K_i$ of 0.011 nM (Table 8). A preliminary analysis of Structure-Activity Relationships (SAR) was subsequently performed by exploring the P1 position. In order to confirm the role of the keto group for matriptase inhibition, the inhibitory activity of a reduced form of the RQAR-ketobenzothiazole toward matriptase was measured (compound 2, Table 8). Reduced compound 2 (3:2 mixture of diastereoisomers at the alcohol position, undetermined absolute stereochemistry) displayed weak inhibition. Indeed, a stoichiometric ratio of I/E>1000 was needed in order to observe substantial inhibition, as testified by a $K_i$ of 6.1 µM, which contrasts with the much more potent oxidized form of compound 1 and is consistent with a functional serine trap mechanism.

TABLE 8

Structure-activity relationships of matriptase inhibitors

| Compound # | $P_4$—$P_3$—$P_2$—$P_1$ | $R_1, R_2$ | $K_i$ (nM) |
|---|---|---|---|
| 1 | R—Q—A—R | =O | $0.011^{tb} \pm 0.0004$ |
| 2 | R—Q—A—R | H, OH* | $6124^{mm} \pm 2702$ |
| 3 | R—Q—A—K | =O | $9.5^{tb} \pm 1.3$ |
| 4 | Q—A—R | =O | $0.088^{tb} \pm 0.010$ |
| 5 | A—R | =O | $1.4^{tb} \pm 0.3$ |
| 6 | R | =O | $457^{mm} \pm 132$ |
| 7 | R—Q—A—(D)R | =O | $4.6^{tb} \pm 0.8$ |

$K_i$ values were determined as described above (tb: tight-binding, mm: mixed model). Measurements of enzymatic activity were performed in triplicate and represent the means ± standard deviation of at least three independent experiments.
*3:2 mixture of diastereoisomers, absolute stereochemistry undetermined.

Table 8 reports the influence of structural variations of compound 1 on matriptase inhibition. In order to ascertain the importance of stereochemistry at the P1 position, analogue R-Q-A-(D)R (compound 7) was tested and was still active in the nanomolar range, but displayed a 400-fold lower inhibition relative to compound 1. An Arg to Lys substitution at position P1 resulted in a decrease of the Ki of about 3 orders of magnitude (compare compounds 1 and 3). Furthermore, in order to better ascertain the respective contribution of the P4, P3 and P2 residues on inhibitory profile, the peptidic portion was truncated by one, two and three residues starting from the N-terminal extremity (compounds 4-6). Deletion of the P4 residue gave a compound that conserves the profile of a tight binding inhibitor, yet with an 8-fold decreased potency compared to compound 1 (compound 4, $K_i$=0.088 nM vs. 0.011 nM for compound 1). Compound 5, in which the P4 and P3 moieties were simultaneously deleted, remains a tight binding inhibitor with 127-fold reduced potency compared to compound 1 ($K_i$=1.4 nM vs 0.011 nM). Finally, compound 6, in which the P4-P2 tripeptide portion is removed, is significantly less potent, with a Ki of 457 nM, over 30,000-fold less potent than compound 1. Additionally, compound 6 no longer behaves as a tight-binding inhibitor but as an inhibitor possessing a mixed mode of inhibition as determined by global fitting analysis for different modes of inhibition.

Matriptase Inhibition by Ketobenzothiazole Tetrapeptides in Cellulo

Next, the ability of IN-1 (compound 1) to inhibit matriptase activity in human cells was tested. Human embryonic kidney cells (HEK293) were transfected with 6 µg of pcDNA3.1™ (Mock) or pcDNA3.1™-matriptase (Matriptase) using Lipofectamine 2000™ reagent (Invitrogen) in 10-cm plates. After a 24-h transfection, the medium was replaced by serum-free media (293 SFM II™ media (Invitrogen)) in the presence or absence (vehicle) of the IN-1 (compound 1). After 24 h incubation, media was incubated with Boc-Gln-Ala-Arg-AMC substrate (50 µM) and fluorescence measured for 20 minutes at 37° C. Enzyme activity was determined in terms of released fluorescence units per minutes per µl of media for each condition.

Figure 12:
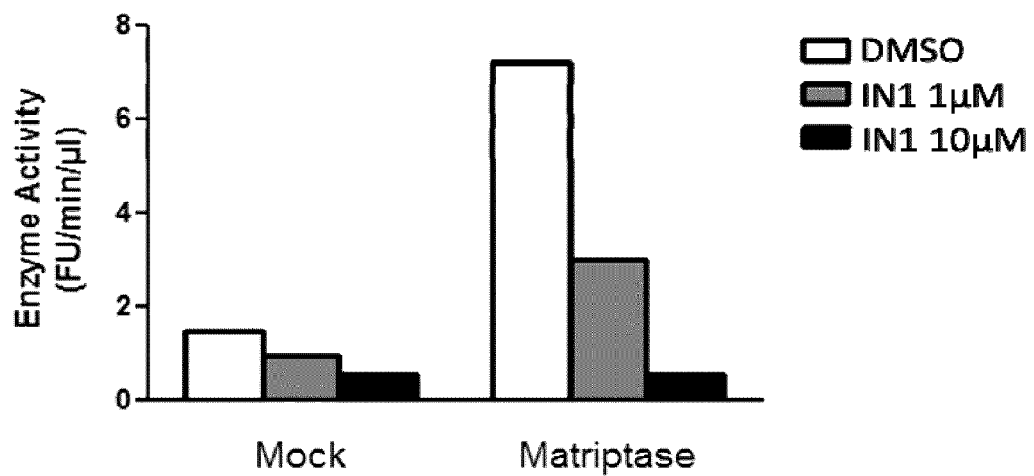
FIG. 12 shows that the ketobenzothiazole inhibitor IN-1, inhibits matriptase in cellulo. Results show the enzymatic activity measured (fluorescence units per minutes per µl of media) under each condition.

Results show that IN-1 (compound 1) efficiently inhibits matriptase activity in cultured cells at 1 µM (about 50% inhibition) and 10 µM (almost 100% inhibition; matriptase activity is returned to background level) (FIG. 12).

Example 5

Selectivity of Matriptase Inhibitors

Figure 13A:
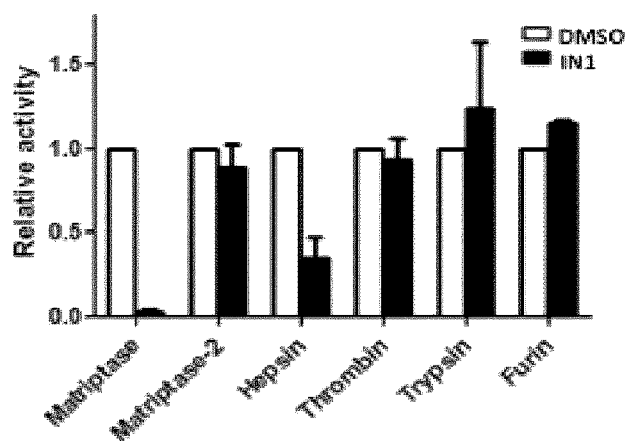
FIGS. 13A, 13B and 13C show the selectivity of IN-1 for matriptase.

The selectivity/specificity of ketobenzothiazole peptides of the present invention for matriptase activity was tested. Various proteases (matriptase; matriptase-2; hepsin; thrombin; trypsin and furin at concentration of 1 nM), were incubated with vehicle (1% DMSO) or 1 µM of IN-1 compound for 10 minutes at room temperature. Proteolytic activity was monitored by addition of the Boc-Gln-Ala-Arg-AMC peptide substrate (50 µM) for 20 minutes at 37° C. Data are presented as relative activity compared to the control reaction (vehicle=1) (FIG. 13A).

Figure 13B:
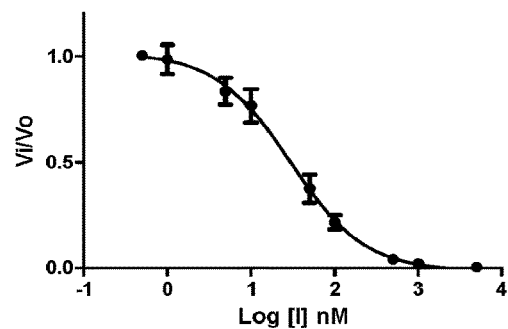
Figure 13C:
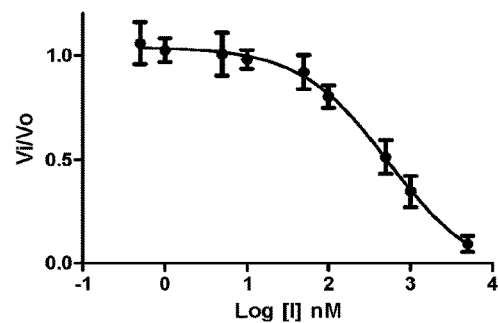

The $IC_{50}$ of IN-1 for matriptase and hepsin were also determined (FIGS. 13B and C). For the $IC_{50}$ determination of IN-1 for matriptase (FIG. 13B) and hepsin (FIG. 13C), different concentrations of inhibitors were incubated with 1 nM of enzyme. Relative activities ($V_i/V_o$) were plotted as a function of the log transformation of inhibitor concentration (log I). Data were fitted by non-linear regression analysis using GraphPad Prism 5™ software. $IC_{50}$ corresponds to the concentration of inhibitor that results in a response half way between the maximal response and the maximally inhibited response. The $IC_{50}$ value of the inhibitor was about 29 nM for matriptase while that for hepsin was about 540 nM (i.e. more than 18 times that for matriptase).

The selectivity profile of compound 1 for matriptase vs. other serine proteases, including type II transmembrane serine proteases (TTSPs), was also determined by measuring the experimental $K_i$, using the method described above. Results are presented in Table 9 below. Selectivity was expressed as the ratio of $K_i$s. Compound 1 was found to be selective for matriptase vs. other enzymes: trypsin (88-fold-protease #5 in Table 9), hepsin (100-fold-protease #3 in Table 9), matriptase-2 (300-fold-protease #2 in Table 9), TMPRSS11D (764-fold-protease #4 in Table 9), thrombin (>30000-fold-protease #6 in Table 9) and furin (no inhibition (NI)-protease #7 in Table 9). These results demonstrate that IN-1 has a good selectivity for matriptase and inhibit other related proteases with significantly less efficacy.

TABLE 9

Selectivity profile

| Proteases | $K_i$ (nM) | Selectivity $K_i$ other/$K_i$ matriptase |
|---|---|---|
| 1 | $0.011^{tb} \pm 0.0004$ | — |
| 2 | $3.3^{tb} \pm 1.0$ | 300 |
| 3 | $1.1^{tb} \pm 0.3$ | 100 |
| 4 | $8.4^{tb} \pm 2.6$ | 764 |

TABLE 9-continued

Selectivity profile

| Proteases | $K_i$ (nM) | Selectivity $K_i$ other/$K_i$ matriptase |
|---|---|---|
| 5 | $0.97^{tb} \pm 0.17$ | 88 |
| 6 | $637^{mm} \pm 131$ | >300000 |
| 7 | NI (10 µM) | — |

$K_i$ values were determined as described above (tb: tight-binding, mm: mixed model). Measurements of enzymatic activity were performed in triplicate and represent the means ± standard deviation of at least three independent experiments.

Figure 18:
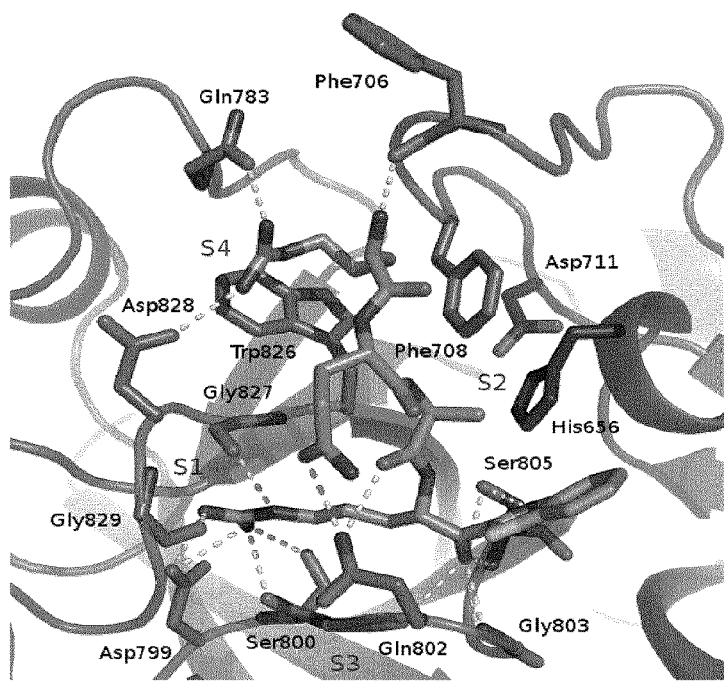
FIG. 18 shows a molecular modeling of the docking of IN-1 in the active site of matriptase. The image was generated using Pymol (The PyMOL Molecular Graphics System, Version 1.2r1pre, Schrödinger, LLC.26). Numbers refer to matriptase numbering.

In order to understand the preferred mode of docking of compound 1 in the active site of matriptase and rationalize Structure-Activity Relationships, a molecular model of compound 1 docked in the published X-ray structure of matriptase was built (FIG. 18). According to this docking model, the side chain of residue Arg in P1 is highly stabilized in a network of hydrogen bonds, which includes a salt bridge with matriptase residue Asp$^{799}$, a hydrogen bond with Ser$^{800}$ and hydrogen bonds with the backbone amide of Gly$^{827}$ and Gly$^{829}$. This may account for the preference of Arg over Lys in P1, particularly since the S1 pocket seems to be best suited to accommodate the side chain of Arg instead of Lys, which is longer and possesses reduced hydrogen bond capability compared to Arg. The side chain of residue Gln in P3 of compound 1 bridges over the Arg residue in P1 to interact with Gln$^{802}$ in the S3 pocket. Next, the side chain of the Arg residue in P4 of compound 1 interacts with the side chain of Asp$^{828}$ of matriptase via a salt bridge. It also interacts via hydrogen bonding with Gln$^{783}$. Finally, the catalytic Ser$^{805}$ residue is adequately positioned in the vicinity of the carbonyl moiety of the ketobenzothiazole group to form a covalent, reversible bond in the form of a hemiacetal. The oxygen atom of the carbonyl group is stabilized via hydrogen bonding with the backbone amides of residues Gly$^{803}$ and Ser$^{805}$.

Example 6

Figure 15:
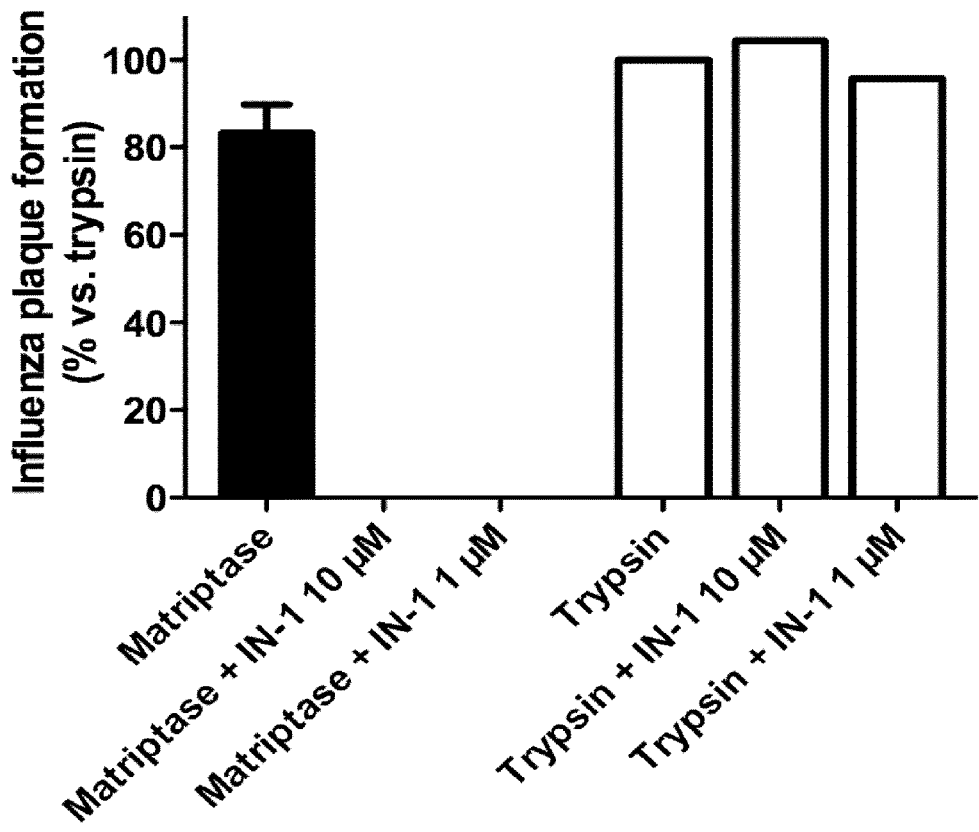
FIG. 15 is a graphic representation of a compilation of results presented in FIGS. 7 and 14, and additional experiments using trypsin as the activating protease. Viral plaques were counted in each replicate and results were compared.
Figure 16:
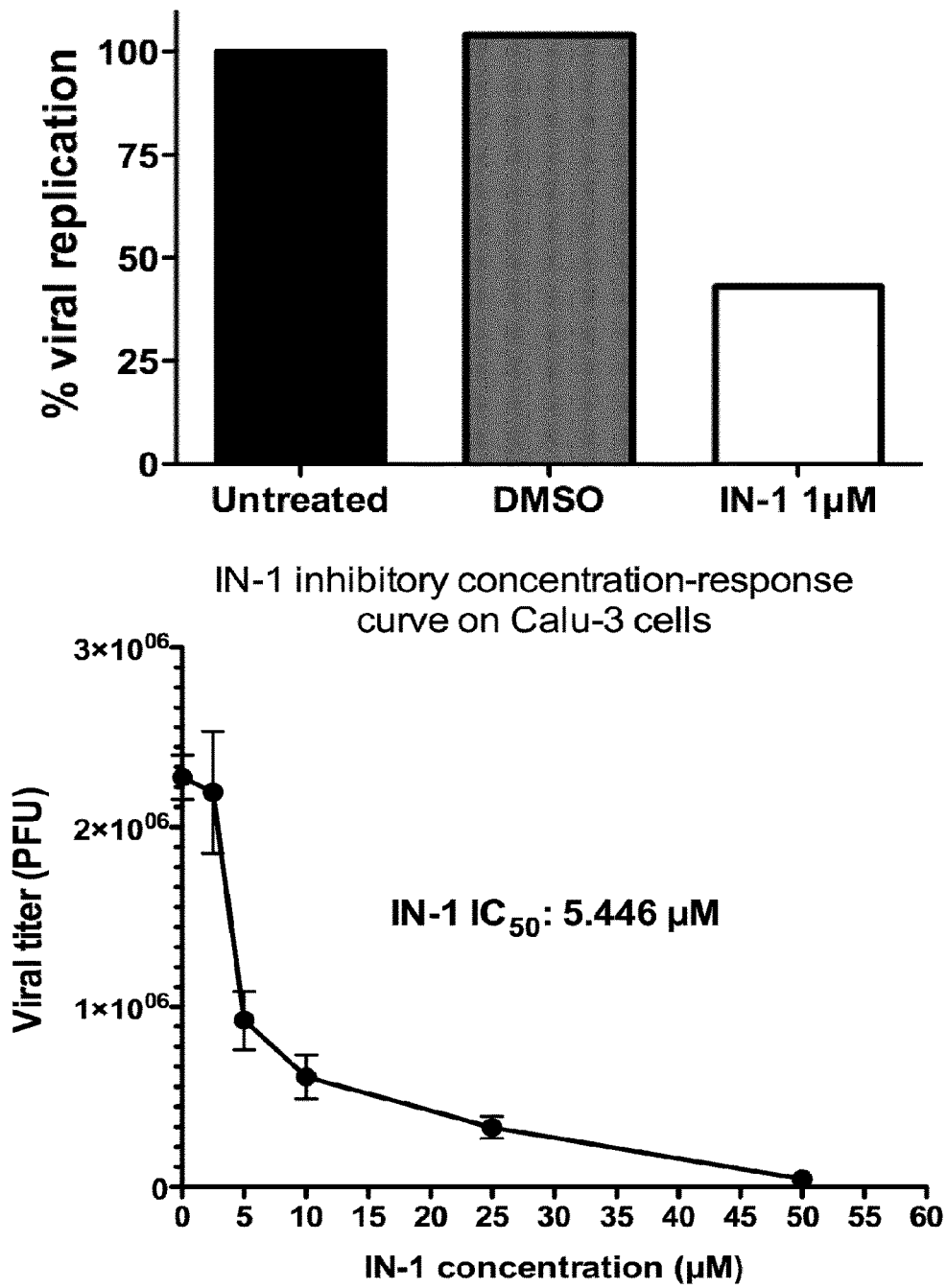
FIG. 16 shows that the IN-1 compound blocks influenza replication in airway epithelial cells. Upper panel: Calu-3 cells were cultured to confluence, washed and infected with influenza A/Puerto Rico/8/34 (1000 PFU) for 1 h to allow viral attachment. Cells were then washed and incubated for 72 h in the presence or absence of 1 µM IN-1 (or DMSO as the vehicle control 1:1000 final concentration). Supernatants were collected and assayed for infectious viral particles using the MDCK/trypsin viral plaque assay system. Lower panel: Inhibitory concentration-response curve of IN-1 in Calu-3 cells infected with influenza PR8 (H1N1). The procedure is identical to that described above except that IN-1 was added at increasing concentrations. Data was plotted using GraphPad™ Prism software and $IC_{50}$ was determined.

Ketobenzothiazole Tetrapeptides Inhibit Influenza Viral Replication in Human Airway Epithelial Cells Next was tested whether IN-1 (compound 1) was able to block influenza replication in vitro, using the MDCK/exogenous matriptase system (FIGS. 14 and 15) and the Calu-3 system that does not require exogenous proteases (FIG. 16).

In the MDCK cell system, IN-1 (compound 1) was added either 1 h or 5 h after viral attachment in an experiment identical to that presented in FIG. 7 and described in Example 2 above. MDCK cells were cultured to confluence and infected with 25 PFU of influenza A/Puerto Rico/8/34 virus for 1 h (to allow viral attachment) in incomplete medium containing BSA. Cells were then washed and a 1.8% Avicel microcrystalline cellulose solution in MEM containing 43 nM of matriptase (or 43 nM trypsin; positive control) was added to allow viral plaque formation. Matriptase inhibitor IN-1 was added to the assay at 1 h post-viral attachment. 48 h after infection, cells were washed and viral plaques were fixed with Carnoy fixative and revealed with a solution of crystal violet. Viral plaques were counted and results were compared. Similar results were obtained when IN-1 was added at 5 h post-viral attachment.

Figure 14:
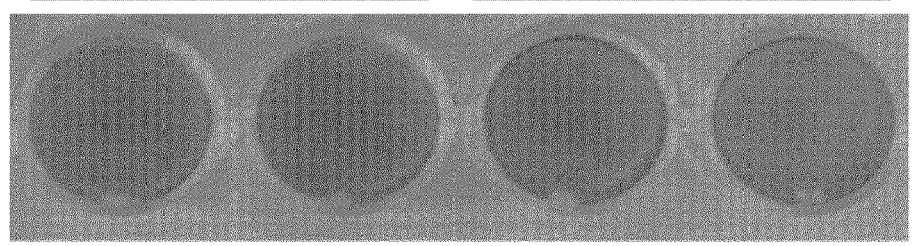
FIG. 14 shows that compound IN-1 completely abrogates influenza replication in MDCK cells with matriptase as the activating serine protease. MDCK cells were cultured to confluence and infected with 25 PFU of influenza A/Puerto Rico/8/34 virus for 1 h (PR8) to allow viral attachment, in incomplete medium containing BSA. Cells were then washed and a 1.8% Avicel microcrystalline cellulose solution in MEM containing 43 nM of matriptase was added to allow viral plaque formation. Matriptase inhibitor IN-1 was added to the assay at 1 h post-viral attachment.

The results showed that at concentration of 1 µM and 10 µM, IN-1 was able to completely abrogate influenza replication supported by matriptase (FIGS. 14 and 15).

Figure 17:
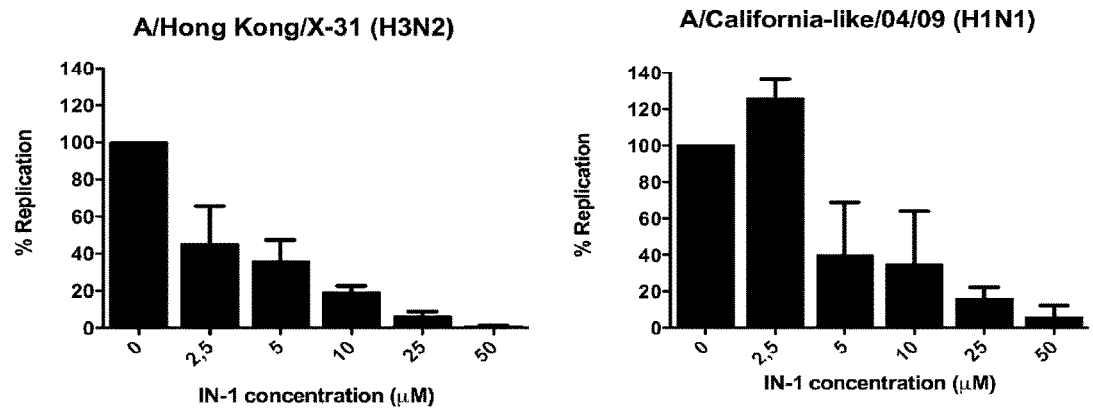
FIG. 17 shows inhibitory concentration-response curve of IN-1 in Calu-3 cells infected with influenza viruses A/Hong Kong/X-31 or a strain of the 2009 pandemic H1N1 virus isolated in Quebec during the pandemic (A/California-like/04/09). Calu-3 cells were grown to confluence and infected with 1000 PFU of influenza virus for 1 h. Cells were washed and IN-1 was added at increasing concentrations. Cell supernatants containing newly formed viruses were harvested and titrated using MDCK cells. Data was plotted using GraphPad™ Prism software.

In a separate experiment using Calu-3 cells, IN-1 blocked influenza replication by more than 50% at 72 h post-infection (FIG. 16, upper panel), and the inhibition is achieved in a dose-dependent manner (FIG. 16, lower panel). Calu-3 cells were cultured to confluence, washed and infected with influenza A/Puerto Rico/8/34 (1000 PFU) for 1 h to allow viral attachment. Cells were then washed and incubated for 72 h in the presence or absence of 1 µM IN-1 (or DMSO as the vehicle control). Supernatants were collected and assayed for infectious viral particles using the MDCK/trypsin viral plaque assay system. Influenza virus replicated to high titers in untreated or DMSO-treated cells, but replication was significantly blocked in IN-1 (1 µM)-treated cells. Interestingly, IN-1 had no effect on influenza replication when trypsin was used as the activating protease indicating a selective inhibitory activity for IN-1 (FIG. 15). FIG. 17 shows inhibitory concentration-response curve of IN-1 in Calu-3 cells infected with influenza viruses A/Hong Kong/X-31 or a strain of the 2009 pandemic H1N1 virus isolated in Quebec during the pandemic (A/California-like/04/09). These results show that inhibition of matriptase inhibits the replication of different influenza strains.

Although the present invention has been described hereinabove by way of specific embodiments thereof, it can be modified, without departing from the spirit and nature of the subject invention as defined in the appended claims.

REFERENCES

1. Cox, N. J., and K. Subbarao. 2000. Global epidemiology of influenza: past and present. *Annu Rev Med* 51:407-421.
2. De Clercq, E. 2006. Antiviral agents active against influenza A viruses. *Nat Rev Drug Discov* 5:1015-1025.
3. Hayden, F. G., and A. J. Hay. 1992. Emergence and transmission of influenza A viruses resistant to amantadine and rimantadine. *Curr Top Microbiol Immunol* 176:119-130.
4. Steinhauer, D. A., J. Martin, Y. P. Lin, S. A. Wharton, M. B. Oldstone, J. J. Skehel, and D. C. Wiley. 1996. Studies using double mutants of the conformational transitions in influenza hemagglutinin required for its membrane fusion activity. *Proc Natl Acad Sci USA* 93:12873-12878.
5. Bullough, P. A., F. M. Hughson, J. J. Skehel, and D. C. Wiley. 1994. Structure of influenza haemagglutinin at the pH of membrane fusion. *Nature* 371:37-43.
6. Sollner, T. H. 2004. Intracellular and viral membrane fusion: a uniting mechanism. *Curr Opin Cell Biol* 16:429-435.
7. Ferreira, D. F., M. P. Santo, M. A. Rebello, and M. C. Rebello. 2000. Weak bases affect late stages of Mavaro virus replication cycle in vertebrate cells. *Journal of Medical Microbiology* 49:313-318.
8. Kido, H., T. Towatari, Y. Niwa, Y. Okumura, and Y. Beppu. 1996. Cellular proteases involved in the pathogenicity of human immunodeficiency and influenza viruses. *Adv Exp Med Biol* 389:233-240.
9. Garten, W., and H. D. Klenk. 2008. *Cleavage activation of the influenza virus hemagglutinin and its role in pathogenesis*. Karger, Basel, Switzerland.
10. Klenk, H. D., and W. Garten. 1994. Host cell proteases controlling virus pathogenicity. *Trends Microbiol.* 2:39-43.
11. Skehel, J. J., and D. C. Wiley. 2000. Receptor binding and membrane fusion in virus entry: the influenza hemagglutinin. *Annu. Rev. Biochem.* 69:531-569.

12. Steinhauer, D. A. 1999. Role of hemagglutinin cleavage for the pathogenicity of influenza virus. *Virology* 258:1-20.
13. Stieneke-Grober, A., M. Vey, H. Angliker, E. Shaw, G. Thomas, C. Roberts, H. D. Klenk, and W. Garten. 1992. *Influenza* virus hemagglutinin with multibasic cleavage site is activated by furin, a subtilisin-like endoprotease. *Embo J* 11:2407-2414.
14. Zambon, M. C. 2001. The pathogenesis of influenza in humans. *Rev Med Virol* 11:227-241.
15. Bottcher, E., T. Matrosovich, M. Beyerle, H. D. Klenk, W. Garten, and M. Matrosovich. 2006. Proteolytic activation of influenza viruses by serine proteases TMPRSS2 and HAT from human airway epithelium. *J Virol* 80:9896-9898.
16. Désilets, A., J. M. Longpré, M. E. Beaulieu, and R. Leduc. 2006. Inhibition of human matriptase by eglin c variants. *FEBS Letters* 580:2227-2232.
17. Klenk H D, Garten W, Rott R. Inhibition of proteolytic cleavage of the hemagglutinin of influenza virus by the calcium-specific ionophore A23187. EMBO J. 1984 Dec. 1; 3(12):2911-2915.

The invention claimed is:

1. A method of inhibiting matriptase activity in a cell, comprising contacting the cell with an effective amount of:
   (i) a compound of formula (1):

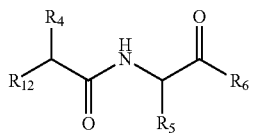

(1)

or a pharmaceutically acceptable salt, hydrate, solvate, or stereoisomer thereof, wherein
$R_{12}$ is $NHR_7$; wherein $R_7$ is

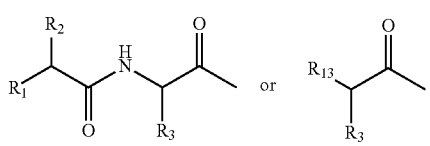

$R_{13}$ is H, $NH_2$ or $NHR_7$; wherein $R_7$ is an alkyl, aryl, (C=O)-alkyl, (C=O)-aryl, $SO_2$-alkyl or $SO_2$-aryl, C(=NH)—$NH_2$, C(=NH)—NHalkyl, C(=NH)—NHaryl or one or more amino acids residues;

$R_1$ is H, $NH_2$ or $NHR_7$; wherein $R_7$ is an alkyl, aryl, (C=O)-alkyl, (C=O)-aryl, $SO_2$-alkyl or $SO_2$-aryl, C(=NH)—$NH_2$, C(=NH)—NHalkyl, C(=NH)—NHaryl or one or more amino acids residues;

$R_2$ and $R_5$ are independently —$CH_2$—$R_8$ or

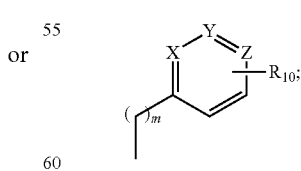

wherein $R_8$ is $(CH_2)n$-NH(C=NH)NH—$R_{14}$ or $(CH_2)n$-NH—$R_{14}$, wherein,
n is 1 to 4;
m is 0 to 3;
$R_{10}$ is —C(=NH)—$NH_2$, $NH_2$ or NH alkyl; and
$R_{14}$ is H, alkyl, $NH_2$, $NO_2$ or COalkyl;

$R_3$ is a linear alkyl; an alkyl substituted with (CO)NH₂, (CO)OH, NH₂, NHCO-alkyl, NHCO-aryl, NHSO₂-alkyl, NHSO₂-aryl or heteroaryl; an aryl, a substituted aryl, an heteroaryl or a substituted heteroaryl;

$R_4$ is an alkyl, an aryl, a substituted alkyl, a substituted aryl, an heteroaryl, a substituted heteroaryl, a side chain of an amino acid residue or a substituted side chain of an amino acid residue;

$R_6$ is

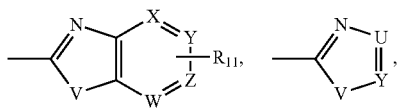

CF₃, CO₂H, CONH₂, CONH-alkyl, CONH-aryl or CO-(amino acid residue)$_p$, wherein p is 1 to 3;

wherein W, X, Y and Z are independently N or CH;
V and U are independently O, NH, NCH₃ or S; and
$R_{11}$ is H, CO₂H, CONH-alkyl, CONH-aryl, aryl, heteroaryl, halide or CO-(amino acid residue)$_q$, wherein q is 1 or 2;

wherein the amino acid residue is isoleucine, leucine, lysine, methionine, phenylalanine, threonine, tryptophan, valine, arginine, alanine, asparagine, aspartic acid, cysteine, glutamic acid, glutamine, glycine, histidine, proline, serine, tyrosine, 3-amino-propionic acid, 2,3-diamino propionic acid, alpha-aminoisobutyric acid (Aib), 4-amino-butyric acid, N-methylglycine (sarcosine), hydroxyproline, ornithine, citrulline, t-butylalanine, t-butylglycine, N-methylisoleucine, phenylglycine, cyclohexylalanine, cyclopentylalanine, cyclobutylalanine, cyclopropylalanine, cyclohexylglycine, cyclopentylglycine, cyclobutylglycine, cyclopropylglycine, norleucine (Nle), norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydro-isoquinoline-3-carboxylix acid, beta-2-thienylalanine, methionine sulfoxide, L-homoarginine (hArg), N-acetyl lysine, 2-amino butyric acid, 2-amino butyric acid, 2,4,-diaminobutyric acid, p-aminophenylalanine, N-methylvaline, selenocysteine, homocysteine, homoserine (HoSer), cysteic acid, epsilon-amino hexanoic acid, delta-amino valeric acid, or 2,3-diaminobutyric acid; and wherein said amino acid residue is in the (L) or (D) configuration; or (ii) a composition comprising
a compound of formula (1) as defined above and a pharmaceutically acceptable excipient;
whereby said matriptase activity is inhibited.

2. The method of claim 1, wherein said cell is an epithelial cell of the respiratory system.

3. The method of claim 1, wherein
$R_7$ is

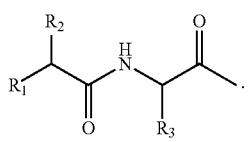

4. The method of claim 1, wherein
(i) $R_1$ is —H or —NH₂;
(ii) $R_2$ is

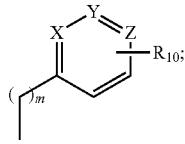

(iii) m is 1;
(iv) W is CH;
(v) X is CH;
(vi) Y is CH;
(vii) $R_{10}$ is —C(=NH)NH₂; or
(viii) any combination of (i) to (vii).

5. The method of claim 1, wherein
(i) $R_1$ is —NH₂;
(ii) $R_2$ is the side chain of arginine;
(iii) $R_3$ is an alkyl substituted with (CO)NH₂, (CO)OH, NH₂, NHCO-alkyl, NHCO-aryl, NHSO₂-alkyl, NHSO₂-aryl or heteroaryl;
(iv) $R_4$ is an alkyl;
(v) $R_5$ is —CH₂—$R_8$;
(vi) $R_6$ is

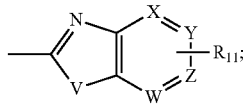

(vii) $R_8$ is —(CH₂)₃NH(C=NH)NH₂;
(viii) W is CH;
(ix) X is CH;
(x) Y is CH;
(xi) Z is CH;
(xii) V is S;
(xiv) $R_{11}$ is H; or
(xiii) any combination of (i) to (xiii).

6. The method of claim 1, wherein $R_3$ is an alkyl substituted with (CO)NH₂, (CO)OH, NH₂, NHCO-alkyl, NHCO-aryl, NHSO₂-alkyl, NHSO₂-aryl or heteroaryl.

7. The method of claim 1, wherein $R_3$ is —(CH₂)₂C(=O)NH₂.

8. The method of claim 1, wherein $R_4$ is a $C_1$ to $C_6$ alkyl.

9. The method of claim 1, wherein $R_4$ is a $C_1$ to $C_3$ alkyl.

10. The method of claim 1, wherein $R_4$ is —CH₃.

11. The method of claim 1, wherein $R_2$ and $R_5$ have the (S) configuration.

12. The method of claim 1, wherein the compound is of formula (1.1):

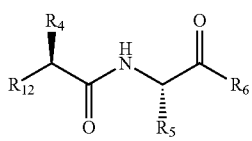

(1.1)

wherein
$R_{12}$ is $NHR_7$, wherein $R_7$ is
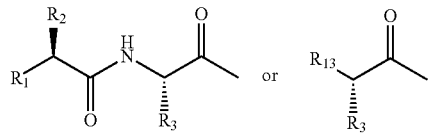
and
wherein $R_1$, $R_2$, $R_3$, $R_4$, $R_5$, $R_6$, $R_8$, $R_{10}$, $R_{11}$ and $R_{13}$ are as defined in claim 1.
13. The method of claim 12, wherein said cell is an epithelial cell of the respiratory system.
14. The method of claim 1, wherein the compound is:
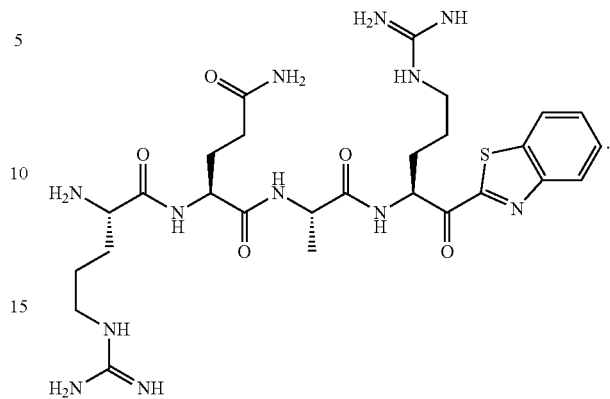

UNITED STATES PATENT AND TRADEMARK OFFICE
CERTIFICATE OF CORRECTION

PATENT NO. : 10,208,308 B2
APPLICATION NO. : 15/647878
DATED : February 19, 2019
INVENTOR(S) : Martin Richter et al.

Page 1 of 1

It is certified that error appears in the above-identified patent and that said Letters Patent is hereby corrected as shown below:

In the Claims

At Column 151, Claim number 1, Line number 42, replace the term "1,2,3,4-tetrahydro-isoquinoline-3-carboxylix acid," with --1,2,3,4-tetrahydro-isoquinoline-3-carboxylic acid,--

Signed and Sealed this
Twenty-first Day of May, 2019

Andrei Iancu
*Director of the United States Patent and Trademark Office*